United States Patent
Jiang et al.

(10) Patent No.: US 10,036,062 B2
(45) Date of Patent: Jul. 31, 2018

(54) PRIMER MIDDLE SEQUENCE INTERFERENCE PCR TECHNOLOGY

(71) Applicant: Beijing Tag-Array Molecular Test Co., Ltd, Beijing (CN)

(72) Inventors: Hong Jiang, Beijing (CN); Suwen Yue, Beijing (CN); Tongbing Liao, Beijing (CN); Bisheng Jiang, Beijing (CN); Yue Qu, Beijing (CN); Yukang Jiang, Beijing (CN)

(73) Assignee: BEIJING TAG-ARRAY MOLECULAR TEST CO., LTD., Beijing (CN)

( * ) Notice: Subject to any disclaimer, the term of this patent is extended or adjusted under 35 U.S.C. 154(b) by 0 days.

(21) Appl. No.: 14/648,678

(22) PCT Filed: Nov. 28, 2013

(86) PCT No.: PCT/CN2013/088054
§ 371 (c)(1),
(2) Date: May 29, 2015

(87) PCT Pub. No.: WO2014/082586
PCT Pub. Date: Jun. 5, 2014

(65) Prior Publication Data
US 2016/0237472 A1    Aug. 18, 2016

(30) Foreign Application Priority Data
Nov. 30, 2012    (CN) .......................... 2012 1 0506394

(51) Int. Cl.
C12P 19/34    (2006.01)
C12Q 1/686    (2018.01)
C12Q 1/6848    (2018.01)

(52) U.S. Cl.
CPC ........... *C12Q 1/686* (2013.01); *C12Q 1/6848* (2013.01)

(58) Field of Classification Search
CPC ........ C12Q 2525/185; C12Q 2549/126; C12Q 1/6848; C12Q 1/686
USPC ...................................................... 435/91.2
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,925,517 A | 7/1999 | Tyagi et al. |
| 6,090,553 A | 7/2000 | Matson |
| 6,485,903 B1 | 11/2002 | Mayrand |
| 6,569,627 B2 | 5/2003 | Wittwer et al. |
| 7,205,105 B2 | 4/2007 | Afonina et al. |

FOREIGN PATENT DOCUMENTS

| | | |
|---|---|---|
| CN | 102146432 | 8/2011 |
| CN | 102352350 | 2/2012 |
| WO | WO-2009/004630 | 1/2009 |

OTHER PUBLICATIONS

Brownie et al., "The elimination of primer-dimer accumulation in PCR," Nucleic Acids Res (1997) 25(16):3235-3241.
Hatakeyama et al., "Serum HBV RNA is a predictor of early emergence of the YMDD mutant in patients treated with lamivudine," Hepatology (2007) 45(5):1179-1186.
International Search Report and Written Opinion for PCT/CN2013/088054, dated Mar. 6, 2014, 9 pages.
Karayiannis et al., "Hepatitis B virus: old, new and future approaches to antiviral treatment," J Antimicrob Chemother (2003) 51(4):761-785.
Kellogg et al., "TaqStart Antibody: "hot start" PCR facilitated by a neutralizing monoclonal antibody directed against Taq DNA polymerase," Biotechniques (1994) 16(6):1134-1137.
Kleppe et al., "Studies on polynucleotides. XCVI. Repair replications of short synthetic DNA's as catalyzed by DNA polymerases," J Mol Biol (1971) 56(2):341-361.
Lai et al., "Prevalence and clinical correlates of YMDD variants during lamivudine therapy for patients with chronic hepatitis B," Clin Infect Dis (2003) 36(6):687-696.
Lebedev et al., "Hot start PCR with heat-activatable primers: a novel approach for improved PCR performance," Nucleic Acids Res (2008) 36(20):e131.
Lin et al., "Inhibition of multiple thermostable DNA polymerases by a heterodimeric aptamer," J Mol Biol (1997) 271(1):100-111.
Livak et al., "Oligonucleotides with fluorescent dyes at opposite ends provide a quenched probe system useful for detecting PCR product and nucleic acid hybridization," PCR Methods Appl (1995) 4(6):357-362.
Milko et al., "Cold-sensitive mutants of Taq DNA polymerase provide a hot start for PCR," Nucleic Acids Res (2003) 31(21):6139-6147.
Newton et al., "Analysis of any point mutation in DNA. The amplification refractory mutation system (ARMS)," Nucleic Acids Res (1989) 17(7):2503-2516.
Peleg et al., "Use of chimeric DNA-RNA primers in quantitative PCR for detection of Ehrlichia canis and Babesia canis," Appl Environ Microbiol (2009) 75(19):6393-6398.
Tyagi et al., "Molecular beacons: probes that fluoresce upon hybridization," Nat Biotechnol (1996) 14(3):303-308.

(Continued)

*Primary Examiner* — Cynthia B Wilder
(74) *Attorney, Agent, or Firm* — Morrison & Foerster LLP

(57) ABSTRACT

Provided is a primer middle sequence interference PCR method, and the method uses one segment of a non-complemented or same-sequence base of the middle sequence of primers to perform antisense interference inside and outside the primer molecules, so as to competitively destroy the polymerization among the primers to selectively inhibit amplification of the primer dimer (PD).

17 Claims, 7 Drawing Sheets

(56) References Cited

OTHER PUBLICATIONS

Wong et al., "Real-time PCR for mRNA quantitation," Biotechniques (2005) 39(1):75-85.
Xing et al., "Miniaturized PCR chips for nucleic acid amplification and analysis: latest advances and future trends," Nucleic Acids Res (2007) 35(13):4223-4237.

(a) PD mechanism (b) Secondary mechanism (c) Not easy to form PD (d) Not easy to form PD (a)  5'-$F_nF_nF_nF_nF_nF_nF_nF_n$TTTTTTT$F_nF_nF_nF_nF_n$-3'
5'-$R_nR_nR_nR_nR_nR_nR_nR_n$TTTTTTT$R_nR_nR_nR_nR_n$-3'

(b)  5'-$F_nF_nF_nF_nF_nF_nF_nF_n$T T T T T T T$F_nF_nF_nF_nF_n$-3'
3'-$O_nO_nO_nO_nO_nO_nO_nO_n$-5'

5'-$R_nR_nR_nR_nR_nR_nR_nR_n$TTTTTTT$R_nR_nR_nR_nR_n$-3'

(c)

PRIMER MIDDLE SEQUENCE INTERFERENCE PCR TECHNOLOGY

This application is a U.S. national stage application of International Patent Application No. PCT/CN2013/088054, filed Nov. 28, 2013, which claims benefit of priority to Chinese Patent Application No. CN 2012105063949, entitled "A PRIMER MIDDLE SEQUENCE INTERFERENCE PCR TECHNOLOGY," filed Nov. 30, 2012, and the contents of the above referenced applications are incorporated herein by reference in their entireties for all purposes.

FIELD

This invention belongs to the molecular test field, especially relates to a polymerase chain reaction PCR assay method of suppression of nonspecific amplification by using unmatched disturbing middle domain of primers.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 717412000900SeqList.txt, date recorded: Mar. 31, 2016, size: 8,915 bytes).

BACKGROUND

The initial idea of DNA exponential amplification was derived from Khorana's similar process, which is "repair replication of short synthetic DNAs as catalyzed by DNA polymerases" (Kleppe, J. Molec. Biol., 56:341) in 1971. However lacking of syntheses oligonucleotide, heat-resistant polymerase, and the thermal cycler limits its development at that time. Until 1983, Kary Mullis from genetic synthesis lab of Cetus corporation in US had the inspiration to simulate natural DNA double replication process in vitro and conceived cell free DNA amplification by thermocycling-polymerase chain reaction (PCR). The general principle of PCR is to exponential amplify a fragment DNA of bracket sequence with suitable template, two oligo-nucleotide primers, DNA polymerase, four nucleotide-triphosphates, an appropriate buffer, and cycling of DNA denaturation, renaturation, extension steps. Following available of thermal cycler instrument and development of thermostable polymerase Taq, Cetus' scientists eventually succeeded in the PCR and filed first PCR patents (U.S. Pat. Nos. 4,683,195 & 4,683,202) in 1985, certificated in 1987.

The PCR amplification consists of a series of 30-40 cycles of repeated the denature-annealing-extension three temperature steps. (1) Template DNA denature step: The target template melted by heating reaction to 94° C. for 20-30 seconds and double strands disrupted to single strand that ready for primer binding. (2) Primer annealing step: The reaction temperature is cooling to 54° C.-60° C. for 20-40 seconds allowing the primers which complement with preselected target sequence to bind on the single-stranded template. (3) Extension/elongation step: Then the temperature is increased to 72° C.-80° C., a new DNA chain synthesize by adding dNTPs to paired template from the 3'end of primer that bound on the target strand with DNA polymerase at optimum temperature. The many semi-conservative DNA strands that reverse complement to the original template are synthesized in 5' to 3' direction after repeated these denature-annealing-extension procedures and new strands also used as next cycles template. Following "n" cycles completed, an exponential increasing in the total number of target fragments between the primers is finally reached at theoretical abundance of $2^n$. But if "n" are more than 30 rounds of cycles, the primer dimers will become extremely crucial. The more precise formula $Y=(1+X)^n$ is available, where Y represents the copy number of products and X represents amplification efficiency which theoretical value of 100%, the n is number of cycles. On the first a couple of cycles, although 100% efficiency lets the products to double increase, but the amount of products still low and signal of amplification remain baseline. After about more than 10 cycles, both the amount and the signal of products enter exponential amplification or called log-phase which is most sensitive and easy test. As accumulation of products and consumption of PCR reagents such as dNTPs and primers, the reaction slow down to achieve linear stage which is no longer increased exponentially. Last stage, PCR enter the plateau, no more product accumulates due to exhaustion of components.

The PCR methods gradually matured and practical following a kind of Taq thermo-stable DNA polymerase was purified from the thermophilic bacterium, *Thermus aquaticus*, which naturally lives in hot (50 to 80° C.) environments-such as hot springs in 1985-1988. The several other pfu, Vent, Tth polymerase lately was discovered, which is dramatically improved PCR operation. Therefore the journal Science awarded Taq polymerase its first "Molecule of the Year" in 1989. The PCR with extreme high sensitivity and simplicity had spread all over the world and became most important basic techniques in life science field from 1989. Kary Mullis of Cetus, was awarded the Nobel Prize in Chemistry in 1993.

In the next twenty years, up to dozens of new improvements and methods of PCR had emerged and invented, including reverse transcription PCR (RT-PCR), In situ PCR, Ligase chain reaction (LCR), Labeled PCR (Labeled primers, LP-PCR), Reverse PCR (amplification of the unknown sequence outside two primers), Asymmetric PCR, Touchdown PCR, Nested PCR, Recombinant PCR, Multiplex PCR, Immuno-PCR, Differential display PCR, Strand displacement amplification (SDA), Nucleic acid sequence-based amplification (NASBA), Transcript-based amplification system (TAS), Q-beta replicase catalytic RNA amplification, Rolling circle amplification (RCA), Loop mediate isothermal amplification (LAMP), etc. Especially the varieties of real-time fluorescence PCR, which detected amplification progress in "real time", realize the quantitative leap versus standard PCR qualitative test at its end, such as the fluorescent dye SYBR Green I real-time PCR and various fluorescent probes TaqMan (hydrolysis probe), FRET hybridized probes, and Molecular beacon probes, as described in overview (Maisa L. Wong and Juan F. Medrano, BioTechniques 39:75-85, July 2005). The nucleic acid amplification PCR technology not only greatly improved the DNA cloning technology also revolutionary advanced the sensitivity and efficiency of nucleic acid quantification. Applications of the PCR have been expanded to many fields of biology. Now PCR technique is not single method, but it is a new subject that includes a series of new academic theory, methodology and application. The detailed review also sees the PCR books (Huang Liuyu, et al., "principle, method and application of PCR technology", Chemical industry press, 2005). The PCR that is widely applied in molecular cloning, sequencing and gene recombination, protein engineering, such as life science research, and medical care, agriculture and forestry, animal husbandry, environment protection, food safety, and many other testing applications, has become the most important core scientific technology of the 21st century. In recent years, for lower reagent consumption and higher speed heating/cooling rates, the PCR based detective devices are developing to the rapid microfluidic miniature PCR (lab—on a chip) and multiple target detection of high throughput PCR chip (PCR—on a chip), as showed in the paper "SURVEY and SUMMARY", (Da Xing, 2007, Nucleic Acids Res., Vol. 35, No. 13, p 4223-4237). Since the first report of PCR, more than million papers that involved with PCR are published, and more than three to four digits patents or related designs are filed.

After above overview, because the quantity of products at the plateau of even same PCR reaction is magnified into much different, the endpoint detection of conventional PCR can be only qualitative analysis. And the sensitivity of regular 30 of PCR is still not enough to detect the lower than the thousands copies of specimens. Otherwise the primer-dimer (PD) be fast accumulated with big trouble if reaction is excess 30 cycles. For the PD amplification and products aerosol result in false positive results, which is the reason of the conventional PCR only 30 cycles of reaction. Thus the conventional PCR which product should be check by gel electrophoresis is difficult to apply to clinical diagnosis. The kinetic PCR with fluorescence monitoring of amplification progress in real time, which was first presented by Higuchi in 1992, provides a idea in order to solve these problems of endpoint PCR. The real-time fluorescent PCR (qPCR) quantitative analysis is determined through the product quantity of fluorescence detecting (product binding fluorescence intensity) during cycling-time and the fluo-signal is directly related to the starting numbers of gene copies. The initial copies of target are negatively logarithmic scale to the cycling numbers for Ct value (Cycle threshold) when amplification product quantity increase of fluorescence signal achieved the threshold of logarithmic phase. Since the amount of DNA in the reaction double at each cycle. Thus if the template diluted double, relative one more cycle would be need to amplify to the same products or the identical threshold. The detecting of signal corresponding to the amplification products may employ with DNA binding dye as well as fluorescence label probe. The former is based on non-specific fluorescent dye that intercalate with any double-stranded DNA such as SYBR Green I real-time fluorescent PCR (U.S. Pat. No. 6,569,627); The second is sequence-specific DNA probes with a fluorescent reporter at one end and a quencher of fluorescence at opposite end of the probe. The close proximity of the reporter to the quencher prevents detection of its fluorescence. The labeled probe permits detection only after hybridization of the probe with its complementary DNA target. The probe with 5' fluorescent group, which is inhibited by 3'quencher, can be activated by degradation, such as the Taq enzyme hydrolysis of fluorescent labeled probe PCR was developed by PE company of US (Livak K J, et al., 1995, Genome Res, 7-362) who filed the hydrolysis (trade name: TaqMan) PCR invention in 1997 (U.S. Pat. No. 6,485,903). Following Epoch company improved the binding efficiency of MGB probe PCR invention (U.S. Pat. No. 7,205,105). The quenched label probe can also be activated by structure change, such as the a stem loop structure of hybridization probe-Molecular beacon (Tyagi S, et al., 1996, Nat Biotechnol comes 3-308), which's 5' end sequence bound and inhibited by 3'quencher sequence, and was applied for Molecular beacon invention in 1999 (U.S. Ser. No. 05/925,517). The other series of the double probe hybridization (FRET), Scorpion probe, Sunrise-Primer, the fluorescent Lux-Pimer, etc. are not obviously better than the hydrolysis TaqMan only in the limited certain application field. The standard SYBR Green I real-time fluorescent PCR although solved the quantitative problem of endpoint PCR, but the basic protocol still didn't improved the non-specific amplification of the primer dimers after 30 cycle reaction of regular PCR. And hydrolysis TaqMan real-time PCR, which bypassed the primer dimers signal by adding target-specific probes hybridization, has one to two order magnitude better sensitivity than conventional PCR and loses something veracity of quantification due to its complexity and weak signal.

Other than the conventional endpoint PCR amplification only needs 25 to 30 cycles of product quantity enough, And real-time fluorescence PCR must detect low to 10 copies of near 40 cycles reaction. The TaqMan PCR requires at least 40 amplification cycles of reaction. The SYBR Green I real-time fluorescent PCR based on the DNA binding dye usually requires amplification 45 cycles for higher sensitivity and identify of non-specific PD. Therefore the real-time fluorescent PCR technology not only possesses the similar non-specification comparing with endpoint PCR but also the dye SYBR Green I real-time PCR couldn't distinguish the specific fragment with non-specific product at same time. All the non-specification also existed in any PCR system, but only the non-specification of exponential amplified PD which was from excess a pair of 3' ends complement primers is a major source of non-specific product that comparable or catch up exponential amplification of target. A pair of excess primers due to the only 4 kinds of base combination has 25% and has 25% complementation on the other hand. So the primer pairs with the 3' end of a small amount of base-pair complementary will cross hybridized and extend in the DNA polymerase PCR condition to form primer-dimer (PD), which used as next template is largely nonspecific amplified by free primers and bound to the DNA dye. The background Ct value (cycle threshold) of PD amplification of the vast majority primer pairs that carefully be optimization design, which 3' end is less complement as possible, be located generally around 30 cycle in real-time PCR experiments without a template based dye SYBR Green I. Even some primers background Ct value is before 25 cycles that located in the Ct value 15-37 cycles of most target quantitative detection range or "gold detection window" and seriously covered the low concentration of molecular targets quantification. Although the primer dimer couldn't emit fluorescence in the TaqMan real time PCR, which the primer dimer problems is actually neglected, but it competitively inhibited 10 fold lower template amplification with same pairs of primer. Therefore sensitivity of TaqMan real time fluorescence PCR is only higher 10 fold one to order magnitude than the SYBR Green I real-time PCR. So far the very few reports of studies and resolve primer problem, current research still focus on the optimization design primer without the reverse complement and execute "hot-start" PCR for suppression of primer 3' end of a few base-pair binding and extension in low temperature before amplification. On account of DNA polymerase immediately starts work when the PCR ingredients regularly put in pool at time. The so-called "hot-start" means the PCR reaction works to start amplification until components controllable releasing after the thermal denature in order to reduce non-specific reaction before PCR. The "hot-start" measures include using heat release of wax packaged magnesium $Mg^{2+}$ ion, the modified suppression of Taq such as the N end missing of KlenTaq B., et al., 2003, Nucleic Acids Res., Vol. 31, No 21:6139-6147), the heat activated Taq with anti Taq antibody (Kellogg D E, al., 1994, Biotechniques 16:1134-1137) and Taq enzyme with inhibited Aptamar (Lin Y, et al., 1997, J. Mol Biol the heat activated primer with four oxidation pentane fixed (Lebedev A V, et al., 2008, Nucleic Acids Res., Vol. 36, No 20: and so on. The non-specific amplification especially PD come from the mispairing extension in the low temperature and as well in the higher annealing temperature of thermal-cycling reaction. The background Ct value of a artificial "hot-start" by manually adding a lacking component after denature to the PCR solution, which exactly lack the same component, is delayed 1-3 cycles comparing with un hot start common PCR and has about 32 cycles. And the efficiency of base-pair extension and activity of thermo Taq enzyme is usually low in the low temperature. The higher temperature of thermal cycling is absolutely major reason of PCR non-specific primer-dimer PD amplification. The Hands technique that is most close or similar with this current invention has adopt completely same sequence primers for eliminating of the non-specific PD amplification (Homo-Tag assisted non-dimer system, Brownie J., et al., 1997, Nucleic Acids Res., Vol. 25, No 16: p 3235-3241); And the chimeric DNA, RNA primer (Peleg, O., et al, Applied Enviro Micro-Bio., 2009, Vol. 75, No 19:6393-6398; and PCT: send 2009/004630); The oneself ends pairing of a single strand PD from completely same sequence primers can competitively bind free primers. And the chimeric primer with several RNA bases that cannot effectively be Taq polymerase template realizes the PD inhibition. But they not only inhibit the PD nonspecific, but also do not selectively interfere with the target specific amplification efficiency. The primer dimers amplified through primers 3' base pairing as reciprocal primer and template. There is no intrinsic difference between target amplification by primer and by same primer pairing and amplification. The action is basically parallel, only the extent lighter. Any inhibition to the primer sequence would be no selectively inhibits target specific amplification.

The real time fluorescent PCR "closed tube analysis" in most cases is not real completely closed, there are also cross contamination of PCR products aerial fog pollution. In addition to the capillary tube with screw cap, most of the 0.2 ml PCR test tubes or 96 well plates will be soft and leak in the thermal cycling denature heating time. There will be some aerosol to leak out (squeeze) of the tube cap under the high temperature and high pressure. An aerosol particle could contain $10^5$-$10^6$ amount molecules, which not only are the possible positive target amplicons and also contain high concentration of primer dimer amplification of excess primer pairs in every reaction well. As repeating the same PCR, the leaking pollution can be exponentially amplified again and be accumulated. Then the real-time fluorescent PCR is not start from 0 cycle but from the last end of past PCR cycles, the pollution like snowball grow more and more. To prevent aerosol recontamination of PCR products, the using of substrate dUTP instead of dTTP coupled with uracil-DNA-carbohydrate enzyme (UDG/UNG, U.S. Pat. No. 6,090,553), which is inactivated in later heating cycles, can selectively degrade the aerosol products of contamination in pre-cycling. But the UDG is double-sides sword to specific and nonspecific products, it less effectively degrade too much aerosol in less amount of UDG and over degrade target products in excess amount of UDG enzyme. The moderate amount of UDG which could eliminate small amount of cross contaminated aerosol in optimum temperature before PCR is not enough to stop the PD amplification and delay the background Ct value of SYBR Green I real-time fluorescent PCR in practical work.

In order to overcome the inherent obstacle of false positive of primer dimers PD of SYBR Green I real-time fluorescent PCR is not suitable to clinical testing analysis, as well as the limitation of the existing PD inhibition methods also similarly affect target specific amplification efficiency, this invention "Primer Middle Sequence Interference PCR Method" is on the basis of optimizing a pair of primers according to the conventional primer design principles. The not complement of intermediate domain (ID) of parallel primer pairs, or/and the interference of antisense base oligo-nucleotide complemented with the ID of primers, or/and the intra-primer interference of antisense sequence against ID of primer self, or/and above techniques combination, which maximum break the 3'end outside mis-binding join-force of primer 3'ends less-pairs need to borrowed in thermal cycling, then selectively inhibit the PD amplification without disturbing the target specific amplification efficiency. This invention of real time fluorescence PCR, which plus one end primer heat release and UDG pretreat-dUTP PCR system under the mineral-oil closing, will has not nonspecific primer dimer accumulation that background is a straight baseline in 45 PCR cycles. Multistep protected and closed PCR reaction does not produce the aerial fog or only the aerosol without effective amplification. Just in case the trace leak of PCR aerosol can further effective degrade by UDG enzyme. These integrated measures make sure the nucleic acid amplification test reliable without any false positive reaction.

SUMMARY

In order to avoid the primer dimer (PD) amplification of PCR major non-specifics, this invention referred to the optimization and inhibition of middle domain of primers selectively increase the PCR specification.

"A primer middle sequence interference PCR method", is an improved PCR of selectively inhibiting non-specific amplification through interference of middle sequence called intermediate domain ID to break the primer pairs polymerization, wherein the interference of ID is using natural middle sequence primers with the non-complementary sequence ID included identical same sequence ID to disturb primer dimer PD getting together for PD non-specific amplification within the PCR reaction system and isolating PCR product aerosol glue cross-contamination outside the PCR reaction system, whose common feature is to improve the PCR technology on choosing varieties of technical interferences natural middle sequence primers with the non-complementary sequence or identical ID, adding antisense modified bases oligo-nucleotide complementary with primers ID, antisense modified base intra chimeric-primers complementary with primers ID within the primer molecule, etc., improving the nonspecific fundamental limitations of PCR application without affecting primers specifically combining with target gene and specific amplification efficiency.

"Primer Middle Sequence Interference PCR Method", "A primer middle sequence interference PCR method, wherein the character of middle interference of primers ID is first compares upstream primer sequence with downstream primer sequence parallel at the selected template in the 5' to 3' direction based on current principles of conventional primer design, chooses a pair of primers which have 5-9 non-complement or identical homo-bases alignment in the middle near 4-5 bases far away to 3' end, wherein said the 3' ends of primers also avoid 2 or more than 2 reverse complementary bases as much as possible, and avoid any single base reverse complement at the least end that shall be base C or A, so a series of interferences of middle non-complement or same sequence primer pairs are suitable for gene amplification PCR to reduce primer-dimer PD nonspecific amplification reaction within PCR system in different degrees, significantly enhancing the inhibitory effect of SSB for PCR nonspecific if combined with SSB. Wherein selectively inhibits nonspecific primer dimer-PD amplification by selecting a pair of primers with unmatched or identical homo 6-8 bases in the primer middle, where the middle sequence is unmatched or the identical bases in the middle sequence is insufficient, an artificial mutated base should be introduced into the ID of primer at unmatched or identical 5'/left side to add a unmatched base or identical base, or where the middle sequence have one base difference, should introduced an artificial mutation to become unmatched or identical, if the unmatched or identical 5'/left side is inappropriate, bases near 3'/right side of the ID shall be selected and mutated, a RNA base/2-F RNA modified base shall be introduced in said unmatched or identical sequence in ID to increase negative charge repulsion, so as to slightly enhance inhibition on nonspecific primer dimer-PD amplification; the 2nd, 3rd bases counting backwards from 3' end of primer pairs shall avert GC/CG sequence (CG hairpin structure); even GC/CG sequence (CG hairpin structure) on the 2nd, 3rd bases counting backwards from 3' end of single primer will aggravate nonspecific primer dimer-PD amplification.

"Primer Middle Sequence Interference PCR Method", is executed by antisense sequence against ID, wherein the antisense oligo-nucleotide As Oligo complemented with primer ID binds competitively primer and selectively interferes the binding between the primers, and the chemical modified "antisense" base sequence with 5-11bases closed-end neither be used as a PCR template nor primer, which only retains binding function, can competitively binds primer ID to disturb polymerization between primers, wherein said the interference of primer ID As Oligo does not affects the specific binding between primer and target gene and specific amplification efficiency, only selectively reduces optimized primer PCR primer-dimer PD nonspecific amplification when it is applied independently for PCR of optimized primers based on conventional design principles, the interference of primer ID As Oligo also can applies to solid phase primers-release hot start PCR. Wherein the 6-10 bases of antisense sequence are include the 2'-O-Methyl (OMe) RNA, 2'-O-methoxy-Ethyl (MOE) RNA, 2'-Amino-RNA, 2'-Fluoro-RNA, 2'-O, 4'-C-methylene bridge RNA (lock nucleic acid, LNA), and PNA (peptide nucleic acid), Morpholino, N3'→N5' Phosphor-amidate, etc., which 1-8 modified bases can be interval by normal bases, setting modified base at 3' end to terminate extension or 3' end hydroxyl closed.

"Primer Middle Sequence Interference PCR Method", includes the interference of middle ID intra primer molecules, the antisense nucleotide sequence against ID is connected to the side of 5' end to form chimeric primer whose 3' end a specific target binding sequence and 5' end contains antisense base sequence intra molecules, the 5' end of chimeric can fold and forms binding inhibitory with the primer ID itself, by selecting 5-7bases antisense strand sequence from one or pairs of primer ID, and adding to the 5' end of target template primer in the 5'-3' direction, chemically synthesizes a primer which added 5-7 antisense bases complementary with ID sequence itself, wherein said the interference intra primer molecules can significantly reduce primer dimers PD nonspecific amplification of optimized primers based on conventional design principles within system when it is applied independently for PCR, applies to the primer that does not have middle non-complement or same identical ID, such as the primer of detect point mutation. Wherein interference on primer intra by fold of 5' antisense sequence against ID sequence can be combined with fluorescence labeled primer PCR and multi-fluorescence primer PCR, primer with intermolecular fold on one end can be labeled fluorescent reporter and fluorescent quencher, e.g., the 3rd base or some certain base of one side primer labeled by reporter 6-FAM-dT, Cy3-dT and its 5' end marked by quencher dabcyl or use 5' dG quenching base or sequence, primer on another end is normal, vice versa, the 3rd base to some certain base counting backwards from 3' end is labeled with fluorescent quencher, and its 5' is labeled with fluorescent reporter of various wavelength; quencher shall be far away from reporter on primers, one or multi-channel real time primer fluorescence PCR can be conducted on multi wavelength fluorescence PCR instrument by using multi-pairs of the intermolecular fold primers labeled with fluorescent reporter of various wavelength.

According to "Primer Middle Sequence Interference PCR Method", wherein PCR solution is sealed by mineral oil or white mineral oil, with dTTP replaced by dUTP, meanwhile, uracil-DNA glycosylase (UDG) is added in PCR system to eliminate aerosol glue pollution, the middle interference PCR conduct under the strict closed reaction which is using a PCR ingredient, preferably a primer is dissolved in 20% (w/v) Dextran; heavy solution of 20% Dextran including primers is pre-add to bottom of tube followed by adding PCR compositions included oil sealing in order without Vortex in order to avoid destroying slow release layering, and the residual solution above the oil surface without a primer cannot be amplified, therefore PCR reaction mixed by PCR pre-heating releases heavy primer into solution to start PCR, these combined measures prevent PCR product aerosol glue cross-contamination outside the PCR reaction system. The method prevents aerosol glue contamination from extra of PCR system by combining UDG with dU substrate and using mineral oil sealing, which is applicable for non-repetitive/duplicate tests, on the basis of mineral oil sealing and UDG-dU combination, adopting strategy of PCR ingredients slow-released, i.e PCR ingredient like primers is dissolved in 20% Dextran; PCR ingredient like primers is reversibly bound to solid phase ligand and released under heat to enter reaction solution for starting amplification, which completely eradicates pollution caused by leaked aerosol glue, and is applicable for any clinical diagnosis PCR, and achieve diagnosis level of enzyme immunosorbnent, i.e. false positive rate can be lower than 3%.

According to "Primer Middle Sequence Interference PCR Method", is characterized by a primer-release PCR with a pair of primers ID combine with immobilized As Oligo, nanospheres crosslinked As Oligo adsorbs different primers, and previously adds to array nanoliter-microliter cell reaction chamber whose silicon slide is processed by gel coating, exposure, development, lithography and cleaning, the solid-release primer separates from the cell, and releases when processes hot start, different cells contain different target primers, nanospheres crosslinked As Oligo disturbs the polymerization between primers to inhibit PD, prepares PCR reaction solution without primer, and adds sample DNA, uniformly distributing it all over the chip PCR chamber, then plus mineral oil on the surface of chip to well seal cell, preventing the crosswalk of postponed-release primers, finally silicon chip is covered by a transparent plastic sheet with plastic surface, and the whole silicon chip conducts multiple array real-time fluorescence PCR.

According to "Primer Middle Sequence Interference PCR Method", wherein strategies of designing 6-8 bases of non-complementary sequence or identical sequence on identical direction, antisense oligo-nucleotides and interference on primer intra by fold of 5' antisense sequence in primer ID can be applied to computer programming, to enhance accuracy and efficiency of primers design and selection, and to further perfect said PCR method of interference on primer ID.

Wherein said PCR method about non-complementary sequence or identical sequence of primers' ID, said PCR method about interference on primers by adding As Oligo, and said PCR method about interference of antisense Oligo on intra primer; Said three PCR methods not only can be used separately, but also can be combined to further enhance the effects of inhibition on PD non-specific amplification.

Wherein said PCR method of interference on primers' ID can apply to the gene test or diagnosis kits which include components: extracting and purifying reagents of sample DNA, substrates dNTP include dUTP, DNA polymerase Taq and buffer, fluorescence dye, fluorescence probes, primer pairs, and software for primers design.

DETAILED DESCRIPTION

This invention Primer Middle Sequence Interference PCR Method is the improved PCR that focus on the specific primers optimization of the most important PCR components. Although the specificity depends on the whole primer base sequence, but the base sequence more near primer 3' end is more important, especially the several bases of least significant end. For example, a pair of primers in the 3' end last 1-2 base mutation different with target DNA template can inhibit almost 90%-more than 999% target specific amplification, this feature is often used to test the single nucleotide mutation (SNP) of ARMS technologies (FIG. 1a). While the 1-2 base mutation introduced in the central or 5' end of primer often does not inhibit target specific amplification, the mutation base farther from primer 3' ends, and the influence to PCR is more little. In primer 5' end can even tolerate continuous multiple mutations base sequence without affecting the efficiency of PCR amplification, the molecular cloning method often introduce the restriction enzyme locus sequence in the primer 5' end. But the most important 3' end to the specificity unable independently act as primer, in turn, requires join-force of the central sequence and 5' end sequence on the outside of 3'end. In the similar way, as well the base sequence nearer the 3' end is more important to the non-specificity especially primer dimer (PD) amplification. A pair of primers with more than 3-4 bases reversed complement on the 3' ends of primer pairs can be mutual templates as mutual primers, PCR hybridization, primers extension, lead to highly PD nonspecific amplification, this feature is often used for artificial synthesis of long-chain DNA. The fundamental principle of optimize primer design is to avoid more than 2 bases consecutive complement of 3' terminal, however DNA is only composed of four kinds of bases, and the primer pairs 3' ends 1-2 base complement always meet and is hard to avoid. The binding force of a pair of primers 3' ends 1-2 complementary bases under the condition of PCR thermal cycling is too small, and need to borrow the random base pairing of hydrogen bond force on the outside of primer 3' ends to cross hybridize, extend for PD nonspecific amplification. The primer 5' end continuous couples of bases complement helps to PD amplification is very little, due to the too far distance to important 3' end. So the hydrogen bonding force of multi-bases mis-pairs of middle or intermediate part near 3' end between primer pairs which borrowed by a pair of optimized primers 3' end is major action force; and the hydrogen bonding force of 5' end couples of bases complement that borrowed by optimized primers is secondary assistant. Unlike primer 3' end is first important, middle is second, and 5' end least matter in turn to target specific amplification. After the designed optimize primer pairs eliminate 3' ends non-specific complement, the hydrogen bonding force of mis-pairs of 3' end between primer pairs to PD amplification is already as weak as possible. The PD exponentially amplification must start from a pair of free 3' ends of primers, but the binding force of multi-bases mis-pairs of middle or intermediate part (intermediate domain, ID) near 3' end between optimize primer pairs to PD non-specific amplification is most important determinant factor! Therefore, the primer middle or intermediate part 6-8 bases, which last base is 4-5 base distance far from least 3' end, be defined as Intermediate Domain (ID). The "ID" determines the primer non-specific and is second factor to specific amplification. This invention "A PCR method of middle interference of primers" uses the nature ID interference, or extra adding antisense oligos against ID, or intra primer antisense base interfere ID etc three techniques to furthest selectively eliminate the PD nonspecific amplification without disturbing target specific amplification efficiency.

The description of this invention "Primer Middle Sequence Interference PCR Method" will elaborate in turn from the fluorescent dye SYBR Green I real-time fluorescent quantitative PCR, and the PCR nonspecific complexity, the main possible mechanism and control measures. The real-time fluorescent quantitative PCR using dye SYBR Green I especially without adding templates' background system to verify the degree of nonspecific complexity of primer pairs. And content writing with the SYBR Green I real-time fluorescent PCR technique, main consideration is the SYBR Green I real-time is simple, sensitive and accurate, not only more visually nonspecific amplification reflects the reaction of primers, and write straightforward, doesn't mean the present invention is limited to SYBR Green I real-time fluorescent quantitative PCR technique. This invention can be applied to contain/with various primers PCR technology, including the sorts of DNA/RNA amplification technology, various thermal cycle/constant temperature solution chain PCR technology, the kinds of fluorescent dye/fluorescent probe PCR technology, the kinds of quantitative/mutation detection of PCR technology, and the kinds of multiple PCR/array technology, and so on. To understanding accurately the contents of the invention description at the point, a series of technical features of this invention description will make an accurate definition. The key word:

The "primer" is a target-specific (usually conserved) sequence of oligonucleotides, which length is 18-25 nucleotide bases single-strand DNA, includes the forward primer (F) take template upstream 5' end a fragment of sense chain; the reward primer (R) select template downstream 3' end a fragment of antisense chain; It is also name as 5'/3' primer, one side/one end primer, another primer.

The "Intermediate Domain (ID)" is the primer middle or intermediate part 6-8 bases, which last base is 4-5 base distance far from the least 3' end of primer; The "ID" determines the primer nonspecific and is second factor to specific amplification.

The "template" is a fragment of target gene which be amplified by PCR; It is sometimes call the nonspecific amplification DNA fragment as template or another primer as amplification template.

The "reverse complement of base" is base pairing or binding between template that in 3'-5' direction and primer that in 5'-3' direction, the base pairing is G:C or A:T match, it is similar to nature DNA double-strand complement.

The "parallel complement" is the "complement in same direction" that relative to the "reverse complement", the primer with primer could bind both in the same 5'-3' direction by using G:C or A:T base pair or base miss-paring.

The "homology or same sequence" is base sequence highly similarity comparing two fragment genes, the homology means the two fragment genes originating from the same kinds of species, the same sequence is complete same base in order between two genes.

The "no complement of sequence" is a continuous base array not match comparing two kinds of fragment genes, the moreover there is not complementary hydrogen bond of wrong base paring between purine pair with purine, pyridine with pyridine.

The "optimization primers" is based on the current principle of primer design which reduce 3' ends non-specific complement base between primer pairs as less as possible, carefully select a pair of primers that has the continuous no complement or same sequence ID of middle sequence between primer pairs.

The "primer dimer (PD)" is the oligo-nucleotide dimer of exponentially amplification from a pair of excess primers which less 1-2 bases complement on the 3' ends of primer pairs can be mutual templates as mutual primers to start extend and form the primer dimer strand as next cycle template, following PCR hybridization, extension by free primers, lead to primer dimer double strands nonspecific amplification.

The "background Ct value or Blank PCR": Blank PCR means all components intact SYBR Green I real-time fluorescence PCR except without adding target template to verify the nonspecific blank. The cycle numbers when the fluorescence intensity of the no target PCR amplification curve reached to threshold of logarithmic phase is the background Ct value, the ideal always baseline of reaction is called no Ct value without fluorescence intensity amplification.

The "antisense oligo-nucleotide" is a fragment of the oligo-nucleotides, which compose of partial or all antisense bases. The fragments of chemical modified "antisense" base that retain only base combining function and cannot recognized by DNA polymerase can neither as PCR template nor as amplification primer. Therefore the "dead" antisense oligomers can competitively combine with the DNA strand for the interference DNA function such as primer nonspecific amplification.

The target genes are amplified by PCR in the exponential pattern, that is to say, after each thermo cycle of PCR, the molecules will be doubled in numbers. The fluorescent dye SYBR Green I (SG) real time PCR based on the ordinary PCR method monitor continually changing of fluorescence value to cycle numbers by introducing DNA fluorescent dye. The SYBR Green I is a kind of double strands binding dye which can bind in the DNA helix minor groove, the fluorescence intensity of association DNA with SG dye enhance hundreds fold comparing with quenched free state of SG dye, and can report synchronously the product contents of real-time PCR amplification. The first few cycles fluorescence signal of amplification curve that is almost unchanged is called as the baseline. The Ct (cycle threshold) is the number of cycles products amplify to a point of log-phase or required for the fluorescence signal to cross the threshold which is defined as fluorescence signal of mean and SD (standard deviation) 10 fold than baseline. If the more amount of starting target sample, the fewer cycle of amplification needed to cross threshold. On the contrary, fewer amount of starting target, more cycle of PCR needed. The quantitative relationship between amount of starting target sample and cycle number of PCR product threshold is the inverted log. Theoretically PCR amplification efficiency is 100%, the amount of starting target is diluted fold, the cycle number of PCR will need one more cycle or one more Ct value. The amount of starting target is diluted 10 the cycle number of PCR will need more 3.3 Ct value to cross identical threshold. As oppose to the known copies of DNA standard, it can test amount DNA of sample comparing the standard quantitative curve. For instance, the series of Ct value the standard curve by SYBR Green I real-time fluorescent PCR is respectively around 16, 19.3, 22.6, 26, 29.5, 33, and 37, which is corresponding to copy number of standard DNA about $10^7$, $10^6$, $10^5$, $10^4$, $10^3$, $10^2$, and 10' range. Actually the amplification efficiency of SYBR Green I real-time fluorescent PCR is almost to 100% as detecting in the point of early log-phase. Therefore, as long as get the Ct values of the sample under PCR test, it can check Ct value from amplification curve comparing standard and calculate the initial copy numbers of samples.

Due to the exponential amplification of PCR technology is extremely sensitive, in selective amplification specific molecular targets at the same time, the PCR system also bring the serious exponentially nonspecific amplification outside the target molecules. The background fluorescence of blank SYBR Green I real-time fluorescence PCR without adding target DNA template must be theoretically a baseline that should not be a logarithmic growth of fluorescence signal. However, the hundreds of primer pairs, which optimize designed by current primer design principles was carefully tested by the SYBR Green I real-time fluorescence PCR. The background Ct value of almost primer pairs is around 30 cycle. About the conventional endpoint PCR that is not fluorescence quantitative amplification, the PCR product of routine 30 cycles reaction already enough, just steer clear of most nonspecific amplification. But the quantitative PCR detection range of general SYBR Green I real-time fluorescent quantitative PCR at least need to 40 cycle reaction, had better add extra cycles to test non specific amplification of false positive reactions. And the background Ct value 30 cycle of most primer pairs is similarly equal to the positive Ct value of thousands copy/per PCR, not only in the "gold" detection range of real-time fluorescent quantitative PCR, also give the serious false positive reactions of nonspecific amplification. The real-time fluorescent quantitative PCR of TaqMan probe is generally not bind or bypass to the primer dimer due to adding one target specific probe, its nospecific background Ct value as delayed one to two order of magnitude as about 37-39 cycle. The false positive reactions of TaqMan PCR can reach the affordable background. But the primer dimer also inhibit the lower one order of magnitude target amplification.

The PCR nonspecific amplification is unusually complicated, sometimes a kind of pollution is solved, the other reason nonspecific still exists interference, makes the biological countless efforts still did not find the key problem of PCR pollution and PCR nonspecific fundamental and effective solution since PCR developed more than 20 years and has authorized more than the thousands patent during PCR.

The careful analysis of the basic source of pollution has two ways, one is a template cross contamination from outside the system, but more important way is generating of nonspecific amplification intra PCR system. The first way: the pollution from outside is mainly the PCR products of aerosol glue recontamination and the positive sample DNA cross contamination which is similar with regular test such as the positive cross contamination of ELISA analysis. The cross contamination of positive samples of low content and larger molecules comparing PCR aerosol pollute is quite limited under the condition of strict clinical laboratory. And the real-time PCR "closed tube analysis" in most cases is not completely closed. Mostly the problem of amplification product aerial fog pollution was ignored. Excepting the screw cap capillary tube, the most of the 0.2 ml PCR test tubes or 96 well plates is at 95 heat denature, repeated under high temperature and high pressure. There will be some aerosol glue overflow out of the tube cover. An aerosol particles containing $5 \times 10^6$ molecules copy, the aerosol glue not only contain the positive target molecules, and more of primer dimer amplification or primer-probe amplification between excess primers and probes. Moreover, every test reaction tube or well produce primer dimers of nonspecific amplification. As repeating the same PCR, leakage of pollutants can be repeatedly index amplification, accumulation, then real-time fluorescent PCR is not cycle start from 0 but from the last end of PCR cycle number, pollutants snowball is piling up. The guarantee close of PCR reaction is premise condition of the success. The second way: the more serious pollute is generating of nonspecific amplification intra PCR system which is the miss pairing of excess primer 3' end bind to nonspecific templates that be irrelevant with target. primer design should consider all the nucleic acid DNA in sample besides the target genes, which may cross hybrid binding. Any continuous base complement long sequence that paired to primer 3' end must be excluded from the primer design So even a small amount hybrids of individual few bases with only one end primer lead to linear increase, the nonspecific amplification is not the focus. It is not easy to produce a pair of primers just right in adjacent of a gene of irrelevant target exponentially amplification. Also because of the dispersion and low concentration of target irrelevant DNA, the nonspecific amplification between specific primer and random irrelevant template need much more cycles to produce enough products linear amplification. The excess primer 3' end intra PCR system still mainly base on another excessive primer sequence as nonspecific template. The amplification of one pimer middle sequence or 5' end sequence paired with another primer free 3' end as before linear increasing, so that exponentially amplification of nonspecific PD must start from the free 3' ends of the primer pairs. A pair of primers with couple bases reversed complement on the 3' ends of primer pairs can be mutual as mutual primers, the primer 3' end extends to form a double strand PD of primers 3' end to 3' end two primers polymer under the DNA polymerase catalysis. The formed double strands PD act as next cycle template, and further are amplified by high concentration of free primer to produce typical primer dimer (Primer-Dimer, PD) nonspecific contamination. Although only one primer 3' end extension is just linear increasing, but the extended one primer on the subsequent thermal cycling will further aggravates the probability of primer dimers (PD) nonspecific amplification. Therefore, the primer dimer (PD) amplification is the most fundamental sources and major contradiction of the nonspecific contamination intra PCR system. The contamination of PCR after solved the primer dimer (PD) problem would be solved.

The numbers of a pair of primers is usually by using 5 μM/L or 5 μM/μl concentration (terminal concentration of reaction 0.1 μM/L or 0.1 μM/μl), converted the molecules of $5 \times 6.02 \times 10^{17}$/L or $5 \times 6.02 \times 10^{11}$/μl, about $10^{12}$ numbers of primers is far much to the template concentration, even more than thousands time to the most number of PCR end amplification product. The optimum 3-5 μM/L or 3-5 μM/μl concentration ability effectively amplify the target, otherwise higher than 5 μM/μl concentration will result in even more PD amplification and accumulation. The only four bases of permutation and combination of a pair of primers is more than 25% of natural homologous, also has 25% of mutual complementation, so too much of a pair of primers 3' ends where are complementary to each other mutual hybridization produce dimer followed PD nonspecific amplification by PCR. The PD formation is generally with the help of the multiple reverse complementary base pairing of 3' ends of primers, which be mutual template, mutual primer to start form the dimers, the multiple continuous reverse complementary base between primers 3' ends can be avoid by conventional primer design methods. But there are or two reverse complementary base pair between primers 3' ends is inevitable due to the arrangement of only G, C, A, T four kinds of bases. Meanwhile a single strand of DNA has certain flexibility, a pair of primers with 3' end fewer base can curve and borrow the join force of multi intermittent base pairing outside 3' end to bind each other and extend some sequence. The extended primer hybrids now has more synthesized base for more stable pairing between primers 3' ends to produce the primer dimer. The PD double strands once formed and immediately as template be amplified by free primers bound with SYBR Green I dye. In the nonspecific amplification of the background experiment base on SYBR Green I real time fluorescence PCR without adding the template, the primer dimer nonspecific amplification is generally around the 30 cycle that start to enter the logarithmic phase (FIG. 4), nonspecific amplification get serious worse. The product of 30 thermal cycles amplification is usually enough, most of the PCR can be over. If there is no primer dimer to start form and pollution was not repeatedly amplified, the nonspecific amplification of most PCR within 30 thermal cycle is not that big. vast majority of a pair of primers produce dimer background Ct value is generally around 30-31 cycles. The real time fluorescent PCR 30-38 cycle is still corresponded to target in the 10000-10 copies of target molecule detection range of test window". Thus the nonspecific amplification of PD seriously interferes with the low concentration of target molecules precisely accurate quantitative test and definite diagnosis of weak positive specimen. The mechanism of primers to form dimer in theory is primer pairs hybridization part catalysis with thermal polymerase in lower hybridize temperature Tm of primer pairs that could has higher Tm, however the absolute "hot start" PCR of optimized design primers merely delay background Ct value later 1-3 cycle number, at most to 33 cycle around. The absolute "hot start" refers to the "manual adding" that replace to "hot releasing" of pre-deleted ingredients of PCR to start act after the thermal denature. When the length and Tm of primer is a constant, the increasing of annealing temperature sharply reduce amplification efficiency including PD amplification; the decreasing of annealing temperature slightly reduce target amplification efficiency and obviously enhance PD amplification; but annealing below 40 temperature also sharply reduce amplification efficiency including PD amplification in thermal polymerase condition. Therefore, the binding force of a pair of primer 3' end fewer pairing base couldn't support the thermal cycling condition alone, the "hot start" should quite effective if primer 3' end pairing is alone major factor to PD. The cause formation of primer dimer mostly should start from complement pairing of primer 3' end fewer pairing base work together with multi discontinuous pairing base outside 3' end binding force. The join force stable promotes hybridization between primer pairs under the thermal cycling to produce dimer. It is also possible that annealing temperature speed the 3' end of molecular collision by thermal motion, as well as the instantaneous bind and one to two bases randomly each time by Taq enzyme catalysis. Not find PD theoretically the reasons or is difficult to fundamentally solve the problem of PD.

The PCR system for nucleic acid amplification such as primer, substrate, enzyme and corresponding buffer, and magnesium $Mg^{2+}$ ion optimization is result of long-term experiment, allowed the range is very narrow. The concentration of the simple change of primer to PD nonspecific amplification and target specific amplification effects are basically parallel. The effect experiments which test hundreds of chemical and biological reagents by adding to PCR system has conduct near one thousand time in this invention, the basic influence is also parallel effect. The inhibition of the non-specific reaction also reduces the specific efficiency at same time. For instance, the using half of the concentration of the routine primer amount can significantly reduce the level of primer dimer (PD) formation, but also parallel sharply reduce the efficiency of specific target template amplification even cannot PCR. The effect by changing the polymerase, the corresponding buffer and magnesium $Mg^{2+}$ ion, potassium $K^{2+}$ ion is basic same result. But for amplification of 100-200 bp short templates, the TaqMan probe real-time fluorescence PCR by lower using the half of the regular dNTP substrate concentration can improve the partial amplification efficiency. The nucleic acid amplification techniques often use a variety of PCR enhancing reagents, such as Betaine, Dimethyl sulfoxide (DMSO), Forma/Acetyl amide, Dimethyl formamide (DMF) increase the amplification efficiency as promote about 1-2 Ct value. These reagents increase the amplification efficiency by promoting the desmolysis of the template secondary structure, also parallel increase PD background Ct value. To find a solution of PCR primer dimer nonspecific amplification, the key measures are must also from the acting mechanism of PCR core component-primer to find, and from the differentiation of primers pairing with specific target and non-specific hybridization to explore.

In order to explore the mechanism of the PCR primer dimers nonspecific amplification, a variety of SYBR Green I real-time fluorescence PCR without adding DNA template proceed the background experiment to verify the situation of primer dimer nonspecific amplification, find out the common regularity. If a about 20-30 bases of nature gene single strand fragment with a another any sequence 20-30 bases fragment compose as a pair of primers, which background Ct value of primer pairs of SYBR Green I real-time fluorescence PCR without adding template could be a broad ranges from 6-7 cycle 40-45 cycle base on their sequence, even more broadly than positive sample detection range. Only the optimized primers background Ct value of PD nonspecific amplification after carefully design by the primer design principles is at around 30 cycles. For example a pair of primers A and B, which the least 3' end 3-5 base of primer A is continuous base reverse complement with the terminal of 3' end of another primer B, the background Ct value of PD nonspecific amplification is serious that just a few Ct number to exponentially amplification. The surprising thing is a pair of primer A and B, which 4-6 bases at primer A 3' end are continuous base reverse complement with the middle sequence of another primer B, where end of B is not complement with the middle sequence of A, the background Ct value of PD nonspecific amplification is 30-non cycles (FIG. 1d). If a pair of primer A and B, which only A primer 3' end 7 base is continuous base reverse complement with the 5' end sequence of another B primer, the background Ct value of PD nonspecific amplification is still 35-non cycles (FIG. 1e). These kind of longer continuous base reverse complement near 5' end of primer by borrow join force from outside 5' end can form stable partial double-strands which baseline is little higher. Therefore a pair of primers should both have primer 3' ends reverse complementary each other to produce PD amplification, and only one side primer end reverse complementary is linearly increasing that is not the main cause of PD amplification. If a fragment of 4-6 base continuous reverse complementary each other is both in the middle part of a pair of primers, the background Ct value of PD nonspecific amplification is 32-35 cycles (FIG. 1b). The continuous reverse complementary in the middle of primers has mild inhibition instead promoting PD nonspecific amplification. If the continuous reverse complementary 6-12 bases are located in a pair of primers 5' end terminal, the background Ct value is around 30 Ct cycles (FIG. 1c), which baseline is increased. Thus it can rule out a pair of primers regardless of the 5' end or middle reverse continuous complementary is obviously not the cause of PD nonspecific amplification. Of course these typical sequences of long fragment of the reverse complementary do not become a primer design options, just to explore mechanism of primer dimer may provide clues. as long fragment of the reverse complementary could not have caused PD and a few bases complementary are not. to the current primer design principles or primer design software, selective most optimize primers without 3' ends reverse complementary of 3 bases or more than 3 bases have general PD nonspecific amplification of Ct 30 cycle, which located in the positive quantitative template DNA detection range, and seriously interfere with the quantitative determination of low concentration of target molecules, and cause the weak false positive reactions. And the a pair of approximate 100% primers which is equal to the same single primer of double amount is very special case, the background Ct value of the vast majority of single primers of double amount is a baseline without any amplification. This enlightens us a lot to further test background Ct of double amount of single primer at even 100 times thermal cycling is still a baseline. But the primer pairs one reversed complete same sequence with another lost the inhibition to PD. How much or where similarity of a pair of primers can reduce the PD extent? These propose a train of thought for us!

Under the Taq polymerase without proof reading catalysis, the nucleic acid synthesis should be from the right pairs of primer 3' end to extend, the base pairing of sequence outside primer 3' end is help for primers stable pairing of annealing on the corresponding primers Tm value. So first of all, it is necessary that the primer sequence was divided into the 3' end of 4-5 base Primer-Domain (PD) area, the middle of 6-8 base Intermediate-Domain or Identical-Domain (ID) area, and the 5' end of 5-14 base Assistant-Domain (AD) area, a total of three functional areas. These function area bases are farther distance away from primer 3' end gradually less important for nucleic acid synthesis. A pair of primers in the regular PCR hot start, thermal cycling conditions, needs their 3' end multiple bases reverse complementary to bind and hybridize in the primer annealing Tm temperature, further PD nonspecific amplification. Current primer design principles and design software basically rule out the possible of continuous multiple bases reverse complementary of a pair of primers, design especially focused on the primer 3' end optimization as much as possible. But it can't optimize the whole sequence of all the full-length primers. The primer 3' end fewer 1-2bases pairing of PD nonspecific amplification still needs 3' end fewer base right pairing to initiate, but strength has been greatly decreased, and can't be the independent/main force of PD nonspecific amplification, and needs to borrow join force of the neighboring intermediate domain (ID) sequences to help the primer hybridization. The intermediate domain (ID) sequence to the PD nonspecific amplification is transformed into the main dominant factors. So the competition of intermediate domain (ID) sequence of 3' end optimized primer paired with specific target and with nonspecific another primer quietly appears the difference, the primer 3' end is still first important to target specific role, and second factor or less helpful to the optimization primers of 3' end residual 1-2bases pairing. The situation of nonspecific binding has fundamental changed, the intermediate domain (ID) of primer become a decisive main strength to the PD nonspecific amplification of optimized primers. The lower binding force of the intermediate domain (ID) of primer and/or interfere with the intermediate domain (ID) of primer which has little effect on the target specificity and more act on the PD nonspecific effects, can selectively inhibit PD nonspecific amplification without affecting the target specific amplification.

Of course, it is better to go as far as possible back to PD molecular or biochemical mechanism of nonspecific problem. But PD formation mechanism is extremely complex, and the PD may be a variety of mechanisms coexist. According to the variety of primer dimers PD product sequencing analysis, most of the PD is to insert 1-5 base between a of primers 3' end, a part of it is missing 1-3 base, rarely is to insert a long sequence, none of it is missing a long sequence, part sequence of inserted or missing is the continuous bases of primer sequence, irregularly. Conventional designing ruled out 3 or more than 3 continuous reverse complementary bases above, a pair of primers of only four bases to arrange or two complementary base at 3' end is inevitable, and primer 3' end of a few 1-2 complementary base on PCR must lends adjacent base pairing to stable matching for combing each other in the annealing or thermal cycling conditions. The of polymerase catalytic DNA synthesis is start primer 3' end along the 5' to 3' direction of primer strand which reverse hybridized with template, the primer dimers PD nonspecific amplification also follow the same principle of DNA synthesis/principles. Thus reason out that PD nonspecific amplification mechanism of several possible: (1) first of all, A of primers one primer 3' end search another primer of reverse right pairs outside 3' end as more base as possible by G-C and A-T pairing principle (see attached FIG. 2c, d). If the case of only one primer 3' end has stable binding on PCR followed only one 3' end extension is linear increasing. If the case of both primer 3' ends have pairing which depends two situations, the distance of more than 3 bases between primers ends pairing that lack join force is hard PD amplification. If the case of distance of less than 3 bases between primers ends pairing will belong to next situation. (2) A pair of primers F&R, one F primer 3' end 1-2 base reverse pair with another R primer sequence near 3' end, vice versa, both primer 3' ends of distance between interval less than 3 bases tend to form join force (FIG. 2b), similar to a pair of primers of multiple base reverse pairing on 3' ends of PD nonspecific amplification. (3) A pair of primers F&R, F primer 3' end 2 base reverse pair with sequence bias 3' end of R primer, but R 3' end only 1-2 base pairing, the less interval of ends pairing is close to (2), the interval is hard to form join force (FIG. 2c). The occasionally only extended F 3' end is also linear increasing. (4) A pair primers F&R, one F primer 3' end fewer base reverse pair with 5' end sequence of another R primer and R 3' end only mis-pairing with sequence of F primer is too far join together to PD amplification (FIG. 2d), If F primer 3' end has long sequence which reverse pair with 5' end of another R primer couldn't form PD. (5) Last is tricky case, a pair of primers, one primer 3' end 2 base reverse pair binds with another primer 3' end 2 base, which binding force of a pair of primers 3' ends complementary bases in the PCR thermal cycling is too weak, and need to borrow other base pairing force on the outside of primer 3' ends to hybridize, extend for PD. But how two of "dangling" single strand of outside 3' end, when only a pair of primers 3' ends reverse binding, to form lendable reverse complementary pairing double-strands of outside 3' end? It is only two primers parallel closer and both 3' ends are distorted. The reverse pairing of reflexed 3' ends after 5' to 3' parallel matching of outside 3' end of primers is start annealing and extending for PD amplification. Any primer 3' end fewer base binding all needs the pairing join force of outside of 3' end especially ID of primer.

The nucleic acid DNA synthesis has directivity, but base hydrogen bonding is no choice of direction, like PNA peptide nucleic acid which is peptide backbone of repeating N-(2-aminoethyl)-glycine units linked by peptide bonds. Actually it is not acids without phosphoric acid. The PNA has higher strength and greater specificity in two directions. Thus PNA neutral peptide backbone without negatively charge of phosphate group, and nucleic acid hybridization affinity with each base Tm value is higher than 1-2° C., in another word, Each phosphate group deduct each base Tm value 1-2° C. That is inferred the terminal base of primer without phosphate group Tm value is also higher than 1-2° C. Due to the flexibility of base 300-360 freedom of DNA, more freedom of the end base of primer. A pair of primers near 3' end fewer bases are distorted and reflex to form reverse right pairing which work together with the 5' to 3' parallel bases mis-pairing outside of 3' end. The higher Tm value 1-2° C. and more freedom of the end base, i.e. the Watson, G: C and A: T base pair, the Wobble G: T and A: C pair, and other G: G, C: T, T: T, A: A, G: A and so on mismatch pair conformation let the primer 3' ends stable annealing extending during thermal cycle (FIG. 2a). The blank SYBR Green I real-time fluorescence PCR of a pair of approximate 100% homology primers or double amount of majority of single primer is baseline without growing fluorescence Ct value within the 100 thermal cycle of PCR. The highly homology or whole complete same sequence of a pair of primers between parallel to 5' to 3' sequence matches let above (5) case lost base complement to inhibit PD; and a more than 10 base parallel ID pairing of antisense oligonucleotides can effectively inhibit PD; both together clearly support the PD nonspecific amplification mechanism. The fluorescence dye SYBR Green I and polymerase Taq without proof reading could further increase the binding force or hybrid Tm values of fewer base pairing. In short, no matter what the mechanism of PD, the primer Intermediate Domain (ID) interference can scattered or destroy all kinds of possible mechanism of PD near 3' end of base pairing force.

The least end base of primers specially has the different performance of the nucleic acid bases inside the sequence of DNA double strands. Every base inside the sequence has both side adjacent bases affection and space limitation of phosphate backbone chain. However the least end base of primers 3' end only has one side effects of adjacent base stacking and negative charge of phosphate. The more freedom and lack phosphate group of primer 3' end result in the primer 3' end easier twisty and easier base mis-pairing. The DNA double helix is right handed, which sugar-phosphate backbone is on outside, the bases pairing with hydrogen bond and maintaining axial base stack is lie in inside of helix. The base pairing strictly by Watson G:C, A:T pair due to the strength and space limitation of helix ensures the accuracy of the DNA replication and maintains genetic stability. Each base pair is rotated ~36°, so ~10 base pairs make a complete turn of 360°. Except the Watson, G: C and A: T base pair, the Wobble G: T and A: C pair, and other G: G, C: T, T: T, A: A, G: A and so on mismatch pair conformation, which also exist in the nature life, has the some stability of similar with normal DNA double helix. In this way, the least end base of a pair of primers 3' end which is half free with only one side of base-stacking and helix space limitation very easily form mis-pair hydrogen bonds in the non-physiological conditions. Of course life already has evolved the proof reading DNA polymerase with 3' exo-nuclease activity for DNA correction. Further in the same way, a pair of primers A & B, one primer A 3' end least $1^{st}$ base reverse pair with $2^{nd}$ base count back of B 3' end to form hydrogen-bond, vice versa, so any pair of primers can form stable primer 3' ends equal 2 bases right pairing. If a pair of primers A & B, F $2^{nd}$ base count back from 3' end right pair with $2^{nd}$ base count back of B 3' end to form hydrogen-bond, plus both primer 3' ends least base wrong pairing, so the complement of $2^{nd}$ base count back from 3' end of primers pairs have stable primer 3' ends equal 3 bases right pairing. If a pair of primers A & B, the $2^{nd}$-$3^{rd}$ bases count back from 3' end right pair with $2^{nd}$-$3^{rd}$ bases count back of R 3' end to form hydrogen-bond, plus both primer 3' ends least base wrong pairing, so the complement of $2^{nd}$-$3^{rd}$ bases count back from 3' end of primers pairs have stable primer 3' ends equal 4 bases right pairing. Therefore the complement of 1-2 bases near least 3' end of a pair of primers could zoom in to 3-4 bases reverse complementary by half free end base. The sequences within 7 bases near 3' end as "primer domain" of a pair of primers which not permitted any reverse complementarity is first important to PCR, especially the complement of $2^{nd}$-$3^{rd}$ bases near 3' end of a pair of primers absolutely is not allowed.

It seems that the current PCR primers design principle also has some limitations of cognitive and application. The current primers design principles are: (1) Select 18 to 25 nucleotide bases of target specificity (conservative) sequence generally, which length difference of upstream and downstream primers is not greater than 3 bases. The Tm value between upstream downstream primers should not greater than 5. Amplification product length is appropriate between 100 to 600 bases. (2) The G and C content should be in 40% to 60%, the four bases equably distributed. Avoid a base repeat four times or more continuous and sequence repeat (hairpin structure), and secondary structure caused by simple sequence repeat. (3) A pair of primers can't have three or more continuous bases that reverse complement each other, especially at the 3' end of the (4) The 3' end especially least end and the second base from end of the primer should be correct and matched with target template. As far as possible make the 3' end of primer to be G or C base, but not for NNGC or NNCG end (so-called hairpin), also can't end for a less specific T base. Based on existing primer design principles, there are certain perceived differences or need to supplement some new 3' end detail principles: (1) The reverse complement of three or more bases of a pair of primers is permitted lay in the 5' end or middle of more than 5 bases from the 3' end of a primer, but absolutely couldn't at the 3' end of a primer. The reverse complement of 5' end or middle of primers will not increases PD nonspecific amplification. (2) The second base from its 3' end of one paired primers can't be G: C or A T base pair, also better avoid to be G: T/A: C pair. (3) The second and the third base of one paired primers' 3' end can't be CG: GC (CG clip), even itself pairing of single primer which contain GC clip of 3' end will increase PD nonspecific amplification. (4) The second and the third base of one primer' 3' end also can't be reverse complement with another primer's third to fifth bases 3' end, especially the CG: GC complementary. (5) It had better choose C or A to be the first base of each primer's 3' end, choose both "easy mismatch" G which has strong hydrogen bonds and poor specificity T with weak hydrogen bonds, more not use repeated double G or T at the end. So such detailed design primers can reduce the common terminal PCR but completely eliminate real-time fluorescence quantitative PCR nonspecific need this invention "A PCR method of interference of primers".

Techniques of "Primer Middle Sequence Interference PCR Method" and Nonspecific Control Measures The middle sequence ID of primers is assistant function to the specific amplification only by stabilizing annealing, and is the decisive power of PD nonspecific amplification for optimization primers that have less than three continuous complementary bases. Take advantage of this differentiation, it choose the natural sequence that less or no parallel complementary ID of primers to reduce the mutual combination, and/or apply antisense nucleic acid short chain which competitive binding with ID in PCR to inhibit the combination between primers. These reduce the primers ID's main effect on PD nonspecific amplification to maximum possible extent without significantly affect the target specific amplification.

(1) The nature middle sequences of primer disturb nonspecifics: First select the nature sequence of parallel 6 to 8 continuous unmatched bases that includes same sequence fragment or the sequence of least unpaired bases in according to 5'-3' parallel comparing between a pair of primers, which is as (Intermediate Domain) ID sequence to placed in the middle or central part near the 3' end of primers. The least unpaired bases or unmatched bases is meaning of base purine to purine, pyridine to pyridine of artificial wrong base-pairing model by the 5'-3' parallel comparing between primer pairs. This lets a pair of primers with unmatched ID or identical ID cannot bind each other in the 5'-3' parallel way. A pair of optimized primers with parallel unmatched bases of ID disperse the join force of the primer 3' end fewer base pair and outside of 3' end, of course cannot provide the "lending force". The nature sequence of parallel continuous base unmatched ID of primers competitively interferes with the PD nonspecific amplification without influence the specificity of the primer hybrid and amplification. The least unpaired bases or unmatched ID is defined as the unmatched bases by comparing of moving in turn forward or backward of one by one base comparing of primers in 5'-3' parallel is as less as possible. The sequences of least unpaired bases of parallel alignment are selected as a pair of primers according to above detail design principles of primers.

The identical ID of same sequence as a special typical case of unmatched ID, a pair of primers whose ID sequence is same 6-8 bases, which make the purine pair with purine and pyridine pair with pyridine in a row during parallel comparison, can significantly interfere the nonspecific amplification of PD. By using a pair of primers that have parallel 6 same bases at ID part, the background Ct value of blank SYBR Green I real-time fluorescent PCR without template is about 40 cycles that delay more than 10 cycles than a pair of general optimized primers. The Ct value of the background PCR for a pair of primers with 8 same bases ID after parallel comparison can even be put off for about 15 cycles. How to choose the parallel continuous identical or not complementary sequence as ID? We usually search the "date base" of genes included target to find the 6-8 bases of closer "inverted repeats" which is in target from the specific or conserved region as primers candidates. A fragment of sense sequences include upstream "repeats" of target are chosen as upstream primers, a fragment of antisense sequences include downstream "inverted repeats" of target are chosen as downstream primers. All candidate primer pairs process a 5' to 3' parallel comparison (Alignment) to search the same sequence of most bases identical ID which unmatched bases by comparing of moving in turns forward or backward is as less as possible. The best one pairs is selected according to above primer detail design principle and followed by test of PCR.

As extreme case of 100% identical sequence of a pair of primers is the double amount of a single primer, the amplification curve of blank SYBR Green I real-time fluorescent PCR of a single primer with double amount is a straight baseline within 100 cycles. But it is no possible find more than 10 bases identical continuous sequence of a pair of primers in nature life. And the more than 10 bases identical continuous sequence ID of a pair of primers also inhibits specific target amplification, which put off target specific Ct value a lot. These proposed a question how about 6-8 bases going? The same bases identical continuous sequence that located at 5' end of a pair of primers has not any effects on PD amplification. Only the 6 to 8 same sequences in the ID of a pair of primers can selectively delayed blank background Ct value of PCR versus much less action at 3' end.

There is some special cases and flexible situation of a natural interference sequence. For example, its rare that ID of a pair of primers has more than 8 bases of non-complementary or identical sequence; even if there exists such primers, it will not be adopted for PCR, since the PCR products based on such primers will bind itself due to high-complementary on two ends of intra single strand, which inhibits/affects amplification efficiency of target specificity. If there are less than 6 continuous bases of parallel identical or unmatched ID of one pair of primers which can't obviously inhibit PD nonspecific amplification, an artificial mutated base is introduced into 5'/left side or 3'/right side of the ID of one primer to increase one more identical or unmatched base with another primer according to Wobble G T and A C matching principle. The base of 5'/left side of the ID is first preferred in order to reduce the effect of primer binding with target as much as possible. The parallel identical or unmatched sequence of ID of primers can introduced artificial chemical modified bases that bring extra negative charge to increase repulsive forces between primers, for example the modified 2-F RNA bases or 5F-dU, 5Br-dU, 8-OH-dG, 8-OH-dA etc to each pair of primers ID can increase repulsion of primer pairs and suppression of PD nonspecific amplification. But it is cannot introduced two 2-F RNA base in each primer otherwise affect the target specific amplification efficiency significantly. Some nonspecific amplification inhibitors of PCR such as Single Strand Binding Protein (SSB) have some mild selective nonspecific inhibition to PD, but the nature interference of ID in this invention combined with these inhibitors as moderate SSB will further promote inhibition of PD nonspecific amplification with mutual synergy. The PCR method of ID continuous unmathed or same sequence of primer is also suitable for Tag label DNA (short Oligo) quantitative fluorescent PCR applying antigen Ag/antibody Ab covalent crosslinking, which conducts indirect quantitative immune PCR of Ag-Ab immune reaction, improving specific performance of the immune fluorescence quantitative PCR. The nature interference of identical ID of primers also can improve the real time fluorescence PCR by using saturated fluorescent dye LC Green and high precision real-time fluorescence PCR instrument (as LightCycler480), to conduct the high-resolution melt analysis, implement the genetic fingerprint identification, and reduce the nonspecific background of LC Green. And it is applied to a series of the isothermal/constant temperature gene amplification technology that doesn't depend on the thermal cycling melting, improving its primer PD nonspecific performance. The isothermal nucleic acid amplification technique is characterized by that the whole processes of amplification reaction (in addition to the initial hybridization step) are at a single temperature, and conduct without special amplification instrument, rather than the PCR reaction that goes through several temperature change cyclic process. This characteristic of the isothermal amplification technology make them greatly simplify the requirements for required instrument, and significantly shorten detecting time, therefore which are suitable for on-site rapid inspection or bedside (point of care) test. More representative applications are: strand displacement amplification SDA, rolling circle amplification RCA, loop-mediated isothermal amplification LAMP, helicase-dependent amplification HDA, nucleic acid sequence-based amplification NASBA, transcription mediated amplification system TAS, etc.

(2) Adding antisense oligo-nucleotides disturb PD: Because the chemical modified "antisense" base sequence neither be used as PCR template nor as amplification primer, these kinds of "dead" antisense oligo-nucleotides, which have merely combinative function and longer than ID, can competitively bind to the nature sequence of ID of primers for selective suppression of nonspecific amplification of PD. And the antisense oligo-nucleotides which specially designed to the primer ID let primer 3' end to keep free, will not affect the specific target-primer hybridization, amplification due to the shorter full primer binding, and selectively inhibit the primer dimer amplification for key ID binding. The varieties of 3' end closed antisense Oligo-nucleotides include the first generation of modified Oligo-nucleotides such as the Methyl-phosphate Oligo-nucleotides and Phosphorothioate Oligo-nucleotides. As they can resist the nuclease hydrolysis, and applied to gene silence/knockout or be used as anti-cancer drugs. But they haven't inhibition for some low fidelity of DNA polymerase as Taq polymerase) which lead to the failure of the "antisense" work. A new generation of antisense oligo-nucleotides, only reserve the combining function and lose the basic performance of being used as amplification templates or primers, include the 2'-0-Methyl (OMe) RNA, 2'-0-methoxy-Ethyl (MOE) RNA, 2'-Amino-RNA, 2'-Fluoro-RNA, 2'-O, 4'-C-methylene bridge RNA (lock nucleic acid, LNA), and PNA (peptide nucleic acid), Morpholino, N3'→N5' Phosphor-amidate, etc. Unlike the 13 to 25 nt (nucleotides) long antisense oligo-nucleotides used in metabolic researches drugs, this invention adopts 6-10 nt/base of antisense oligo-nucleotides with terminal hydroxyl being closed. The sequence antisense oligo-nucleotides is first using the reverse complementary pairing with primers' ID sequences. And the antisense oligomers of parallel complementary with primers' ID sequences need longer 9-14 nt/base oligos due to theirs weaker The optimum-using amount of antisense oligo-nucleotides is about 3 μM-6 μM antisense oligos/5 μM primers, or 2 μM-5 μM antisense oligos/4 μM primers which is slightly inverse ratio to length of antisense oligos. Because of the high price of the antisense bases or oligos, we can use normal bases and antisense base interval strategy to synthesis the chimeric oligo-nucleotides rather than a whole antisense bases of oligo-nucleotides. But it must make sure that the 3' end of oligos being set to a strong antisense base to terminate the extension, and its concentration couldn't be 7-30 μM or less than 3 μM be partial template, otherwise Ct value is reduced by PD non-specific amplification. The chimeric oligo-nucleotides could partial template to increase nonspecific PD and may be easily degraded in sample. As the RNA kind of base can still be as amplification primers, its terminal 3' end hydroxyl groups must be closed by using acetylation, phosphate groups, amino, alkyl, aldehyde, carboxyl, biotin, digoxin, cholesterol, and various kinds of quenching group etc cross-linking. The terminal 3' end also can use the strongest antisense base, or double de-oxygen bases and 3' Inverted dT to inhibit the extension of the closed end. The one-side of primer of antisense oligo binding can enough restrain the nonspecific amplification. If two sets antisense oligos for the primer pairs can further reduce the PD nonspecific background but also bring more complexity and more uncertain non-specifics.

The modified antisense oligo-nucleotide also has some flexibility and exceptions. For first example, the dimer design of two 6-10 nt/base antisense oligo-nucleotides exactly reverse complementary with the primers' ID will enhance the selective suppression of PD nonspecific amplification. The second example, the whole antisense oligo-nucleotide is a wide range of randomly alkylation, acetoxylation, halogen, and oxidative chemical modifications in the circumstances that its base is still under protection as the oligos synthesis, and its terminal hydroxyl group can be closed by the simple hydrogen halide halogenated. The more extent modifications of antisense oligomers will further disturb the primer strands binding and priming. The last example, the solid phase antisense oligo-nucleotide, which the antisense oligos cross-link to the solid phase such as micro-spheres or micro-wells on slides, can also effectively conduct the hot start PCR through thermal denature to release hybrid primer by the solid phase fixed the antisense oligo-nucleotide, and apply to the solid phase "hot-start" PCR, the micro-array PCR. The antisense oligo immobilization. As Oligo crosslinked nanospheres adsorbs different primers, and previously adds to array nanoliter-microliter cell reaction chamber whose silicon slide is processed by gel coating, light-exposure, development, lithography, cleaning, and PEG sealing, the solid-release primer separates from the cell, and releases when processes hot start, different cells contain different target primers, nanospheres crosslinked As Oligo disturbs the polymerization between primers to inhibit PD, prepares PCR reaction solution without primer, and adds sample DNA, uniformly distributing it all over the chip PCR chamber, then plus mineral oil on the surface of chip to well seal cell, preventing the crosswalk of postponed-release primers, finally silicon chip is covered by a transparent plastic sheet with plastic surface, and the whole silicon chip conducts multiple array real-time fluorescence PCR.

(3) Intra primer of antisense bases disturbs PD: The "antisense" sequence matched reversely with ID, which is middle sequence of primer, is connected to 5' end of one or pair of primer to form a base continuous bigger oligo-nucleotide primer. Whole bigger primer composes two parts of 5' end "antisense" sequence and 3' end target primer sequence and called chimeric-primer. "antisense" strand of 5-7 bases of ID region on one or two ends of a pair of primers is added in front of 5' end of primers against target template; chimeric primers with 5-7 "antisense" bases complementary to itself ID sequence is added by chemical synthesis; 5-7 "antisense" bases reversely pairing with itself ID sequence which locates in the front of 5' end of chimeric primers are closely followed by 18-25 bases of specific conventional primers which continuously bind to template. So the "antisense" sequence of the intra chimeric-primer can reverse fold to match and bind to the ID sequence of primer itself. More likely is that the 5' end "antisense" and ID of two chimeric-primers hybrid reversely and combine to other to form two hybrid parts, the force of two "antisense" and ID hybrid parts between them is stronger (FIG. 3) for inhibition each other. One intra molecule both contains target specific binding sequence include ID and 5' end addition "antisense" sequence matched reversely to ID of primer itself. An "antisense" 5 to 7 bases sequence matched reversely to plus to the head of 5' end of target specific primer as whole chimeric-primer is synthesized by chemical methods. The most advantage of "antisense" base intra primer is that "antisense" sequence can be common base without having modified bases except the joint base where is last 3' end base of "antisense" sequence matched with ID. One modified base of last 3' end of "antisense" sequence is enough let 5' part of chimeric-primer losing template action by PD amplification. If by using the identical ID combines with "antisense" base intra primer strategy, the "antisense" sequence matched to ID/middle sequence primer is better move several bases toward 5' end of primer to let antisense-ID 3 bases pair.

The "antisense" sequence intra primer has some special cases and applications, if the case can't find a better identical ID primer such as when detecting point mutation, the "antisense" sequence intra primer strategy of one side or two sides of primers becomes the main options. And this combines with the TaqMan real time fluorescence PCR can further increase the TaqMan real time PCR specificity by reducing primer-probe get together. This technology can be used also in fluorescence marked primers PCR which can be quenched itself. For instance, the selective dT base of ID or middle sequence of the one side chimeric primer labeled by reporter 6-FAM-dT, and its 5' end marked by quencher dabcyl/TAMRA or use 5' dG quenching base or sequence. Vice versa, the selective dT base of ID or middle sequence of the one side chimeric primer labeled by quencher dabcyl/TAMRA-dT, and its 5' end marked by reporter 6-FAM/JOE. A couple of intra "antisense" sequence primers which marked different report dyes can be detected by multi-channel PCR instrument only in one tube at the same time.

Combination of Three Kinds of ID Interference Methods

The nature identical ID sequence of primers disturb non-specifics, Adding antisense oligo-nucleotides disturb PD, and the antisense bases intra primer disturb PD amplification of three kinds of technologies can be effectively used alone, also can assemble combination in order to further enhance the inhibition PD nonspecific amplification effect.

(1) The combination of the nature middle sequences of primer disturb non-specifics with adding antisense oligo-nucleotides disturb PD: First all, the nature identical ID sequences of primers disturbing non-specifics is the basic measure to every other PD inhibition technologies, which action usually is very limited without the key optimization primers. The antisense oligos ID interference efficiency also depend on the optimization primers sequences, especially ID or middle sequences of primer. The antisense oligos alone only put off background Ct value of blank real time PCR a couple cycles. But the combination of two using the nature identical ID method and adding antisense oligos of ID will further put off the blank Ct value of lonely identical ID method to extra more than several cycles. They have mutual cooperate actions. If the combination of two methods only using one side of primer which is usually enough, the sequence of antisense oligo-nucleotides is longer than ID bases, and longer base first put in the 5' end side of one primer ID sequence other in 3' end side. This joint interference technology can then combine with the fluorescent dyes, the fluorescent probe PCR, also can then combine with the product quenching PCR, in contrast to the conventional technical route about PCR product producing fluorescence, the fluorescence labeled primers are quenched through product fluorescence, in one of primer pairs with ID unmatched or same sequence, one side primer 5' end can use 5 methyl isopropyl cytosine (iso-dC) mark reporter dye, meanwhile the other side primer ID adds antisense Oligo to strengthen interference, quenching PCR products penetrate into PCR through the specific pairing of the dabcyl labeled isoguanine (iso-dG) substrate, generating the real-time fluorescent quantitative PCR and multiple real-time fluorescent PCR of amplification products fluorescence quenching.

(2) The combination of the nature middle sequences of primer disturb non-specifics with Intra primer of antisense bases disturbs PD:

When using the combination of nature identical ID of 6-8 bases with the antisense bases intra primer interference, "antisense" Oligo on 5' end of primers adopts antisense sequence of 5-7 bases on the edge between its ID and 5' end region; ID adopts 3 bases at most, so as to avoid that "antisense" Oligo on 5' end of one primer binds to identical sequence on ID the other primer by matching, which makes non-specificity of system more complicated. On the basis of that a pair of with ID of 6-8 bases of non-complementary/identical sequence reduces binding capacity of bases on its ID or interferes binding of bases on its ID, "antisense" Oligo on 5' end of one or two side of primers is combined to enhance ID and primers intra binding, and greatly inhibits PD non-specific amplification in PCR system on condition that its 3' end not significantly affect target specific amplification. This joint interference technology also can combine with the dyes, the fluorescent probe, and the product quenching PCR. The nature identical ID method combines with the marked "antisense" bases intra primers, such as the selective dT base of ID or middle sequence of the one side chimeric primer labeled by reporter 6-FAM-dT, and its 5' end marked by quencher dabcyl/TAMRA or use 5' dG quenching base or sequence. Vice versa, the selective dT base of ID or middle sequence of the one side chimeric primer labeled by quencher dabcyl/TAMRA-dT, and its 5' end marked by reporter 6-FAM/JOE. A couple of intra "antisense" sequence primers which marked different report dyes can conducts one or multi-channel real time primer fluorescence PCR. This also can combine with the product quenching PCR, intra "antisense" primer 5' end can use 5 methyl isopropyl cytosine (iso-dC) label reporter dye, the PCR products quenching through the dabcyl labeled isoguanine (iso-dG) substrate penetrate into PCR reaction by specific pairing of the labeled iso-dG substrate, generating the real-time fluorescent quantitative PCR and multiple fluorescent PCR.

(3) The combination of adding antisense Oligo-nucleotides disturb PD with Intra primer of antisense bases disturbs PD: The "antisense" sequence intra primer can use one side primer or two sides of primers two strategies. And the adding antisense Oligo method is not necessary to use two sides of primers strategy, but it is better the "antisense" sequence intra primer use one side primer and the adding antisense Oligo method use another side of primer. This combination of two antisense Oligo methods is same mechanism action and less synergy. The combination of adding antisense Oligo with antisense bases intra primer strategy without the nature identical ID has some extent of action to inhibit PD amplification. This joint interference technology also can combine with the fluorescent dyes, the fluorescent probe, and the product quenching PCR. The nature identical ID method combines with the fluorescence marked "antisense" bases intra primers, such as the selective dT base of ID or middle sequence of the one side chimeric primer labeled by reporter 6-FAM-dT, and its 5' end marked by quencher dabcyl or use 5' dG quenching base or sequence. Vice versa, This also can combine with the product quenching PCR, intra "antisense" primer 5' end can use 5 methyl isopropyl cytosine (iso-dC) label reporter dye, the PCR products quenching through the dabcyl labeled isoguanine (iso-dG) substrate penetrate into iso-dC. A couple of intra "antisense" sequence primers which marked different report dyes can conducts one or multi-channel real time primer fluorescence PCR.

(4) The combination of all three kinds of ID interference:

After selecting a pair of primers with 6-8 bases of non-complementary/identical ID sequence, one side/one end of primers conducted by "antisense" Oligo sequence intra primer, and another side of primers is conducted by adding antisense oligos method based on the nature identical ID technology. In this condition, "antisense" Oligo on 5' end of primers adopts sequence of 5-7 bases on the edge between its ID and 5' end region; ID adopts 3 bases at most, so as to avoid that Oligo on 5' end of one primer binds to identical sequence on ID of the other primer by matching, which makes of system more complicated. This joint interference technology also can combine with the fluorescent dyes, the fluorescent probe, and the product quenching PCR. The one side of the adding antisense oligos method based on the nature identical ID technology also can combine with the fluorescent labeled antisense intra primer, such as the selective dT base of ID or sequence of the one side chimeric primer labeled by reporter 6-FAM-dT, and its 5' end marked by quencher dabcyl or use 5' dG quenching base or sequence. Vice versa, A couple of intra "antisense" sequence primers which marked different report dyes can be detected by multi-channel PCR instrument only in one tube at the same time. This also can combine with the product quenching PCR, intra "antisense" primer 5' end can use 5 methyl isopropyl cytosine (iso-dC) label reporter dye, the PCR products quenching through the dabcyl labeled isoguanine (iso-dG) substrate penetrate into iso-dC generating the real-time fluorescent quantitative PCR and multiple real-time fluorescent PCR. And this is also applied to a series of the isothermal temperature gene amplification technology to improve its primer PD nonspecific performance. It includes: displacement amplification SDA, rolling circle amplification RCA, loop-mediated isothermal amplification LAMP, helicase-dependent amplification HDA, nucleic acid sequence-based amplification NASBA, transcription mediated amplification system TAS, etc.

Other nonspecific control measures: The polymerase chain reaction PCR has inherent nonspecific amplification of primer dimers (PD) which is reduced or eliminated by carefully designed identical middle sequence of primers or adding antisense oilgos against primers ID intra PCR system. But the serious aerosol of primer dimer products and template products from outside PCR system will be secondary/repeat amplification and cross-contamination that should be isolated by close the reaction tube, as well as the cross contamination of the positive specimens DNA and the nonspecific amplification of residual genome in the unpurified samples. That is to say, before outside PCR system nonspecific uncontrolled, any measures that inhibiting primer dimers (PD) non-specifics completely concealed by the pollution from outside the system, and any efforts are in vain. On the contrary, it can't find the way to control the nonspecific outside PCR system before PD nonspecific amplification inside PCR system be resolved well. This is why we failed to completely solve the PCR non-specifics and PCR primer dimer problem in the biological world at present.

Because the reaction tube of real time fluorescent PCR is not real closed during thermal cycling, the most simple and reliable way is adding mineral oil (also known as paraffin oil) to stop PCR product of colloidal aerosol leaking. The mineral oil, which is the same or a few times volume of the PCR reaction volume completely does not affect the fluorescence value transmitted, is added above the PCR reaction liquid in PCR reaction tube for physically isolation. However, the trace PCR reaction solution of residual above the surface of the mineral oil layer, which sealed the PCR react components in proper order added followed by instant centrifugation, is still effectively amplified under the thermal-cycling condition. Any tiny drop of PCR reaction solution has a large of product colloidal aerosol leaking called carryover contamination under this condition. By a strange coincidence the blank Ct value of carryover contamination or colloidal aerosol residual amount of last same PCR is around 30 cycles number in the regular mineral oil close condition. There is an evident that the volume of PCR after end is lost and a lot of green fluorescent leak stains are around the lid of the old PCR instrument. The prevention of carryover contamination is usually conducted by incorporating dUTP in all PCR products by substituting dUTP for dTTP, followed by treat all subsequent fully preassembled starting reactions with uracil-DNA glycosylase (UDG) which releases uracil from single- and double-stranded DNA of more than 6 bases. But UDG cannot efficiently hydrolysis the endogenous PD products intra PCR otherwise it will parallel cleaves PD and target products by adding excess UDG. False positive rate of real-time fluorescent PCR that combines UDG and dU substrates and sealed by mineral oil is lower than that of TaqMan probe of real-time fluorescence PCR. The optimum amount of UDG that is not affect target amplification efficiency is not enough to eliminate excess PD colloidal aerosol of carryover contamination by mineral oil sealed, when reaction is pre-treated at only 5-10 minutes of UDG incubation before PCR starting. The minimum PD colloidal aerosol of carryover contamination of the identical middle sequence of primers PCR can effectively degraded by optimum amount of UDG in short time of pre-treat under the mineral oil sealed condition. This is basically suitable for general science experiment and application. The clinical diagnosis has much higher standard that false-positive rate should reach the enzyme immune diagnosis level of less than 3%. To completely eliminate PCR product colloidal aerosol of carryover contamination, it must use a PCR ingredients "hot releasing" strategy to let the residual reaction solution above the surface of the mineral oil layer absolutely cannot be amplified. The "hot releasing" is taking a PCR components (better prefer a primer) to plus sticky and high gravity molecule as "postponed releasing" by heating. One side of primer is usually dissolved in 20% (w/v) Dextran, which previously add to the bottom of PCR tube followed by adding each composition in order, is layer stay at the bottom of tube. At last add mineral oil carefully to the PCR tube wall, it cannot mix and vortex to avoid damaging "postponed release" layer. Then centrifuge for an instant time to precipitate all reaction liquid to the bottom of the tube. The heavy pre-added primer of the tube bottom is hot mix to release into reaction after conducting PCR denature at 95 for 2-4 minutes to start PCR amplification. And the reaction solution above the surface of the mineral oil can't be effectively amplified to produce any PD or target products due to lack of complete PCR ingredients. The residual micro-liquid after mineral oil sealed only produces the trace colloidal aerosol without any effective amplification, these combine with dUTP and UDG measure completely eliminates the carryover contamination.

The prevention of non-specific amplification of residuary genome which is not purified in the samples is first by getting rid of specific sequence of primer as design option, and also through separating the right pairing of primer 3'end and the join force of mismatch of outside 3' end by the identical ID or same middle sequence of primers strategy. The prevention of positive sample DNA cross-contamination can only take nice PCR practices in a good separated/partitioned PCR laboratory. Good clinical genetic testing department must establish three independent laboratories that are uni-direction material flow and one way. They are the independent PCR reagent preparation room, the sample preparation and sample adding room. And the PCR amplification reaction room is away from other rooms. The sample adding room should be negative pressure or add sample in biological safety cabinet. No matter how simple the PCR laboratory is, it must establish reagent, sample adding, amplification areas which devise is one way of airflow, material flow and worker. And the sample adding room set up the negative pressure biological safety cabinet. The right standard operating procedures make the influence of the positive sample DNA cross-contamination be very limited.

The Verification of PD Experiment by SYBR Green I Real-Time Fluorescent PCR

The real-time fluorescent PCR is a process of real-time monitoring the whole reaction fluorescence curve and real-time displaying, with the relative fluorescence intensity value as the abscissa, and with amplification cycle number as the ordinate. Because even if in the same PCR reaction, the fluorescence value change at the terminal platform period is very big, and the fluorescent value repeatability is best at the logarithmic growth early period in the same PCR reaction. Therefore, the 10 times standard deviation above average fluorescence value of baseline of the PCR 3-15 cycles is defined as threshold, which is generally locating in PCR logarithmic growth early period of the PCR reaction. When the PCR fluorescent amplification curve reaches the threshold, whose cycle number is defined as Cycle threshold (Ct), there is negatively logarithmic relationship between Ct Cycle number and the original target molecule copy number of the sample. SYBR Green I real-time fluorescent PCR's quantification is the most accurate method if there is no PD disturb, it is also the most cutting edge tool for the research of primer nonspecific. This invention uses blank SYBR Green I real-time fluorescent PCR without containing template to test the nonspecific amplification and the background Ct value of the primers.

1. SYBR Green I Real-Time Fluorescent PCR Technology Practices

The materials used by this invention was purchased which including SYBR Green I from Invitrogen, LC green from Idaho Technology, substrates dNTP/dUTP, Taq, primers, probe and antisense oligo-nucleotides from Shanghai shengong Inc., the antisense PNA from PD Biotech, the chemical reagents from Aldrich/Sigma, the Taq, UDG, SSB, rTh made from our self, the real time fluorescence PCR instruments from Xian Tianlong TL988, Stratagene Mx3000p, Bio-Rad CFX96 model and so on.

Standard volume of conventional end point PCR reaction is generally 50100 µl, even 10 µl as the screen cloning method. Because the fluorescence value of positive reaction is not high and only a few folds higher than blank baseline, TaqMan real-time fluorescence PCR method requires at least 40 µl-50 µl reaction volume in order to enhance fluorescence contrast. Method of dye SYBR Green I real time fluorescent PCR can make any reaction system from nanoliter scale to microliter scale due to running fluorescence hundreds folds higher than baseline. There is mainly 25 µl-50 µl reaction volume in a single reaction tube, the general PCR chip single point only needs nanoliter reaction. This reaction takes 25 µl standard real-time fluorescence PCR reaction system as an example, in order to add PCR reaction components according to the following proportion to PCR reaction tube:

| | |
|---|---|
| upstream primer(5 µM) | 0.5 µL |
| downstream primers(5 µM) | 0.5 µL |
| dNTP(10 mM) | 0.5 µL |
| SYBR Green I(25×) | 1 µL |
| Taq polymerase(5U/µL) | 1 µL |
| 10 × PCR buffer | 2.5 µL |
| Distill water dH$_2$O | 9 µL |
| Total | 15 µL |

Prepare 15 µl PCR reaction solution in the PCR reaction tube as above, the remaining 10 µl volume is as test sample, or as standard products, or as test effects reagents, or 10 µl distill water dH$_2$O as blank of test primers alone, plus carefully along the tube wall in order, change a tip per each tube. The last, add 30 µl mineral oil on each reaction solution along the tube wall carefully, centrifuge for an instant time. For a group of 10 times PCR reaction, make a 10 times PCR solution in advance: prepare 15 µl×10=150 µl pre-mixture, then add 15 µl PCR pre-mixture to each PCR tube, followed by add 10 µl of sample, add 30 µl of mineral oil.

Put the prepared PCR reaction tube into real-time PCR instrument of any model which has excitation/absorbing light wavelength of 480 nm and detection/emitting wavelength of 520 nm. Set up the reaction condition, pre-reaction 95 for 2-4 minutes, then running 45 cycles of denature 94 for 20-30 seconds, annealing 54 for 30 seconds, extension 72 for 20-30 seconds, and reading fluorescent values in 72. The melting curve of doing 50° C.-90° C. melting is to analysis after the end of 45 amplified thermal cycles. If PCR instrument set up a hot-lid that is 105° C. when adding mineral oil sealed, it is better start PCR reaction to let gasified solution out before hot-lid ready. Otherwise, the residual reaction solution above the oil was gasified by hot-lid and condensed again near to the surface of mineral oil to continue be effective amplification and leaking.

For example of following verify experiment, 4. Entero-Virus (EV) quantitative real time PCR is using 5' UTR of EV conserved region cloned to pUC$_{19}$ plasmid as modified template pUTR$_{ev}$ by a pair of conventional designed primers without identical ID/middle sequence. The plasmid pUTR$_{ev}$ do 10 fold dilutions in turn as templates to make the standard curve. The results see following data and FIG. 4.

| Copies of pUTR$_{ev}$ | $4 \times 10^8$ | $4 \times 10^7$ | $4 \times 10^6{}^8$ | $4 \times 10^5$ | $4 \times 10^4$ | $4 \times 10^3$ | $4 \times 10^2$ | $4 \times 10^1$ | $4 \times 10^0$ | 0.00 |
|---|---|---|---|---|---|---|---|---|---|---|
| Ct (Ct No.) | 13 | 16 | 19.5 | 23 | 26 | 29 | 30 | 30.5 | 30.5 | 31 |

The background Ct of blank control without adding template is crushed together with $10^3$ thousand copies of the low concentration of template at the same 30 cycles.

2. Verify 5' End or Middle or 3' End of One Primer as a Template of PD Amplification by Another Primer 3' end Based on many experimental results such as PCR primer extension usually begins from the correct match and hybrid 3' end, the 2-3 base mismatch of primer 3' end is unable to extend. How and where of one primer as a template of PD amplification by another primer 3' end? Of course the middle probability of one primer is bigger, two ends is less. In order to verify what is the main pathway of primer dimer PD nonspecific, we choose three groups of primer pairs, the first pair has continuous 4-6 base reverse complementation at a primer 3' end and another primer 3' end, the second pair has continuous 4-6base reverse complementation at a primer 3' end and the middle of another primer, the third pair has continuous 4-6base reverse complementation at a primer 3' end and another primer 5' end. Using continuous several bases of reverse complementation instead of optimized primer's 1-2 bases reverse complementation is to amplify the effect, if continuous several bases of reverse complementation is not the main reason for PD that few 1-2 bases reverse complementation nor is the main reason for PD. The results showed that the first group's amplification curve was climbed within 6-12 cycles of background Ct value, the second group amplification curve was climbed in 30 cycles-no Ct (linear), the third group's amplification curve was climbed in 35 cycles-no Ct (linear). There was no promoting effect when a primer 3'end and another primer in middle/5' end were continuous reverse complementation. The conclusion is that a primer 3' end with another primer 3' end as a template is the main reason for PD nonspecific. Primer 3' end area is important for both specificity and nonspecific, especially 3' end 1-2 bases correct matching can only be extended.

Three groups of test had good repetition, so HBVF/HBVR, HIVF/HIVR six pairs of primers belonging to the hepatitis B virus HBV and HIV genes as representative and display the results as follows:

```
                                          (SEQ ID NO:1)
    HBVF1(nt321):
    5'-c aac ctc caa tca ctc acc-3'

(SEQ ID NO:2)
    HBVR1(nt125):
    3'-gag tgg gta tag cag tta ga-5'
```

-continued (SEQ ID NO:3)
HIVF2(nt7520):
5'-c ctc caa tcg aag gag aaa-3'
(HIV-1: JX236678.1)

(SEQ ID NO:4)
HIVR2(nt7756):
3'-ctc ttt ttt ctc gtc aac ct-5'

(SEQ ID NO:5)
HBVF3(nt281):
5'-ggg gga gca ccc acg tgt c-3'

(SEQ ID NO:6)
HBVR3(nt129):
3'-gt ggg tat agc agt tag aag-5'

(SEQ ID NO:7)
HBVF4(nt276):
5'-ttc tag ggg gag cac cca-3'

(SEQ ID NO:8)
HBVR4(nt123):
3'-gac gga gtg ggt ata gca gt-5'

(SEQ ID NO:9)
HCVF5(nt42):
5'-ccc tgt gag gaa cta ctg tc-3'
(HCV: JX14307.1)

(SEQ ID NO:10)
SYNCRIP5(nt5942)
3'-gag tga ctt ttg aca gac gtc-5'
(NCBI Seq: NM 00125771.1)

(SEQ ID NO:11)
HBVR6(nt1340):
5'-gag ttg tcg gtt ccg atg ag-3'

(SEQ ID NO:12)
HPVF6(nt685):
3'-aac agc agt cct cac ttg ca-5'
(HPV: HM537001.1)

Test tubes 1-7 are blank PCR assay containing only primers, primers were both 5 µM conventional concentration, which were operated and prepared according to verification experiment 1. the primer pairs 1-2 were for the first group, the primer pairs 3-4 were for the second group, the primer pairs 5-6 were for the third group, the primer pair 7 was general control primer, then tube 1-7 proceed 45 thermal cycles at the same time: denature 94 30 seconds, annealing 54 30 seconds, extension 72 30 seconds, and reading fluorescent values in extension 72.

| | Test tube no. | | | | | | |
|---|---|---|---|---|---|---|---|
| | 1 | 2 | 3 | 4 | 5 | 6 | 7 |
| CT value | 6 | 12 | 31 | No (line) | 35 | No (line) | 29.5 |

The results:Tube 1-2 (group No. 1) a primer 3' end and another primer 3' end 6 bases consecutive reverse complementation's background Ct value was 6-12 cycles, tube 3-4 (group No. 2) a primer 3' end and another primer middle/5' end 6 bases consecutive's background Ct value was 30 cycles-no Ct (baseline), tube 5-6 (group No. 3) a primer 3' end and another primer middle/5' end 6 bases consecutive reverse complementation's background Ct value was 35 cycles-no Ct (baseline), The PCR that a primer 3' end and another primer intermediate domain/5' end had 6 bases consecutive reverse complementation didn't promote background Ct value. Therefore few complementation that a primer 3' end was with another primer intermediate domain/5' end as template definitely was not the main reason of PD nonspecific; The PCR that a primer 3' end and another primer 3' end had 6 bases consecutive reverse complementation obviously promoted background Ct value. Therefore reverse complementation that a primer 3' end was with another primer 3' end as template was the main reason of PD nonspecific. But whether enough of 3' end a few bases reverse complementation alone did promote a pair of primers' PD nonspecific?

3. Verify Whether a Few Bases' Complementation of Primers 3' End Alone is a Major Reason of PD Amplification:

The PD amplification is depended on the 1-2 bases extending of primers 3' end collide pairing per each thermal cycle at annealing temperature or primers 3' end reverse pairing work together with the mismatched hybridization outside of 3'end? The so-called "the collided pairing and instant extending in high annealing temperature" is an assumed possible condition that, when a pair of primers have few 1-2 bases complementation of 3' end under the condition of PCR thermal cycling. Because of thermal cycle high temperature accelerating molecular thermal motion, the few 1-2 complementary bases of 3' end extend 1-2 bases after colliding and combining at the moment of high temperature, then denature and separate. To that a pair of primers 3' end a few 1-2 bases complementation produces PD nonspecific with instantaneous collision independently, or with the force outside 3' end which help 3' end complementation base' stabilizing annealing extension. A pair of 6-8 bp short Oligomer is designed as primers 3' end complementary "short template". The left half antisense strand the Oligo reversely matched with 3' end of forward primer, the right half sense strand of the Oligo reversely matched with end of downstream primer. But the short Oligo as bridge of 3' end only can match and hybridize with the 3' end 3-4 bases of pair of primers that need an auxiliary force of random hydrogen bond of mis-pairing outside primers 3' end. The results that the short Oligo significantly promoted this pair of primers' background Ct value of regular PCR procedure after the 5 cycles of 4-8 annealing, room temperature extending, 94 denature. But it completely didn't promote this pair of primers' PD amplification at the 42 annealing PCR cycling condition after the Oligo postponed release and hot-start. That means 3-4 bases of reverse complementary hydrogen bonding force was insufficient to combine and extend primers independently under the condition of PCR thermal cycling. The conclusion is that primers 3' end's pair bonding must had the auxiliary of resultant force outside 3' end, which made 3' end a few complementary bases anneal and extend, producing PD nonspecific amplification.

With hepatitis B virus HBV core antigen gene's primers HBVcF/HBVcR as a representative test:

(SEQ ID NO:13)
HBVcF:
5'-atg ccc cta tct tat caa c-3'

OligoBVc3:
5'caa cg tcg

3'gtt gc agc (SEQ ID NO:14)
HBVcR:
3'-cag cgt ctt cta gag tta g-5'

All test tube 1-7 contain conventional concentration HBVcF/HBVcR, Test tube 1-2-3 that short Oligo was diluted 3 points, is low temperature annealed and extended 5 cycles followed by regular PCR procedure, Test tube 4-5-6 that short Oligo in 20% Dextran added to the bottom of the tube previously, proceed postponed-release & hot start PCR at 42 annealing, then tube 1-7 proceed 45 thermal cycles at the same time: denature 94 30 seconds, annealing 42 30 seconds, extension 70 30 seconds. The results see as below data:

| | Test tube no. | | | | | | |
|---|---|---|---|---|---|---|---|
| | 1 | 2 | 3 | 4 | 5 | 6 | 7 |
| Add Oligo: 2 µL | 100 µM | 10 µM | 1 µM | 100 µM | 10 µM | 1 µM | 0 (2 µL Dextran) |
| CT value | 15 | 19.5 | 22.5 | 39 | 45 | 41 | 35.5 |

The results (FIG. 6) showed that the PCR background Ct value was 15-22 when short Oligo of Test tube 1-2-3 annealed, extended at low temperature, then regular PCR procedure, but the PCR background Ct value was 39-45 when short Oligo of Test tube 4-5-6 proceeds postponed-release and hot start, then regular real time PCR only annealed at 42. A pair of primers combing with four bases "bridge oligo" without mismatch pairing of outside 3' end completely didn't promote the primers' PD nonspecific amplification.

4. The Non-Complement or Identical ID of a Pair of Primers Selectivity Inhibit PD and Push Back the Blank Ct:

How does the rest of a pair of primers 3' end which only fewer bases be reverse paired can binds each other to let paired end extending? No way is reverse complementary. But these primers have to be parallel complementary in 5'-3' direction. The only possible way is that a pair of primers 3'end a few bases twist turn and pair by the way of reverse complementation, both turned primers 5'end and middle sequences parallel pair from 5'end to 3'end, and bind through forming some random hydrogen bond. Because the parallel binding was formed under the nonphysical condition in vitro, the random hydrogen binding force is not strong and needs nearly full-length sequence random hydrogen binding. So the longer PCR annealing time to extending long enough fragment or more cycles amplify enough copies let the PD into exponential amplification. to the non-complement intermediate ID or same middle sequence of a pair of primers that damaging/distracting the primer 3'end a few matching hydrogen bonding force and the random hydrogen bonding force outside of 3' end, it inhibits PD nonspecific amplification. Design the primer pairs of parallel 100% homo-sequence, reverse 100% homo-sequence, parallel 70% homo-sequence, parallel 50% homo-sequence, middle 4-6 base ID parallel complement, middle 6-8base ID parallel non-complement, middle 6-8base ID parallel homo-sequence, 5'end 6-8base parallel homo-sequence, 3'end 6-8base parallel homo-sequence, and conducted the blank real-time fluorescent PCR test of only primer pairs without template. Results showed that the primers of parallel 70% or more than 70% homo-sequence inhibited PD nonspecific completely, the primers of parallel less than 70% homo-sequence (50% homo-sequence) and the primers of reverse 100% didn't inhibit PD nonspecific. But the primers of middle 4-6base parallel complement also postponed PCR background Ct cycle backward a few cycles rather than prompting. And the most primers of middle 6-8base parallel non-complement/sequences postponed blank PCR background Ct cycle 10 cycles or more. The conclusion is that both ends of single-strand PCR products (including PD products) produced by the primers of parallel 100% homo-sequence had 100% complement to form the pan-handle like structure, which not only effectively inhibited PD nonspecific, but also completely disturbed target specific amplification through own intra-molecular combination that competing with primer. And products produced by the primers of reverse 100% homo-sequence had inverse complementation to form e-type double circle by closer itself competing with primer. The own binding of both ends of PD single-strand was not the major factor of PD nonspecific, only was a secondary reason. A pair of primers of middle 6-8 bases parallel non-complement/same sequence ID disperse/damage the hydrogen bonding force formed by 3' end 1-2 complementary bases and the random hydrogen bonding force outside of 3' end due to purine and purine, pyrimidine and pyrimidine of ID not pairing to form hydrogen bonds. This made 1-2 complementary bases of primer pair 3' end not stabilizing combination and extension independently, then PD nonspecific and pushed back the blank PCR background Ct value under the condition of PCR thermal cycling. As the primers of middle 4-6base parallel complement should "theoretically" prompt PCR background Ct cycle forward rather than postponing. This could be the middle 4-6base parallel correct complement stronger than random hydrogen bonding to damage the coordination of primers 3' end pairing and random hydrogen bonding force outside 3' end.

With hepatitis B virus HBV, EV genes' primers as HBVEn/HBVRn as the representative test:

All test tubes 1-10 containing 5 µM conventional concentration HBVFn/HBVRn, EVFn/EVRn were blank PCR test that just contain primers, wherein tube 1-2-3 were the primer pair of parallel $R_1/R_1$100%, $R_1/R_2$70%, $R_1/R_3$50% homo-sequence respectively, tube 4 was $R_1/R_4$ reverse 100% homo-sequence, tube 5 was the primer pair of ID domain 6 bases parallel complement, tube 6 was the primer pair of ID domain 8 base parallel non-complement, tube 7-8 were the ID domain parallel homo-sequence, tube 9 was 5'end 7bases parallel homo-sequence, and tube 10 was 3'end 7bases parallel homo-sequence, then tubes 1-10 all proceed preheat 94° C.2-4 minutes and then 45 thermal cycles of denature 94° C. 20-30 seconds, annealing 54° C. 30 seconds, extension 72° C.20-30 seconds, reading fluorescent values in extension 72° C. . . . .

(SEQ ID NO:15)
HbVxR₁(nt1819):
5'-c atg gtg ctg gtg aac ac-3'

(SEQ ID NO:16)
HbTn70R₂:
5'-*g gac* gtg ctg gtg *tct* ac-3'
(Blackbody inclined-writing bases represent unnatural variation)

(SEQ ID NO:17)
HbBi50R₃:
5'-c atg *tcc gag cca* aac ac-3'
(Blackbody inclined-writing bases represent unnatural variation)

-continued

HbDaoR₄: (SEQ ID NO:18)
5'-ca caa gtg gtc gtg gta c-3'
(Blackbody inclined-writing sequences represent inverted same order)

HbVF₅(nt317): (SEQ ID NO:19)
5'-g tcc cca acc tcc aat cac-3'
(The inclined-writing bases above underline represent parallel complement)

HbVR₅(nt354): (SEQ ID NO:20)
5'-gag gac aag agg ttg gtg ag-3'

HbVsF₆(nt596): (SEQ ID NO:21)
5'-gca cct gta ttt aag gcc cat c-3'

HbVsR₆(nt765): (SEQ ID NO:22)
5'-ggc ccc caa cc gga att cat c-3'
(Blackbody inclined-writing bases represent unnatural variant parallel non-complement)

HBVcF: (SEQ ID NO:13)
5'-atg ccc cta tct tat caa c-3'

HaBVcR: (SEQ ID NO:14)
5'-gat tga gat ctt atg cga c-3'
(Bold a was mutated and optimized from the original c, the bases above underline represent homo-sequence)

EVF₈(nt434): (SEQ ID NO:24)
5'-gag cta gtt agt agt cct c-3'

EVR₈(nt556): (SEQ ID NO:25)
5'-acc caa agt agt cgg ttc-3'
(The bases above underline represent parallel homo-sequence)

EVF₉(nt443): (SEQ ID NO:26)
5'-agt agt cct ccg gcc cct g-3'

EVR₉(nt550): (SEQ ID NO:27)
5'-atg agt cgg ttc cgc tgc ag-3'
(The bases above underline represent parallel homo-sequence)

EVF₁₀(nt431): (SEQ ID NO:28)
5'-act gag cta gtt agt agt c-3'

EVR₁₀(nt562): (SEQ ID NO:29)
5'-acg gac acc caa agt agt c-3'
(The bases above underline represent parallel homo-sequence)

| Test tube no. | | | | | | | | | | |
|---|---|---|---|---|---|---|---|---|---|---|
| | 1 | 2 | 3 | 4 | 5 | 6 | 7 | 8 | 9 | 10 |
| CT value | No (line) | 44 | 31 | 30.5 | 24 | 43 | 37.5 | 40 | 26 | 29.5 |

Results see (FIG. 7) tube 6, 7, 8, which is a pair of primers of middle 6-8 bases parallel non-complement or identical ID, because the identical ID bases due to purine to purine, pyridine to pyridine cannot form hydrogen bonds to damage or/disperse the joint force between primer 3' end 1-2 base complement and 5' end random complement, the primers with the 3' end fewer 1-2 base complement cannot independently get together, therefore it inhibit PD nonspecific and postponed blank PCR background Ct cycle almost 10 cycles or more.

5. The Antisense Oligos that Complement with ID Significantly Inhibited PD Nonspecifics and Postponed Blank PCR Background Ct Value:

The bigger antisense oligo-nucleotides such as oligomer (>14 bases) which can combine with more than 70% primer sequences will significantly inhibit PD nonspecific, but also non-selectively inhibited target specific amplification. A pair of primers 3' end a few bases reverse complementation didn't stabilize combination independently under the condition of PCR thermal cycling, and need the auxiliary of random hydrogen bonding force formed by primers 5'end and middle sequence parallel pairing from 5'end to 3'end after the pair of primers 3'end a few bases twisted turn and paired by the way of reverse complementation. This assumption model putted forward that inhibiting primer ID sequence antisense Oligo may be inhibited PD nonspecific selectively at the situation that target amplification was not affected. In order to validate and test whether the primer ID sequence is the major determinants, and primer ID antisense Oligo effectively inhibit PD nonspecific independently. Set blank real-time fluorescence PCR test, which contained the antisense Oligos of parallel 9bases, 12bases ID complemented from 5' to 3'end, 8bases reverse ID complemented, 8bases reverse 5'end complemented, 8bases reverse 3'end complemented and the control of only primers respectively. Results showed that the equal molecular quantity of antisense oligo-nucleotides (5 μM concentration of primers plus 3 μM-6 μM antisense Oligo) obviously inhibited PD nonspecific, except for the 5' end of complementary antisense Oligo having no effect, and the antisense Oligo complemented parallel with short 9 bases ID from 5' to 3'end having weak effect, which only pushed background Ct value back 3-4 cycles, the rest of the background Ct values were nothing (amplification curves were baseline), the primers ID antisense Oligo could effectively inhibit PD nonspecific independently, using it alone or combination with middle non-complement/homo-sequence ID primers both didn't affect target specific amplification efficiency (see the standard curve of example implementation). Conclusion: The equal quantity of antisense Oligo complemented with primers ID effectively inhibit PD nonspecific, and delayed blank PCR background Ct value infinitely without affecting target specific amplification, The case that antisense Oligo complemented parallel with longer 12 bases middle sequence from 5'→3'end can also inhibit PD nonspecifics have proved that primers could combined by parallel matching and random complementation.

With hepatitis B virus HBV gene's primers HBV₍c₎F/H₍a₎BV₍c₎R as the representative tests: added all kinds of antisense Oligoes.

All test tube 1-6 were the blank PCR test which contained 5 μM conventional concentration primer pair HBVcF/HBVcR, meanwhile, tube 1 add antisense Oligos which complemented parallel with 9 bases ID from 5' to 3'end, tube 2 add antisense Oligos which complemented parallel with 12 bases middle sequence from 5' to 3' end, tube 3 add antisense Oligos which reverse complemented with 8 bases ID, tube 4 add antisense Oligos which reverse complemented with 8 bases 5' end, tube 5 add antisense Oligo which reverse complemented with 8 bases 3' end, tube 6 add only the control primers group without antisense Oligo. Test tube 1-6 proceed pre-reaction 95° C. 2-4 minutes, then 45 thermal cycles of denature 94 20-30 seconds, annealing 54 30 seconds, extension 72 20-30 seconds, and reading fluorescent values in extension 72.

The sequences of antisense oligo-nucleotides are as follows:

As Oligo1:
5'-gat a/i20 Meg/aat a-3'(3' P)
(3' P represented phosphorylation of 3'end, the
5th base g was 2'-O-Methyl (OMe) modified RNA)

(SEQ ID NO:30)
As Oligo2:
5'-ggg ata/i20 Meg/aa ta/i20 Meg/-3'
(The 7th, 2th bases g were 2'-O-Methyl (OMe)
modified RNA)

As Oligo3:
5'-taa/i20 Meg/ata/i20 Meg/-3'
(The 4th, 8th bases g were 2'-O-Methyl (OMe)
modified RNA)

As Oligo4:
5'-agg/i20 Meg/gca/i20 Met/-3'
(The 4th, 8th bases were 2'-O-Methyl (OMe)
modified RNA)

As Olieo5:
5'-gtt/i20 Meg/ata/i20 Mea/-3'
(The 4th, 8th bases were 2'-O-Methyl (OMe)
modified (RNA)

| | Test tube no. | | | | |
|---|---|---|---|---|---|
| 1 | 2 | 3 | 4 | 5 | 6 |
| CT value 36 | No (line) | No (line) | 31 | No (line) | 32 |

Results see (FIG. 8), tube 3 add antisense Oligos which reverse complemented with 8 bases ID of primer, the equal quantity of antisense Oligo complemented with primers ID effectively inhibit PD nonspecific, and postponed blank PCR background Ct value infinitely. In the tube 2, longer antisense Oligo of 12 bases which is parallel complementary to ID of primers in direction of 5'-3' also has similar PD inhibition effection. This proved that Oligo/primers could bonded through forming random hydrogen by parallel matching complementary in the same 5 to 3' direction.

6. The Combination of the Identical ID Sequence of a Pair of Primers and Single-Stranded Binding Protein (SSB) Synergetically Inhibit PD Nonspecific:

Single Binding Protein (SSB) has a certain inhibitory effect of PCR nonspecific, and shall not affect the efficiency of target specific amplification. Maybe just with the reason that SSB does not inhibit the target-specific amplification, the effect of SSB inhibiting PD nonspecific is limited for the no optimized primers whose background Ct value are before 30 cycles (<30 Ct value), perhaps the PD non-specific amplification mechanism for no optimal primers is similar to target specific amplification, just with different in degree. Conducted blank real-time fluorescence PCR tests with non-optimized primers, antisense Oligo+common primers, optimized same sequence ID primers, antisense Oligo+same ID sequence primers, etc, and blank real-time fluorescence PCR tests which added 4 times molecules number of SSB to the same 4 groups of oligo primers etc. By comparing the results, it showed that the effect of SSB inhibiting PD nonspecific had a large difference. The more optimized/background Ct value rearwards primers, and SSB had a stronger synergetically inhibiting effect for PD nonspecific, both mutually enhanced and amplified the inhibiting effect of PD nonspecific with positive synergy. SSB didn't further enhance antisense Oligo inhibitory effect of PD nonspecific, probably both were in the same pathway. Conclusion was that the effect of SSB was similar to that of antisense Oligo relying on competitive inhibition of combination, which lacked differential in selectivity for the target-specific combination and PD nonspecific combination, SSB had obvious synergistic and enhanced inhibitory effect for PD nonspecific after this differentiation of SSB was strengthened by primer design.

With hepatitis B virus HBV surface antigen gene's non-optimal primers HBVsF/HBVsR and core antigen gene's primers HBVcF/HaBVcR which had a artificial mutation and optimization as the representative tests:

```
                                        (SEQ ID NO:31)
HBVsF: 5'-gca cct gta ttc cca tcc cat c-3'
                                        (SEQ ID NO:32)
HBVsR: 5'-ggc ccc caa tac cac atc atc-3'
                                        (SEQ ID NO:13)
HBVcF: 5'-atg ccc cta tct tat caa c-3'
                                        (SEQ ID NO:23)
HaBVcR: 5'-gat tga gat ctt atg cga c-3'
(The crude-writing a which artificially mutated
and optimizated from original c, underlined
sequences were the same sequences)
```

All test tube 1-8 were the blank PCR tests which contained 5 μM conventional concentration primer pair, tube 1 add common non-optimized primers HBVsF/HBVsR, tube 2 add common primers+ID antisense Oligo, tube 3 add optimized identical ID primers HBVcF/HaBVcR, tube 4 add optimized primers+ID antisense Oligo3, the tube 5-8 add 4 folds SSB to above tube 1-4 group. The tube 1-8 proceed pre-reaction 95° C. 2-4 minutes, then 45 thermal cycles of denature 94 20-30 seconds, annealing 54 30 seconds, extension 72 20-30 seconds, and reading fluorescent values in extension 72.

| | Test tube no. | | | | | | | |
|---|---|---|---|---|---|---|---|---|
| | 1 | 2 | 3 | 4 | 5 | 6 | 7 | 8 |
| CT value | 26 | 31 | 38 | No (line) | 28 | 35 | No (line) | No (line) |

The results see (FIG. 9), For non-optimized conventional design primers, when added SSB and/or As Oligo to blank PCR, it only slightly inhibited PD nonspecific amplification; while for elaborate optimized primer pair with middle ID of non-complementary/same sequence, when added SSB and/or As Oligo to blank PCR, it significantly inhibited PD nonspecific, The synergies of optimized design and SSB/Oligo As amplified their inhibitory effect of PD nonspecific, which immortally pushed the background Ct value back, and made the fluorescence curve be still a straight line within the real-time fluorescent PCR detection range or 45 thermal cycle reaction, without nonspecific amplification.

In summary, the unmatched or identical middle sequence (also called intermediate domain, ID) of primers is major factor to selectively inhibit PD nonspecific amplification. By combining to use the antisense bases against ID, and antisense base intra primer, and optimized PCR enhancers based on unmatched or identical ID can completely eliminate the PD nonspecific amplification without affecting target specific amplification efficiency and indeed solve the PCR fundamental nonspecific problem. The PCR conduct under the strict closed reaction which is using a PCR ingredient (prefer a primer) "postponed release" by heat and incorporating dUTP in PCR product followed by treating starting reactions with glycosylase (UDG) in the mineral oil sealing condition. The integrated measures let the residual solution above the oil without a primer cannot be amplified. Therefore PCR reaction mixed by PCR pre-heating release heavy primer into start PCR amplification. The any leaked products of trace colloidal aerosol are further degraded by UDG.

The present invention's application:

(1). Quantitative Detection of Gene Expression of mRNA Level

With the completion of the sequencing of the human genome, the life science is entering functional genome research and functional protein, which need a large amount of mRNA reverse transcribe into cDNA for quantitative function research, quantitatively demonstrate different expression of genome, some reporter genes associated with clinical disease genes have been found more and more, all of these need a lot of quantitative fluorescent reverse transcription PCR. The sample RNA is prepared by conventional GuanidineThiocyanate one-step method or Trizol method, there is no special requirement. Reverse transcription (RT) can be divided into reverse transcription reaction and amplification reaction, also can have one-step reaction with PCR. Rapid detection selects one-step RT-PCR single pipe reaction, single tube joins two different types of enzymes, which are the reverse transcriptase (such as AMV or M-MLV mutant, SuperScript II/SuperScript reverse transcriptase enzyme, etc.) used for RT and the thermostable DNA polymerase (such as Taq, Taq Plus, etc.) used for real-time PCR. The activity of thermostable DNA polymerase is inhibited by its antibody in the reverse transcription process, when enters the PCR process, heat denature makes reverse transcriptase inactivate, and also suppress the inactivation of the thermostable DNA polymerase's antibody, which make the amplification reaction proceed smoothly. Another strategy is to use the heat-resistant polymerase that has reverse transcriptase activity, but also has DNA polymerase activity.

(2) Trace Protein Antigen Quantitation is Detected Quantitatively by the Crosslinking of Antibody and Oligo The traditional quantitative antigen-antibody enzyme-linked immune-sorbent assay (ELISA) method, especially chemiluminescence ELISA method, is very accurate and has been very mature and applied on a large scale, but its sensitivity is still not enough, and generally only reaches nano-gram level. The molecule quantitative detection of smaller amounts of antigen and antibody depends on new immune PCR technology, which fills the blank of molecular quantitative detection through the sensitivity of femto-gram level caused by exponential amplification detection, the present invention is applied to the immune PCR, antigen or antibody cross-links with streptavidin, monitors the immune response with the 24-30 bases oligo-nucleotide DNA labeled by biotin, the corresponding amount of oligo-nucleotide DNA proceeds real-time fluorescent quantitative PCR assay, and calibrates standard curve. Antigen or antibody can also be covalently attached by using the bifunctional cross-linkers directly.

(3). Infectious Gene Screening/Quantitative Detection

Infectious diseases real-time PCR is the first field to start using real-time PCR to detect infectious diseases and screen blood, which drives or creates molecular diagnostics industry, the traditional ELISA detection of infectious diseases can gradually have corresponding real-time fluorescent quantitative PCR detection, which doesn't have leak detection of Elisa detection window phase, providing more sophisticated and higher sensitivity. This invention application example provides some representative practice models. Even further it can screens susceptibility genes of susceptible populations for infectious diseases.

(4). Genetic Diseases Gene Screening/Detection

Some typical genetic diseases derive from congenital genetic deficiency, such as α-thalassemia, Mongolia dementia, Duchenne muscular dystrophy, and even hereditary diabetics, as technology advances, there will be more disease may involve genetic reason, real-time fluorescence PCR in particular the real-time fluorescence PCR having no primer dimers nonspecific interference mentioned by the present invention, can be used as a fast, simple and effective method for the analysis of genetic diseases.

(5). Metabolic Diseases and Cancer Gene SNP Detection and Early Warning

With the superiority of modern life, metabolic diseases and tumor are more and more becoming the main health problems, bad living habits also work through certain internal factors—internal genes, more and more evidences suggest that the gene single nucleotide polymorphism (SNP) is associated with metabolic diseases, tumors often are caused by the accumulation of many mutations, and associated with a number of SNP genes, which are not determined by a single genet, with the improvement of human SNP database in the post-genomic era, real-time fluorescent PCR about the detection of SNP has a broad application prospect in medical diagnostics and personalized treatment.

(6). Genetic Fingerprint Identification and Medical Genetic Match Detection

For some marker gene with identification such as short tandem repeat/microsatellite DNA, Y chromosome genes, mitochondrial genes, HLA genes, whose polymorphism analysis of PCR amplification, restriction fragment length or amplified fragment length has become a major reliable method of forensic individual identification, paternity test and medical tissue typing. The method that using the optimized primers mentioned by the present invention to proceed saturated dye LC Green real-time fluorescent PCR, amplify with high precision PCR instrument (LightCycler480), and then analyzing the high resolution melting curve (HRM) will become the sharpest tool for a new generation of genetic fingerprinting and medical genotyping.

(7). Drug-Resistant Bacteria and Virus Gene Screening/Quantitative Detection

The abuse of antibiotics and other medicines and incorrect drug cause the flooding of drug-resistant bacteria today, new drug development far couldn't catch up with the development of bacterial drug resistance, especially there has been some super drug-resistant bacteria, if things go on like this, human will soon face the situation that there are the lack of medicines available, and no drugs available for curing. The real-time fluorescent PCR technology is fast and has a very high sensitivity, which will become a powerful weapon against the rapid development of super drug-resistant bacteria.

(8). The Food Contamination Intestinal Pathogenic Bacteria and Intestinal Pathogenic Virus Gene Screening Food safety issues increasingly become a focus of national attention in current, in addition to chemical pollution, biological harmful pollution is also a major health killer known as "illness enters via the mouth", the present invention is applied to the quad intestinal bacteria real-time fluorescence PCR kits of pathogenic *Staphylococcus aureus, Salmonella, Shigella* and pathogenic intestinal bacteria *E.* coli, and the quad intestinal bacteria real-time fluorescence PCR kits of enterovirus EV, rotavirus, newark virus and hepatitis A virus, which not only can be applied to clinical laboratory rapid diagnosis, can also be used for food production, food safety testing.

(9). Genetically Modified Agricultural Products and Processed Foods Screening/Quantitative Detection Transgenic technology greatly improves the crop yield, quality and benefit, but its biological safety problem is also increasingly concerned by governments and the public, agricultural products and processed food genetically modified ingredients monitoring has been promoted as an important means of food supervision and the fundamental guarantee of scientifically developing genetically modified industry, generally a variety of transgenic common promoter gene is as test template for real-time fluorescent PCR rapid detection.

(10). Agriculture and Animal Husbandry Pest Screening/Quantitative Detection

Modern Agriculture and animal husbandry has entered the era of scientific development, cheap and advanced real-time fluorescent PCR technology also has a very broad application in Agriculture and animal husbandry.

(11). Breeding Good Genes SNP Screening/Testing

Good genes screening and breeding are far superior to a traditional inefficient breeding means and method taking a chance from one generation to generation in time, efficiency, effectiveness, and cost, cheap and efficient real-time fluorescent PCR technology will become a right hand and important technology tool for genetic screening and breeding.

(12). Environmentally Harmful Bacteria Gene Quantitative Detection

Current environmental situation is grim, living garbage harmful bacteria monitoring only relies on cheap and practical real-time fluorescent PCR technology, and living garbage fermentation processing also need practical real-time fluorescent PCR technology.

(13). The Fermentation Industry Bacteria Genes Quantitative Detection

The monitoring of fermentation industry engineering bacteria and harmful bacteria contamination quality is also inseparable from cheap and practical real-time fluorescent PCR technology and the improvement of the present invention.

(14). Others, such as any trace gene amplification, quantitative determination in the research and development area.

Advantages of Invention (1). This invention "Primer Middle Sequence Interference PCR Method" captures the differentiation of primers specific and nonspecific amplification, controls the key primers dimer PD nonspecific amplification of the PCR, quantifying the low-density gene accurately, which is applicable to the accurate quantitative determination for the vast majority of the low copies of regulatory/functional genes and gene trace difference, really playing the extremely high sensitivity of PCR.

(2). Interruption of intermediate sequence of primers dominates non-specific amplification in PCR thermal cycling reaction system, mineral oil seal united dU substrate +UDG enzyme to digest the aerosol recontamination caused by micro leakage of PCR products, further combined with primer postponed-release hot start to completely eliminate the recontamination outside PCR system; Simple and reliable comprehensive measures are suitable for clinical molecular diagnosis, which can never have a primer non-specific false positive results. The clever measures of interruption of intermediate sequence of primers dominate the key problem of PD for the PCR, and solve the highest standards requirements of precision, accuracy and repeatability for clinical examination, especially being suitable for the real-time fluorescent PCR quantitative detection and accurate diagnosis of infectious diseases.

(3). The intermediate un-complement/same sequence primers having no PD interference promote high melting curve (HRM) analysis, due to saturated Green fluorescent dye LC having high combination efficiency with DNA, HRM can reflect the subtle change of single-base mutation, but also leads to more serious PD interference, it is almost impossible that analyzes HRM with no optimized primers, The intermediate non-complement/same sequence primers greatly improve the resolution that HRM (control standard) identifies specific gene "fingerprint".

(4). The primers having no mutual interference are suitable for multiple PCR amplification techniques, primers nonspecific amplification obstacles which are insurmountable for multiplex excessive Primer, only can be overcome with optimized primer and the method of interruption of intermediate sequence of primers, especially being suitable for multiple fluorescent PCR detection of the intestinal or respiratory pathogens.

(5). The present invention is suitable for isothermal fast amplification technique, isothermal amplification generally has a lower reaction temperature, which is more likely to produce primer dimer nonspecific amplification. The intermediate non-complement/same sequence optimized primers particularly help to improve the accuracy of rapid gene diagnostic.

(6). The present invention is suitable for micro-nano PCR chip technology, micro-nano PCR chip miniature device is more difficult to control primers non-specific amplification, which only can be solved by optimizing the design of the primer and interruption of intermediate sequence of primers.

EXAMPLES

Figure 1:
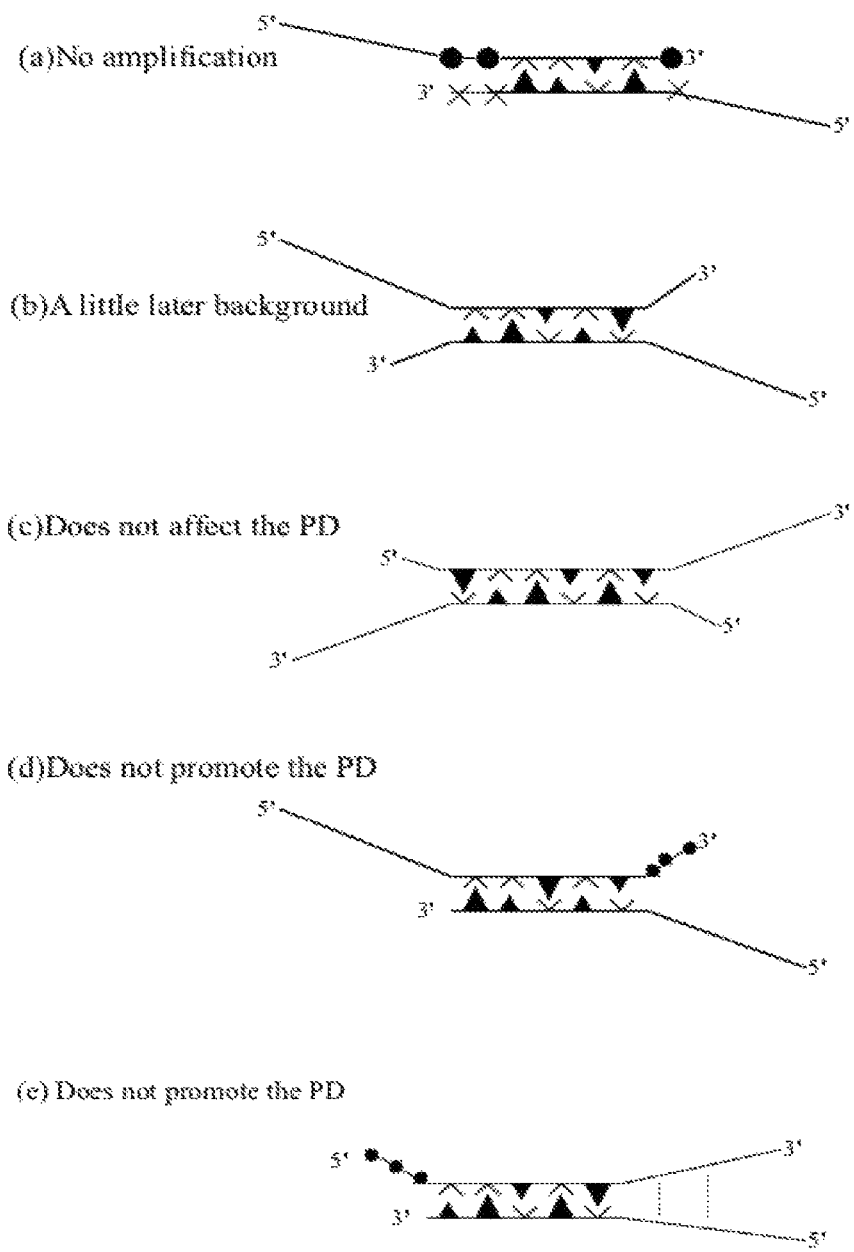
FIG. 1 is the schematic diagram excluding the formation reason of primer dimer PD, long line represents the DNA oligo-nucleotide chain and the 5'→3'direction marked, the symbol ▲Λ represents complementary bases, ●x represents the non-matching un-complement bases, first eliminates (a) a pair of primers having continuous complementary bases, but unmatched 3' end terminal two bases don't amplify effectively, then expand to (b) (c) a pair of primers having continuous complementary bases at middle/5' end, but unmatched bases at 3' end don't amplify; even (d)(e) a primer 3' end completely continuous complemented with another primer middle/5' end also don't promote the formation of primer dimer PD.
Figure 2:
FIG. 2 is the schematic diagram about the mechanism of primer dimer PD amplification, long line represents the DNA oligo-nucleotide chain and the 5'→3'direction marked, the symbol ▲Λ represents complementary bases, x ○ represents non-complement bases, and the curved line represents unmatched sequence, a few bases' complementary condition of a primer 3' end with another primer middle/5' end needs neighbouring random reverse matching hydrogen bond to stabilize combination, (c) a primer 3' end with another primer middle bias 3' end have the aid of rest of short reverse complementary bases and less random hydrogen bond, are not easy to form PD; (d) a few reverse complementary bases of a primer 3' end with another primer 5' end are also not easy to form PD, because they have the aid of rest of long reverse complementary bases and more random hydrogen bond, whose strong resultant force make double-strand repeatedly bind and have a short extension distance; (b) a primer 3' end with another primer near 3' end have a few reverse complementary bases, there are 1-2 bases interval from the least end, long interval is more similar to (c) (d); short interval is more similar to (a), a pair of primers having a few reverse complementary bases at each other 3'end need the aid of the matching hydrogen bonding from 5' to 3 ' parallel pair after the reverse fold of both 3' end.
Figure 2:
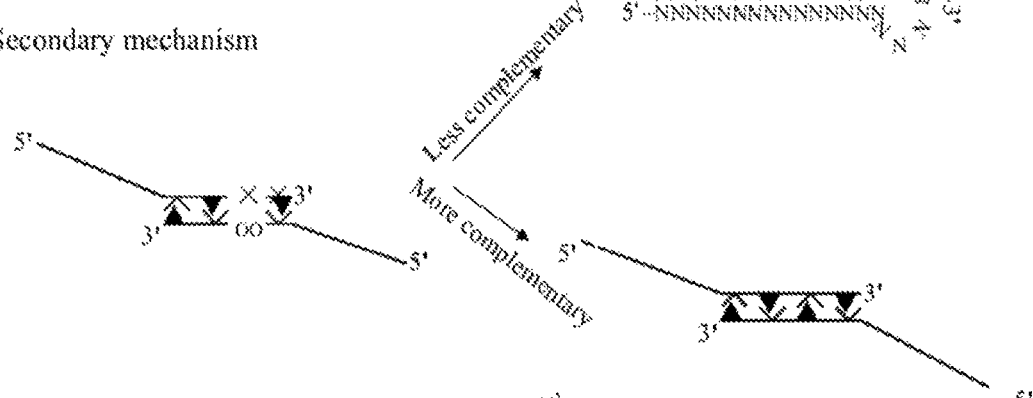
Figure 2:
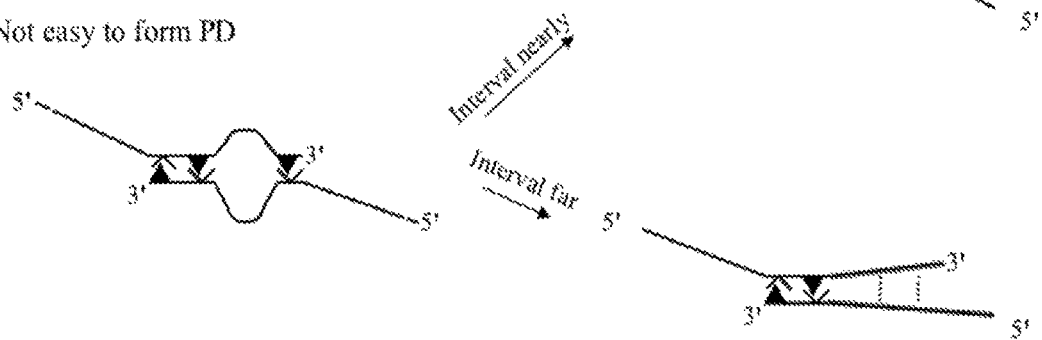
Figure 2:
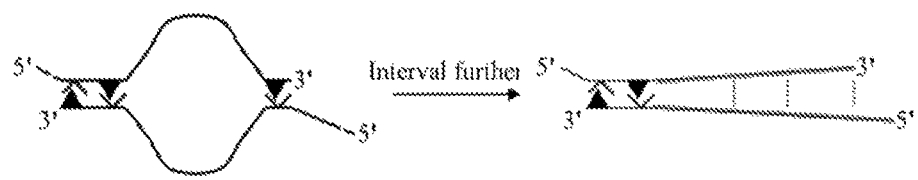
Figure 3:
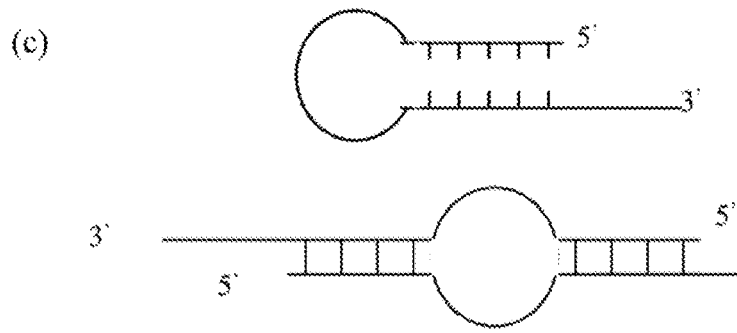
FIG. 3 is the primers formula about the design of the interruption of intermediate sequence of primers, (a) the primers formula about a pair of primers whose middle ID6-8 bases are unmatched/identical (/homo)-sequence, $F_n$ represents upstream primer sequence, $R_n$ represents downstream primer sequence, T represents unmatched/homo-sequence bases of middle ID; (b) the formula of antisense oligonucleotides As Oiligo, $O_n$ represents 7-10bases antisense bases sequence which can pair with the ID and middle of primer; (c) the primers formula about antisense base 5'Oiligo refolded to self-disturb ID intra-molecule, long line represents the primer chain and the 5'→3'direction marked, short bar represents paired and complementary bases within the primer hybrids, the 5' end complemented with ID is extra added 5-7 base antisense As Oiligo bases intraprimer, which moves toward ID-5' direction a couple of bases between antisense-ID when it combined with the strategy of identical ID primers.
Figure 4:
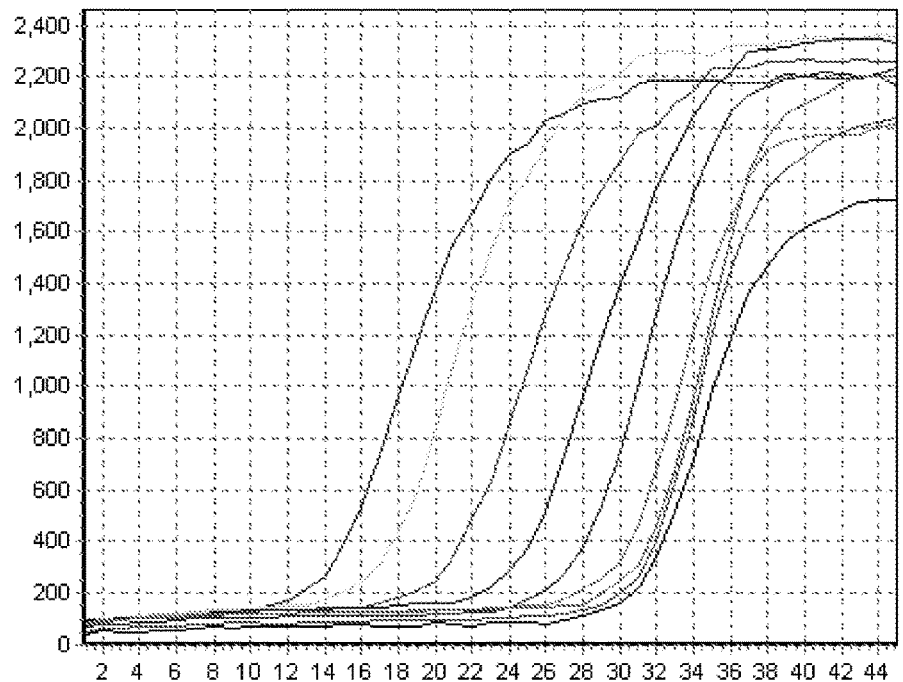
FIG. 4 is the real-time fluorescence PCR standard curve for ordinary un-optimized primers. The entero-virus positive control plasmid pUTRev $4\times10^8$ copies was diluted 10-folds in turn, whose Ct value are: 13, 16, 19.5, 23, 26, 29, 30, 30.5, 30.5, 31 cycle threshold. By starting from the $4\times10^3$ copies, the whole Ct values are crowded around 30 cycles, all the nonspecific Ct values inside and outside PCR system are at 30 cycles.
Figure 5:
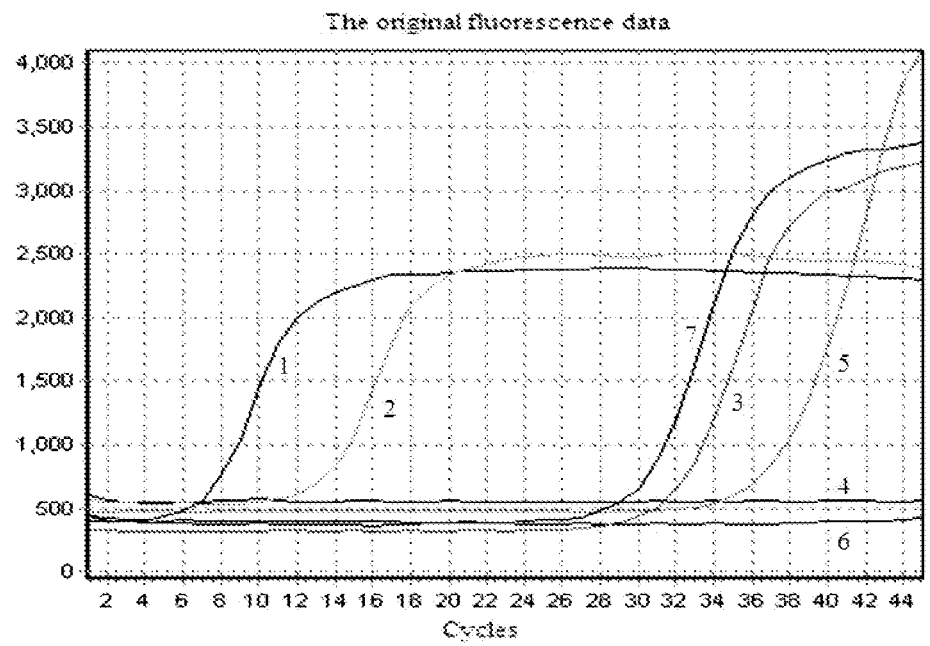
FIG. 5 is the experiment about the causes of PD. The 1-7 digit number is the test tube number in the amplification plot, the tube 1-2 are that a primer 3' end uses another primer 3 'end as template, which have a lot of PD amplification, and their Ct value are 6-12; the tube 3, 4/5, 6 are that a primer 3' end uses another primer middle/5' end as template, Ct values >30 and not promoting, which is not the main reason for the PD.
Figure 6:
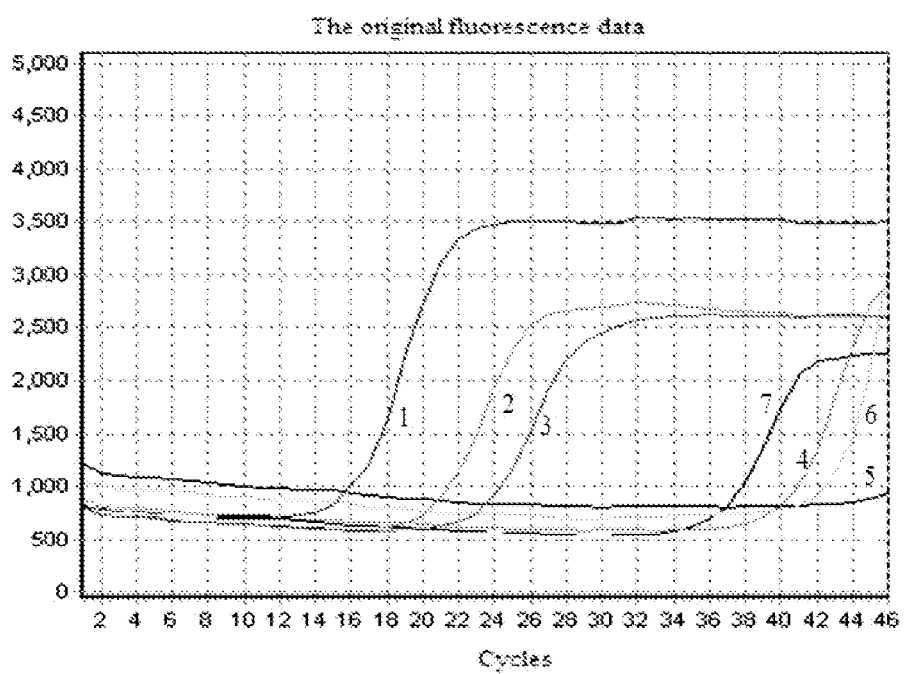
FIG. 6 is the experiment about the causes of PD. The experiment uses low Tm "short double-stranded Oligo" complemented with the primer 3' end as primer amplification short template, tube 1-3 are different concentrations of Oligo, which can effectively anneal and amplify at low temperature, the Ct value are 15-22; but the "short double-stranded Oligo" and primer 3' end have only 3-4bases weak combination, and lack the complementary force outside 3'end, tube 4-6 anneal at a little higher temperature (>40), the "short template" has no amplification, which Ct value>35; This proved that a pair of primers having a few reverse complementary bases of 3' end combined weak, need to use the forces outside 3'end to stabilize annealing and PD amplification.
Figure 7:
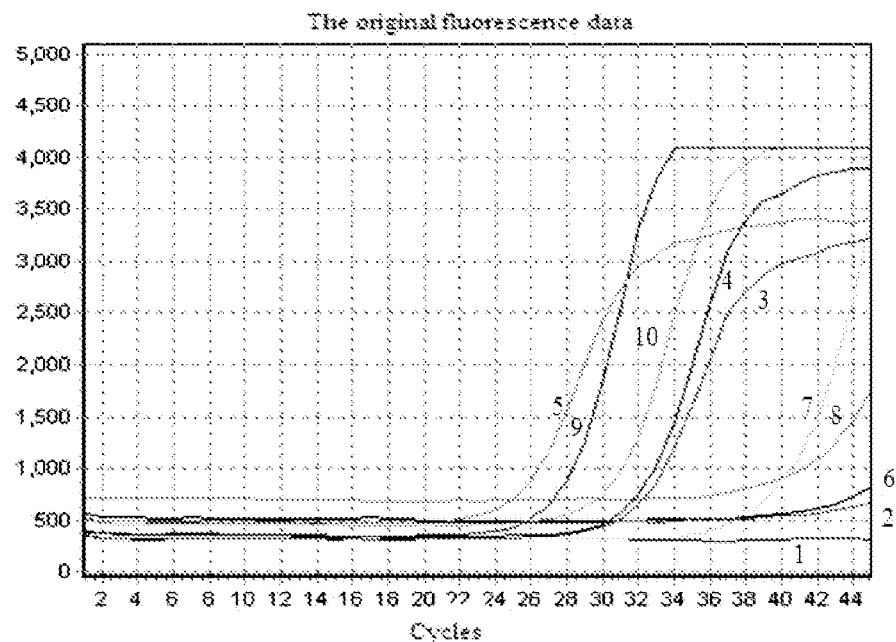
FIG. 7 is the experiment about ID unmatched/homo-sequence primers inhibiting PD. The tube 1-3's Ct values are promoting along with the reducing of the degree of homo-sequence, tube 4's reverse homo-sequence lost the effect of homo-sequence inhibiting PD, tube 6/7, 8 contain the primers having partial unmatched/homo-sequence, which also can achieve the effect of high homo-sequence primers inhibiting PD when the unmatched/homo-sequence are located in the key position of primer ID. The primer pairs having unmatched/homo-sequence maybe inhibit PD through dispersing/damaging a few weak binding complemented at 3'end and the random hydrogen bond force outside 3'end.
Figure 8:
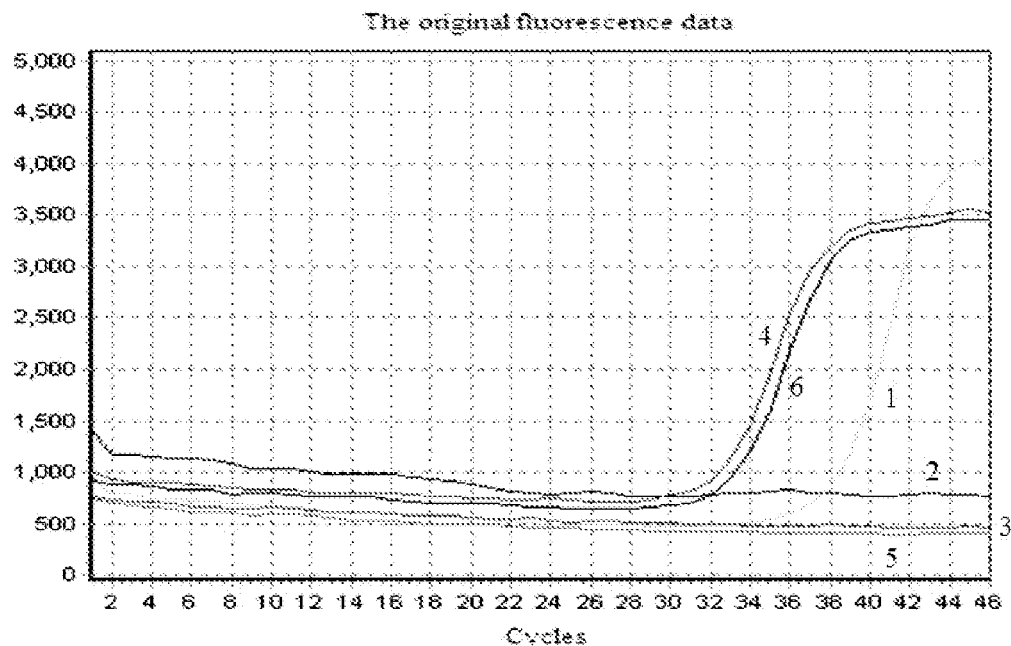
FIG. 8 is the experiment about the inhibiting PD by As Oligo against ID area. The tube 1-2 parallel longer complementary As Oligo inhibiting PD proves that Oligo and primer can pair and bond parallel from 5' to 3', so the primers can also pair and bond parallel from 5' to 3'; tube 3 As Oligo of primer ID area and tube 5 As Oligo of primer 3'end inhibit the PD independently; tube 4 As Oligo of primer 5'end and tube 6 control not inhibit the PD.
Figure 9:
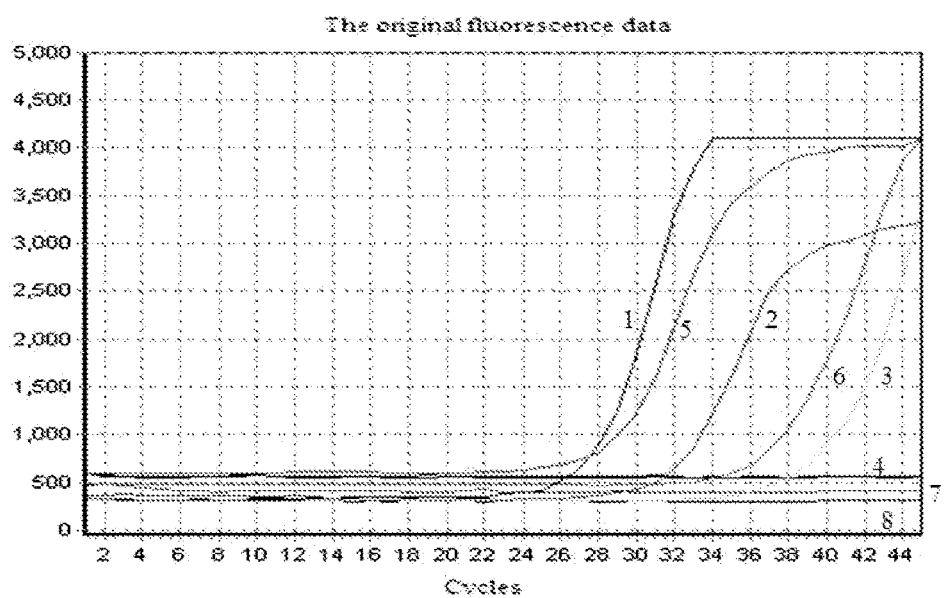
FIG. 9 is the experiment about synergy inhibition of SSB and primers of ID identical sequence. The tube 1 adding common primers versus tube 3 adding optimized primers of ID identical sequence, added As Oligo tube 2 versus tube 4, As Oligo inhibiting the effect of optimized primer PD is very obvious; compared to tube 5-8 adding SSB, the inhibitory effect of SSB cooperating with optimized primers of ID identical sequence is more obvious.

The following cases as representative further explains the content of this invention but should not be interpreted as the limitation of the invention. Without departing from the spirit and essence of this invention, the changes or replacement of this invention method, conditions, procedures and application all belong to the scope of this invention.

Example I: Human EnteroVirus' Real-Time Fluorescent PCR Detection

In recent years, the hand-foot-mouth disease started large-scale popular among young children in China, and the case fatality rate is high. The pathogenic Entero-Virus nucleic acid real-time fluorescent PCR detection becomes an important technology monitoring its infectious pop. EV is RNA viruses that initially divided into more than 60 different serotypes, including Entero Virus 68-71. Based on its nucleic acid sequence classification, EV is divided into five classes as A, B, C, D and PolioVirus, the main pathogenic strains Coxsackie A16 (CA16) and EnteroVirus 71 (EV71) are classified as human Entero Virus type A. Because of EV Entero Virus gene having great variation, only 5' UTR conservative, there are three regions of all strains of common Homologous conservative area (underlined). Published EV universal primers, which were selected from the conservative area, were only used as a total EV appraisal test because they can amplify the non pathogenesis strains which could be mistake identified. Some selected primers from VP1 area with great variation to identify EV71 type will cause certain undetected error.

This case selected EV71 (SHZH98 strains) 5' UTR homologous conservative area as an alternative amplification area according to the conventional primer design principles and the above descried 3' detailed rules.

```
421 cgaaaaatct actgagctag ttagtagtcc tccggcccct gaatgcggct aatccCaact 481 gcggagcaca cgccctcaag ccagcgggta gtgtgtcgta acgggcaact ctgcagcgga 541
accgactact ttgggtgtcc gtgtttcctt ttatctttat attggctgct tatggtgaca att (SEQ ID NO:33)
```

In order to find out the continuous unmatched or 6-8 bases homo-sequence as much as possible, compared antisense with the sense chain and compared each Entero Virus gene type repeatedly. We found out the sequence gagctag ttagtagtcc in the nt434-448 for pathogenic strains of CA16 and EV71 homologous specific sequence could be as the detecting pathogenic strains upstream Forward primer, the inverted repeat sequence ga accgactactttgggtg whose antisense chain had homo-sequence for all strains common conservative area nt 538-538 could be as a Reward primer of downstream and as reverse transcription primer. All strains conservative area nt458-481: cct gaatgcggctaatc-cCaactg could be used as fluorescence probe sequence, its nt476 becoming C was most of the EV71 strains and becoming T was most of the CA16 strains, but the variation was too close to the 3' end, PCR was not easy to identify the subtype, added stem structure a ttc sequence to the 3' end as improved probe, which could still detect the total strain of the disease. This case used SYBR I real-tim fluorescent RT-QPCR as total pathogenic strains of Entero Virus test kits, and LC Green real-time fluorescence PCR and high melting curve analysis as EV71 and CA16 subtype identification.

So, choose PCR primers for EV pathogenic strains as follows:

```
EV3F:
5'-gag cta gtt agt agt cct c-3' (SEQ ID NO:24)

EV3R:
5'-c acc caa agt agt cgg ttc-3' (SEQ ID NO:29)
```

PS: The underline for homo-sequence bases.

(1) Samples RNA extraction: The preferred choice is herpes fluid and throat swab, or cerebrospinal fluid and blood, after onset 3 days selected anal swab and waste faeces or its cell cultures, waste faeces should be natural precipitation for 10 minutes, add 1 mL of RNA lysate reagent (0.5 mL 4 M GTC liquid and 0.5 mL phenol water) or commercial reagents Trizol to degenerate and crack the 0.1 mL supernatant (or 0.1 g solid specimens), after strong vortex, plus 100 μL chloroform and vortex again, and then do the highest Centrifugation for 10 minutes. The supernatant mix with 3×combining buffer (6 M NaI), then transfer to commercial magnetic microsphere reagent or silica gel purification column (detailed by commercial manual operation), take washing buffer (2M NaI containing 70% EtOH) to wash column twice, eluted by 50 μL dH2O that treated by DEPC, collect centrifugal purification RNA. Or add the same amount isopropyl alcohol as the supernatant and 1/10 volume 2M sodium acetate (PH4.0), store at -20 by 2 hours, centrifugal precipitation, washed by 75% cold ethanol once, dissolved by 50 μL dH2O that treated by DEPC.

(GTC liquid: 4M guanidine thiocyanate dissolved at 65 and 0.1 mM DTT and 0.5% Sarkosyl.)

(2) RT real-time fluorescent PCR:

RT-PCR combined with real-time fluorescent PCR react in single tube.

| | |
|---|---|
| Template | 10 μL |
| Upstream forward primer F(5 μM) | 0.5 μL |
| Downstream reverse primer R(5 μM) | 0.5 μL |
| 10 mM dNTP(+rNTP) | 0.5 μL |
| 10 × Taq buffer | 2.5 μL |
| rTth polymerase | 1.0 μL |
| SYBR Green I (25×) | 1.0 μL |
| RNase inhibitor | 0.5 μL |
| dH2O treated by DEPC | 8 μL |
| total volume | 25 μL |

Add 30 μL mineral oil on the reaction solution surface carefully along the tube wall.

For practices, first prepared 1.5 mL (50 times 15 μL) reaction mixtures without template, that is to say, each ingredient plus 50 times a single reaction volume, vortex and kept portions in 96-well plate or 0.2 mL PCR tubes for 50 times, then added 10 μL DNA/RNA template or analog standard into every well or tube. The average of parallel 5 times 25 μL repeats testing was taken as final Ct value for each sample.

Standard curve and the quality control: Inserted a part of EV 5'-UTR sequence into Enzyme cut pUC19, PUC-EV$_3$L was cloned and generated as simulate positive plasmid quantitative control, the plasmid length is 2.8 kb, MW is $1.8×10^6$, calculating is $3.3×10^8$ copies. Plasmid pUC-EV$_3$L small Minipreped DNA, measured $OD_{260}/OD_{280}$ optical density, calculated DNA content according to 1 $OD_{260}$ equals 50 μg/mL DNA and diluted into 1 μg/mL by TE buffer as quantitative reference standard. Dilute Simulation standard pUC-EV3L as 1 μg/mL×$10^{-2}$, 1 μg/mL×$10^{-3}$, 1 μg/mL×$10^{-4}$, 1 μg/mL×$10^{-5}$, 1 μg/mL×$10^{-6}$, 1 μg/mL×$10^{-7}$, and 1 μg/mL×$10^{-8}$.

The reaction tube was put on the real-time fluorescent PCR instrument (TL988, TL988-type of Xi'an Tianlong company or MJ Inc. DNA Engine OptionTM2) or any other style real-time fluorescent PCR instrument with absorbing wavelength of 480 nm and emitting/detection wavelength of 520 nm. The first 1-5 cycles of reverse transcription RNA denature at 74 for 4 minutes, transcript at 50 for 20 minutes, and then denature DNA at 94 for 2 minutes, and the last 45 cycles of 95 for 20 seconds, 54 for 40 seconds and 72 for 30 seconds. Read fluorescence value at 72. You could do melting curve analysis from 50 to 90 or high resolution melting (HRM) analysis of LC Green real-time fluorescent PCR.

Figure 10:
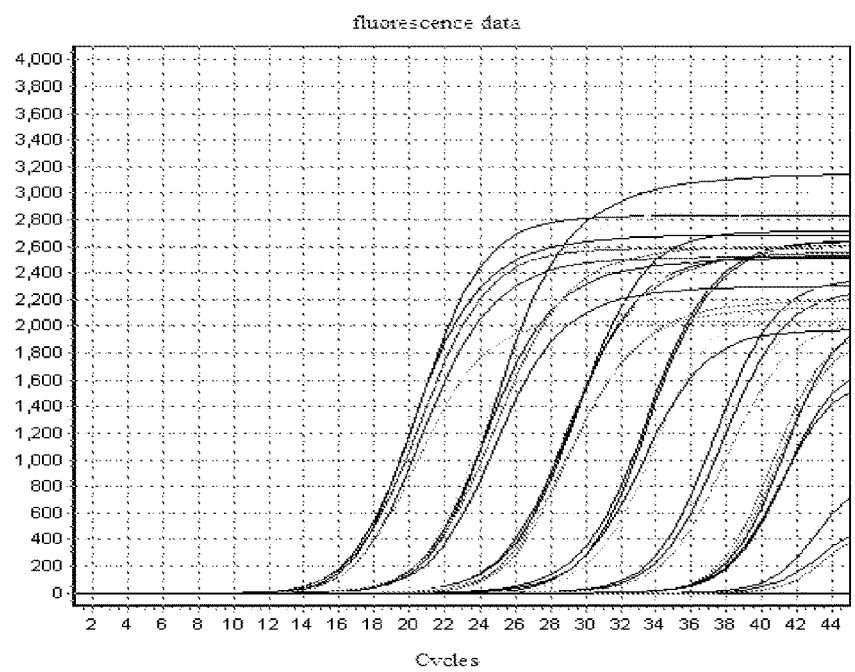
FIG. 10 is the standard curve of standard pEV (0.1 μg/ml) 10 times dilution for enterovirus SYBR Green I real-time fluorescent PCR, the Ct values are 16, 20, 24, 28, 32, 36, 40, baseline, in turn. The corresponding copy numbers are $3\times10^6$, $3\times10^5$, $3\times10^4$, $3\times10^3$, $3\times10^2$, $3\times10^1$, $3\times10^0$, 0 copies per reaction; standard Ct values of dilute parallel 5 repeats coincide completely.

(3) The experimental results analysis (refer to FIG. 10):

| Con: | 10 ng | 1000 pg | 100 pg | 10 pg | 1 pg | 0.1 pg | 10 fg | 0/ml |
|---|---|---|---|---|---|---|---|---|
| Copy | $3 \times 10^6$ | $3 \times 10^5$ | $3 \times 10^4$ | $3 \times 10^3$ | $3 \times 10^2$ | $3 \times 10^1$ | $3 \times 10^0$ | 0 |
| Ct | 16 | 20 | 24 | 28 | 32 | 36 | 40 | baseline |

(DNA plasmid pUC-EV$_3$LStandard, MW: $1.8 \times 10^6$)

Results: the real-time monitoring original data curve (see FIG. 10) was the real-time fluorescence PCR amplification curve for plasmid control simulating positive, five repeats of the intra-batch repeat amplification fluorescence quantitative standard curves were highly consistent, the curves were completely coincident at the early of logarithmic amplification, the inter repeatability is consistent, and even the test of different batch samples can refer to the same quantitative standard curve and their analysis of the results is same. The negative logarithm of test sample initial copy and linear standard curve about amplification Ct values are mostly generated automatically by real-time fluorescence PCR procedure, sample copy number can be automatically converted into concentration. Due to the more drawings and space limitations, the figure of Real-time fluorescent PCR procedure analyzing the experimental results, the figure of melting curve analysis and the figure of LC Green real-time fluorescent PCR test were not displayed. Result judgment: Ct value ≤37 was positive, Ct value ≥39 was negative, Ct37-Ct38 was gray area, and melting Tm value>80 was positive, Tm values ≤76 was negative, otherwise retested. Currently the tests of simulation standard and cultivated EV are accurate and reliable, but the test results of clinical HEV samples have great difference, and the sample scal is still not enough to make a conclusion.

Example II: Human Hepatitis B Virus SYBR Green I Real-Time Fluorescent PCR

Hepatitis B viral Hepatitis (Hepatitis B), caused by the Hepatitis B virus (HBV), is a worldwide infectious disease. The infectious rate of this disease is very high among the crowds in China, which harm people's health greatly. The methods for HBV detection include ELISA, RIA, ECL, immune-fluorescence, nucleic fluorescence quantitative PCR method, etc. The ELISA method has been widely used, but the real-time fluorescent PCR could quantify the amount of HBV gene accurately in HBV infectious patients, which is of vital importance for judging the infectious level of viral replication and infectivity of the virus, as well as monitoring the effect of drug therapy. This example implement real-time fluorescent PCR include: A test of HBV load and B test of hepatitis B virus (HBV) drug-resistance variant (YIDD, YVDD).

A Test of HBV Load:

Hepatitis B virus (HBV) is a partly double-stranded DNA virus, there are mainly three parts of specific conservative district, located in the surface antigen area, X area and Core area respectively. Most of the real-time fluorescent PCR choose the Core area and the surface antigen area as the options. The Core area of the HBV has positive and negative double-stranded DNA, and the HBV antigen surface area only contains a single negative chain which rear part has large amount of secondary structures, affecting the amplify efficiency of PCR. Compare most of the PCR primer for the Core area with one another, we can find that there are still some primers with obvious complement sequences which could accelerate the formation of primer dimer, some of them even don't conform the general principles of primer designation. When used in PCR, most of the PDs start to amplify during the 30 cycle (Ct 30).

Design of Primers for HBV Core Area

We selected the common conservative HBV area as alternative primer sequence according to the conventional primer design principles and the above descried 3' detailed rules, and then proceeded a parallel comparison between the anisense chain sequence and the sense chain sequence, to find out continuous unmatched/same 5-8 bases sequence in a row as much as possible, and optimized a pair of primer under the guidance of reducing the amount of primer dimers. We prepared several pairs of same sequence primers and abandoned others because of their too many continuous GC which could influence the PD and their secondary structure which couldn't amplify the HBV DNA or etc. Finally we utilized the hepatitis B virus (HBV) Core area as the template, and treated a sequence of the HBV core area (CDR: 2306-2444) as the identical ID primer for HBV; here we show 20 bases of each end for the core area (nt: 2306-2444).

AB540584 Core area (nt: 2306-2444)

```
                                        (SEQ ID NO:37)
CAAATGCCCC TATCTTATCA AC-GTCGCAGAAGA TCTCAATCTC

Sequence of optimized HBVc primers
                                        (SEQ ID NO:13)
HBVcF: 5'-at gcc cct atc tta tca ac-3'

(SEQ ID NO:14)
HBVcR: 5'-g att gag atc ttc tgc gac-3'

(SEQ ID NO:19)
(HaBVcR: 5'-g att gag atc tta tgc gac-3')
```

There are only five parallel identical sequence bases (atc tt) between the upstream and downstream primers, the repulsive force is not enough, and background Ct vale was put off 5-6 cycles to 35-36. As a result, we added a same/homo base at the right/3'end of the ID sequence artificially, changed the 13$^{th}$ base c of the downstream HBVcR primer into a of HaBVcR according to the strength of bases' mismatch order and the principle of not influencing the amplification efficiency, after that, the Ct vale of blank background for HBVcF/HaBVcR was put off to 38-39, where the nonspecific amplification Ct vale fall outside the lowest edge scope of specific amplification.

In order to further dominate the nonspecific amplification of HBV real-time fluorescent PCR, reducing or eliminating the background amplification, we also made to use of the antisense As Oligo disturbing technology to the primer's ID, chose the upstream primer HBVcF ID antisense interference oligo-nucleotide HBcFi, whose sequence was 5'-a taa/i2O Me g/ata/i2O Me g/-3', and the $5^{th}$ and $9^{th}$ base g of the sequence was 2'-O-Methyl(OMe)RNA that 3'end closed. Choose the downstream primer to design antisense oligo-nucleotide HBcRi whose sequence was 5'-aga aga tct c-3' aim at the ID and 5'area of the primer, and the $5^{th}$ base g was 2'-O-Methyl RNA antisense, the 3'end of the oligo-nucleotide was closed by label phosphate group (ordered in Shanghai Sangon biological engineering co., LTD after synthesis). Generally it is enough to choose primers for one end of the template to give it As Oligo interference. First of all, we prepared 100 uM primer and antisense As Oligo store liquid (Stock), then diluted them into 1.25 uM primer HBVcF and 1 uM antisense oligo-nucleotide HBcFi as 4×postponed-release primer in use of 20% Dextran (w/v). Or diluted the HBVcR into 5 uM and added equal amount of 4 uM HBcFi. The background Ct vale was put off until the $45^{th}$ cycle after we added equal As Oligo primer.

Used the already known positive serum (clinical tested) as the positive control specimen, chose some strong positive serum, demarcated them with the bought standard DNA, then made 10 folds dilution for them by inactivated negative serum to get standard concentration gradient. Both the positive serum, serums with concentration gradient and negative serum were involved in sample DNA processing. We amplified the total Core area (1900-2450) and 550 by sequence fragment whose sides had enzyme loci, cut the ends by enzyme and cloned them into pUC 19 vector as simulate quantitative contrast DNA (pHBVc), then made 10 folds dilution of pUC19(1 ng/ml) liquid from 0.01 ug/ml for 7 times to get simulate generate gradient quantitative standard samples after methylated them by methylate enzyme, added protective liquid and stored them in −200, took 5 ul stimulate quantitative standard specimens directly for testing.

Adding trace 0.5-0.7 mg/100 ml Poly-Phosphoric Acid (Sigma04101, Poly Phosphoric Acid) to hot start polymerase KlenTaq, Taq (Stoffel fragment)/or Taq (5 U/μl), the negative charge of it could help it bonding to the Taq polymer and inhibiting aggregate abilities of the polymer to insure releasing hot start Taq enzyme activity, which was combined with antisense oligo-nucleotide postponed-release primer to form double hot start model, further insuring the reliability of target specific amplification. Used dUTP instead of dTTP in the dNTP substrate together with a pretreatment by UDG enzyme before PCR, generally we added 10% amount of recombinant rUDG enzyme (1.5 mg/ml) into Taq (5 U/μl)

(1) Processing of Specimen DNA

By one-step boiling method, took 10-100 μl serum, added equal 2×boiling buffer (blended gently the beads before using, sucked by big void tip), blended lightly, put them in boiling water for 10 minutes, high-speed centrifuged for 10 minutes after a 4 short-time cooling, then took out 5 μl of the supernatant. It means that the amount of the DNA had been double diluted.

The weak positive specimen HBV should be precipitated by PEG before using the boiling method, mixed the mixture of 500 μl serum and 500 μl 20% (w/v) PEG salt solution by vortex, high-speed centrifuged for 10 minutes to precipitate the virus, abandon 970 μl supernatant, added 30 μl dH$_2$O to the 30 μl precipitation, and added equal 2×boiling buffer 60 μl, the other steps were ditto to the boiling method, took out 5 μl supernatant to finish the test. But the average recovery rate of PEG precipitation was 60%, quantitative detection of the DNA concentration was equal to being concentrated for 5 folds. Or we can use commercial silica gel purify column or magnetic microsphere kits.

(2×boiling buffer: used reagents such as weak alkali and protein precipitated reagent, etc)

(2) SYBR Green I Fluorescent PCR

We use 25 μl of reactive system, the background fluorescence is very low because the low binding rate between SYBR Green I and single chain as well as the DNA less than 0.1 μg/ml ($10^{10}$ copies), but the binding rate during logarithmic expansion phase can increase for a thousand fold to high concentrate double strands DNA. The sensibility of SYBR Green I PCR is higher than probe method PCR for one order of magnitude because of the strong fluorescent signal. (The fluorescence signal was greatly excess for the 25 μl of reactive system, it can still be reduced to nano-liter system, more suit for reactions on high throughput micro-nano PCR chip).

Prepare the reaction solution according to the follow formula

|  | Single | 10 times |
| --- | --- | --- |
| HaBVcR (5 μM) | 0.5 μL | ×10 |
| dNTP(dU replace dT, 6 mM) | 0.5 μL | ×10 |
| SYBR Green I(25×) | 1.0 μL | ×10 |
| Taq(Hot Start) | 1.0 μL | ×10 |
| 10 × PCR buffer | 2.5 μL | ×10 |
| dH$_2$O | 13 μL | ×10 |
|  | 18 μL | ×10 |

Add 2 μl postponed-release primer HBVcF (1.25 μM) on the bottom of each tube firstly, then add 18 μl reactive mixture to the wall of corresponding tubes near the bottom, after that add 30 μl paraffin oil/mineral oil along the upper wall of the tube, did not blend in case of damaging the postponed-release. The postponed-release primer can be released at 95 during the thermal denature to hot start. The gradient standard specimen and the sample, 5 μl, were added at last, changing tip for each tube, took 5 μl of the sample and injected it below the mineral oil layer carefully, didn't blend after covered the PCR tubes. Short instantaneously centrifuged to sink the residue liquids on the surface of the mineral oil, in case that the colloidal aerosol amplified from the residue liquid might leak out. We also could double the total volume to 50 μl, and so did the postponed-release primer, the reactive mixture and the mineral oil, and took 10 μl sample out for the test. The SYBR Green I dye also could be added in the postponed-release primer, on one hand, it is easy to see solution during the trace sample adding because of the visible color, on the other hand, it can prevent the SYBR Green I dye from leaking out to pollute the laboratory and doing harm to our health through colloidal aerosol. Clinical test kits could also be compounded as 5× reactive mixture, 10× reactive mixtures to further reduce the operators' workload.

Each test could be parallel 2-3 repeats×25-50 μl, and then calculated the average Ct value, analyzed statistical results.

Loaded the reactive tube on a real-time fluorescent PCR instrument (Xi'an Tianlong company TL988 type instrument, the one whose absorbing light length is 480 nm and emitting light length is 520 nm), run the program according to the manual. First proceed a pre-reaction at first, 50 for 2 minutes-94 for 4 minutes, Then run for 45 cycles at 94 20-30 sec, 54 for 30 sec, 72 for 20-30 sec. Read the fluorescent value at 72 and set melting curve analysis among 50-90. Although the reactive solution was covered by mineral oil, it was also necessary for the PCR instrument to set hot-lid in case that the residue reactive liquid on surface of the mineral oil evaporated to the cap of PCR tube and shut out the light path after they changed into condensate water, influencing the fluorescent value, but we could run the PCR program before the temperature of the lid increased to the setting point 105 if we set a hot-lid. Start the PCR thermal preheat at 95 for 4 minutes to make the residual liquid on the surface of mineral oil evaporating and squeezing out the tube as more as possible. We could also process regular endpoint PCR for 35 cycles without adding the SYBR Green I dye, replace the hot-lid by mineral oil, and test the products with 1.5%-2% agarose gel electrophoresis (the fluorescent dyes could affect the electrophoretic mobility during electrophoresis).

(3) Analysis of the Results

Simulate positive gene plasmid pHBcore (MW2.1×10$^6$) quantitative standard was gradient diluted by 10 folds, the conversion between the serum concentration and the copy together with the Ct value linear relationship of the SYBR Green I real-time fluorescence PCR can be seen in the table below.

| Ct | 16 | 19.3 | 22.6 | 26 | 29.5 | 33 | 37 |
|---|---|---|---|---|---|---|---|
| Copy | 3 × 10$^9$ | 3 × 10$^8$ | 3 × 10$^7$ | 3 × 10$^6$ | 3 × 10$^5$ | 3 × 10$^4$ | 3 × 10$^3$ |
| Con. | 10 ng | 1000 pg | 100 pg | 10 pg | 1 pg | 0.1 pg | 10 fg/ml |

DNA plasmid pHBcore standard, MW: 2.1 × 10$^6$

Figure 11:
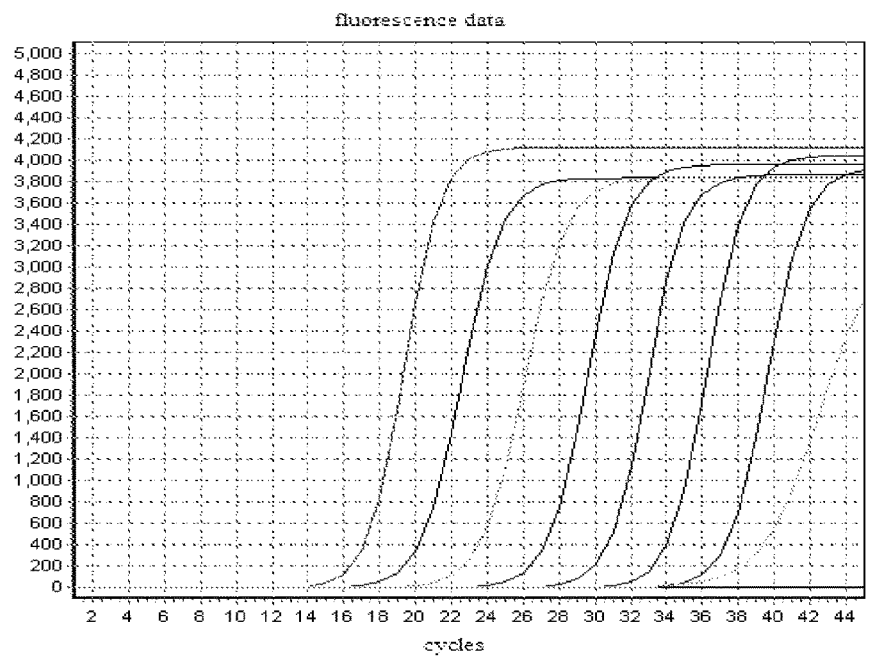
FIG. 11 is the hepatitis B virus (HBV) standard quantitative curve: uses HBV core antigen plasmid control pUC-HBcore 0.1 μg/ml about $3\times10^{10}$ copies/ml to do the SYBR Green I quantitative standard curve of 10 folds dilution of template, the left the first amplification curve is 0.1 μg/ml template, about $3\times10^{10}$ copies, followed by 10-fold dilution, the last amplification curve is the background control of no template, whose Ct values are 12.5, 16, 19.5, 22, 25.5, 29, 32.5, 36, 38 line, in turn. The background control Ct value is almost a straight line within 45 cycles, having no amplification Ct value. The gradient distribution of all quantitative standard curves spaces the interval of 3.3 Ct values, especially low copy gradient pulls wider, whose amplification efficiency are 100%. Repeatability is very good for many times.

The results of SYBR Green I real-time quantitative PCR can be seen in FIG. 11, making the standard quantitative curve of 10 folds dilution template, the first amplified curve stand for 0.01 μg/ml template (about 10$^6$ copies/ml), followed by 10 folds diluted samples, the last amplified curve was for no template background contrast who had no amplified Ct value among 45 cycles.

Load 5 μl sample after the serum being added by equal boiling buffer, which was double diluted compared with 5 μl standard specimens. The copy number or international units of the sample coming from the Ct value of standard curve should be double calculated, following the table blew for samples. Ct value ≤37 means positive, Ct value>38 means negative. Melting curve analysis, the positive Tm value is 87, Tm<78 means negative. (Calculated according to the standards, the test in this invention shown that the 6 copies number is approximately equal to 1 international unit.)

| CT | 16 | 19.3 | 22.6 | 26 | 29.5 | 33 | 37 |
|---|---|---|---|---|---|---|---|
| IU/mL | 10$^9$/mL | 10$^8$/mL | 10$^7$/mL | 10$^6$/mL | 10$^5$/mL | 10$^4$/mL | 10$^3$/mL |
| Co | 15-20 ng | 2000 pg | 200 pg | 20 pg | 2 pg | 0.2 pg | 15-20 fg/mL |

HBV DNA MW: 1.57 × 10$^6$~2.09 × 10$^6$ (size of particles of HBV are different)

The HBV DNA quantitative standards (lot 0711) positive reference samples and quantitative reference L1 to L5 bought from National Test Institute of China for the Control of Pharmaceutical and Biological Products. Results of the standard test agreed with the standard value, all of the negative reference shown baseline reaction. More than 500 cases from Beijing YouAn Hospital, The third peoples hospital of Henan province, And the armed police general hospital in Henan province were clinical-tested and there are more than 450 cases had positive results. We used "hepatitis B virus nucleic acid quantitative detection kits" product by Shanghai clone high technology Co., Ltd, its lot of SFDA: 520040029, valid until 20130607, as a contrast agent. Verify by "hepatitis b virus nucleic acid quantitative detection kits" from the third party of Roche molecular diagnostics company to test sample with inconsistent results, its lot of SFDA:2008 3403079, valid for 48 month, for retest. Results summary: we tested Hepatitis B HBeAg positive and Hepatitis B HBeAg negative serums, the sensitivity of hepatitis b virus (HBV) nucleic acid detection was 95.45%, higher than the contrast 92.04%. The specificity was 99.28%, contrast 98.53%. The false negative rate was 4.55% contrast to 7.96%. The false positive rate was 0.72% contrast to 1.47%. The total coincidence rate of results between the demarcate reagent and the ELISA test for Hepatitis B HBeAg was 95.58%. The total coincidence rate of results between "HBV hepatitis b virus nucleic acid fluorescent quantitative PCR detection kit" researched/invited by our invention and the ELISA test for Hepatitis B HBeAg was 97.59%, higher than the total coincidence rate 95.58% of the contrast reagent.

B. Detect the hepatitis B virus (HBV) drug-resistance variant:

The treatment of hepatitis B virus with α-interferon and nucleotide antiviral drugs Lamivudine, however, lamivudine treatment easy to produce drug resistance mutation strains for the effect of drug selection. According to clinical statistic, there will be 14-32% resistance of serum e Antigen positive patients that treated by lamivudine one year. After long-term treatment, the resistance increases to 38%, 49% and 66% in the second, the third and the fourth year (Karayianmis p., Journal of Antimicrobial Chemotherapy 2003, 51: p 761-785). The mutations of drug resistance strains mainly happened in PoL/RT fragments of HBV Polymerase activity area (349-692 aa, rtl-rt344), commonly tyrosine-methionine-aspartate-aspartate YMDD mutation. By the variation of YMDD to YIDD (rtM204I) or YVDD (rtM204V), YVDD often accompanied by rtL180 M variation (Lai C L., et al., Clin Infect Dis, 2003, 36: p 687-696). And the detection of serum HBV RNA YMDD mutation is earlier than that of HBV DNA YMDD mutation (Hatakeyama. et. al., Hepatology, 2007, 45-5: p 1179-86). Therefore, the detection of HBV YMDD mutation would be significant, especially in the RNA YMDD mutation to adjust the treatment plan, rational use of drugs, using adefovir instead of lamivudine resistance ineffective treatment instant. Select the hepatitis B virus (HBV) contains PoL/RT fragment gene as template, select a sequence of hepatitis B virus polymerase activity area or S area (CDR: 596-764) as target specific sequences of nucleic acid amplification for HBV drug-resistance variant. Show about 20 bases of PoL/S area (nt: 596-764) of <u>YMDD</u>, YIDD, YVDD sequence respectively as follows.

```
GCA CCT GTA TTC CCA TCC CAT C(SEQ ID NO:31)------TAT ATG GAT GAT GTG GTATTG GGG GCC(SEQ ID NO:39)

GCA CCT GTA TTC CCA TCC CAT C(SEQ ID NO:31)------TAT ATT GAT GAT GTG GTA TTG GGG GCC(SEQ ID NO:40)

GCA CCT GTA TTC CCA TCC CAT C(SEQ ID NO:31)------TAT GTG GAT GAT GTG GTA TTG GGG GCC(SEQ ID NO:41)
```

(The black base represents point mutation).

Single nucleotide mutation detection applied ARMS (Newton, C. R. et al, 1989, Nucleic Acids Res, 17:2503)

technology to design primer, single point mutation at one primer 3' end make mutations sequence selective amplification, but single-base mutation is not enough to restrain the wild not mutation sequence amplification, so often add an artificial mutation bases at the second/third position from primer 3' end, little mismatch as purine replaced purine and pyrimidine replaced Pyrimidine will mild affect the mutation amplification and the wild will not expand as far as possible. In order to control PD nonspecific amplification interference of single nucleotide mutation PCR, one side primer in combination with 5' end intra molecular reverse primers interference, mark reporter 6-FAM-dT or Cy3-dT to the third from bottom to the ID base and mark quencher dabcyl or quencher sequence to its 5' end. The other primer is common primer not 5' end intra molecular reverse primer. So double fluorescent marked primers double single nucleotide mutation real-time fluorescence PCR comes true.

So, choose HBV YMDD resistant mutant strains PCR primers as follows:

YMDDF:
5'-cct gta ttc cca tcc cat c-3' (SEQ ID NO:42)

(SEQ ID NO:43)
5YIDR:
5'dabcyl-t gtg gta-ccc caa wac cac a/6-FAM-dT/c at*t* a-3'

(SEQ ID NO:44)
5YVDR:
5'dabcyl-*t gat gtg*-c caa wac cac atc a/Cy3-dT/c

*t*ac-3'

(The underline is 5' end intra primer reverse interference As Oligo sequence, the bold italic t represents artificial little mismatch mutation).

The processing of DNA in the sample was same to HBV load testing, and the total RNA processing of the sample is same to the example I. The operation of Real-time fluorescence PCR adopted fluorescent primer includes compound reactive mixture, primer, fluorescent primer, substrates dNTP, buffer, Taq polymerase. The kinds and amounts of the kits were same as above HBV load testing. Analysis samples on the real-time fluorescent PCR instrument with 2-4 fluorescence channels, the length of absorbing light is 49 nm and detecting light is 520 nm to detect YIDD, absorbing light for 640 nm and detecting light for 670 nm to test YVDD, operate the instruction according to the manual. Here are reactive conditions of common dye method real-time fluorescence PCR: pre-reaction 50 for 2 minutes-95 for 4 minutes, followed by 45 cycles, 94 for 20-30 sec, 54 for 30 sec, 72 for 20-30 sec, read the fluorescence at 72, at the same time we set up 50-90 melting curve analysis. It came out that the Ct value from selectively total amplified load of YIDD and YVDD were put off for less than one cycle, the amplified efficiency almost didn't decrease any more. The mutative primers had only thousandth amplification for the wild template without mutation. (Data not show)

Example III: Improved TagMan Probe of Real-Time Fluorescence PCR for HBV

Probe method real-time fluorescent PCR is mainly represented by TaqMan probe, also include the MGB probe who increased binding force and LNA locked nucleic acids) bases probe. The increased signal of amplification products is detected through fluorescent probes with labeling and quenching dyes. Usually, the 5'end of the probe is marked with reporting dyes such as FAM, VIC, NED etc, the 3'end of the probe is marked with quenching dyes (TAMRA, DABCYL & BHQ etc). The quenched probe can give out fluorescence of free fluorescent groups after being hydrolyzed from the 5'end by the Taq polymerase enzyme. The designation of the probe should follow these principles: 1) the Tm of probes should higher than the primer at least for 10, 2) bases of the probe's 5'end should not be G because the G base could also quench the fluorescence of the reporting dye after hydrolysis, 3) the amount of G bases should not surpass C, 4) Avoid single nucleotide string, especially for G, 5) sequences rich in AT should increase the length to meet the requirements of the Tm value, but the probe must <40 nt, otherwise the quenching efficiency will be low which can lead to a high background, 6) during annealing process of probe, the 5'end should be as close as possible to the primer without overlap, in other words, it should at least one base far from the primer's 3' end, 7) when detect single base mutations (SNPS), the mutational point should better set in the middle of the probe or near the 5'end as far as possible, make the probe as short as possible, 8) when does mRNA express analysis, the probe should include Extron /-/ Extron boundaries, 9) the 3'end of the probe must be closed by quenching agent to prevent the probe from expending during the PCR amplification.

Our invention adopts improved TaqMan probe in the real-time fluorescent PCR, the 3'end of the probe is added 6-8 bases complementary with the 5'end artificially, in order to make sure that the 5'end quenching radical close to the 3'end reporting radical. Integrate advantages of TaqMan and Molecular Beacon technology, the improved probe selects a representative sequence (nt: 2374-2405) of the target gene (near the downstream primer), the 5'end of the special target sequence (complementary sequence) is labeled by report fluorescent FAM, make use of the taq enzymes' 5'-3' circumscribed hydrolysis to hybridize the probe for the release of reporting dye. The 3'end of the probe is added several bases complementary with the 5'end and then labeled with the quenching radical BHQ-1, the end of the probe can form a stem-loop structure familiar with Molecular Beacon because of the internal complementation. Not only can the probe, who inherits the low background property of Molecular Beacon and the sensitive and specific advantages of TaqMan, reduce the non-specific product traced from the hybridization of primer and probe, it can also reduce the amount of background fluorescence for about 2-4 folds.

This example also featured a sequence of the hepatitis B virus (HBV) Core area (CDR: 2306-2444) to be the nucleic acid amplification target specific sequence of the HBV replacement primer, here are 20 bases of the 10 Core area's each side: AB540584 Core area (nt:2306-2444)

(SEQ ID NO:37)
CAAATGCCCC TATCTTATCAAC-GTCGCAGAAGA TCTCAATCTC

Base on the same general select principle of primer to minimize the amount of primer dimers as a comprehensive consideration; we designed the primer of the real-time PCR with probe for HBVcore.

Here are the sequences of the primer:

```
THBVFc:
5'-ca aat gcc cct atc tta tca ac-3' (SEQ ID NO:45)

THBVRc:
5'-gag att gag atc ttc tgc gac-3'(SEQ ID NO:46)
```

The F stands for the upstream primer sequences, R stands for downstream direct target specific primer, the bolds on behalf of the same/homo sequence bases.

Figure 12:
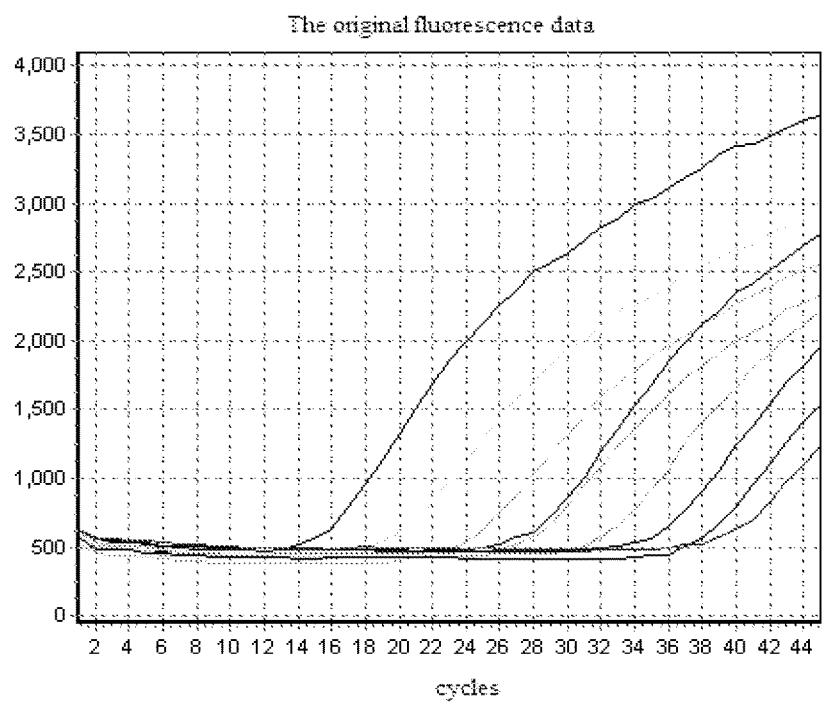
FIG. 12 is the standard curve of standard pHBcore (1 μg/ml) 10 folds dilution for Hepatitis B improved TaqMan real-time fluorescence PCR, the results of Ct values are 15.5, 19, 23, 26.5, 31, 35, 37 in turn, and background control Ct value is 39, whose corresponding copy number are $3\times10^6$, $3\times10^8$, $3\times10^7$, $3\times10^6$, $3\times10^5$, $3\times10^4$, $3\times10^3$/ml, and background 0 copies/ml, the sensitivity is just lower an order than dye method.

Design antisense oligo-nucleotides interference PNA for THBVFc primer and its sequence is 5'-g ttg a-3' (Ordered from PD Biocem Co. Ltd after compounding), then we join the antisense oligo-nucleotide one over one thousand volume of THBVFc (5 uM) in the system to make sure the concentration is 100 pM in the primer. The THBVRc was diluted to 2.5 uM as slow-release primer by 18% Dextran (w/v) and 0.1M NaCl solution.

Sequence of the probe: cc tag aag aag aac tcc ctc gcc tcg cag acg, we use its antisense sequence and add several 3'end stem structure bases,

```
TqHBc:
5'-FAM cgt ctg cga ggc gag gga gtt ctt ctt cta gg cac acg BHQ-1-3'
```

(1) DNA Extraction of Clinical Blood Specimens

Centrifugal column method: take 100 ul serum to Ep tube, add 100 ul boiling buffer for the sample, boil for 10 minutes in boiling water or metal bath, high speed centrifugal for 10 minutes, take the supernatant into a commercial DNA purify column (nucleic acid silicon membrane adsorption column) and add 6M NaI fluid for 3 times as much as the supernatant's volume, plus washing buffer (2 M NaI liquid containing 70% EtOH) to centrifugal wash twice, add 50 ul $dH_2O$ and centrifugal to collect purified samples. (The boil supernatant can be directly used as the template for PCR).

Micro magnetic beads: make use of guanidine hydrochloride/guanidine thiocyanate to lysate the sample, the nucleic acid would combine to the siliconization polystyrene surface hydroxyl of the micro magnetic microspheres under the condition of high concentration of 4M guanidine salt (Melzak et al, 1996), and then washing with the buffer whose pH is less than 6, eluting with the buffer whose pH is higher than 8.5. As time went by, phenol-chloroform extraction method and silicon liquid adsorption centrifugal column method have been gradually replaced by this method.

Take 100 ul serum into a 1.5 ml tube, add same volume of guanidine salt lysates liquid for 5 minutes, after the append of 0.8 ml dilute neutralization buffer, we add 25 ul paramagnetic silica nano-particle microspheres, then place the tube in a magnetic separate tube rack to adsorb magnetic microspheres, abandon the unproductive liquid, add 0.8 ml washing buffer again, finally add 50 ul elute buffer for the magnetic microsphere to collect DNA.

(2). TaqMan Real-Time Fluorescence PCR Reaction

The PCR use TaqMan can only release one fluorescent radical at most each cycle, its fluorescence intensity is far lower than the SYBR Green I fluorescent method (every 3-4 by DNA combined with one SYBR Green I molecule). As a result, the TaqMan method had better use a larger volume of react system for 50 ul to make sure that the PCR instrument could accept enough fluorescence signal. Without any doubt, it also increased the baseline fluorescence of PCR proportionally, additive bases complementary with the bases of the 5'end at the 3'end of the probe made the reporting radical and the quenching radical nearer to each other, at the same time reduced the background fluorescence for 2-4 folds without influence the specific amplification. First of all, we add 2 ul postpone-release primer R (2.5 uM) who could be hot started and avoid product aerosol pollution in every react tube. And then compound reactive mixture contains no template and primer in a 1.5 ml Ep tube according to the following formula.

| | Single reaction | ×25 mix |
|---|---|---|
| 1. Upstream forward primer(5 uM) | 1 μL | 25 μL |
| 2. dNTP (dU replace dT, 4 mM) | 1 μL | 25 μL |
| 3. TaqMan probe (2.5 uM) | 1 μL | 25 μL |
| 4. Taq enzyme (Hot start) | 2 μL | 50 μL |
| 5. 10 × PCR buffer | 5 μL | 125 μL☆ |
| 6. $dH_2O$ | 28 μL | 0.7 mL |
| +2 ul slow-release primer = | 50 μL | 0.95 mL |

(☆Fluorescent probe will gradually decay; old probe can add more volume accordingly)

The ×25 reaction mixture by a total volume of 0.95 ml compounded before would be packed in the PCR tube/or 12 pipe line tube with postponed-release primer, 38 ul per tube and for 25 tubes. One of the tubes add 10 ul purified water $dH_2O$ as negative control for the PCR system, and then put 50 ul mineral oil carefully and slowly along the wall on the surface of the liquid to seal the system, give them short transient centrifugations and remember that do not blend them in case of damaging the postponed-release effect.

We add 10 ul sample in the PCR tube contained 2 ul postpone-release primer R and 38 ul reaction mixture, and then slowly and carefully add 50 ul mineral oil on the surface of the liquid. To ensure the reliability of the result, we must set up positive control and negative control, as well as 1-6 quantitative calibration items (depending on the need of the quantitative test). The reference of the test also participates in the extract process of DNA, dilute the simulate positive sample (0.1 ug/ml) for 10 folds, for example we can add 10 ul standard item in 90 ul $dH_2O$, aspirate 10 ul from it and add to next 10 folds dilution, then just do it successively.

Each test has 2-3 50 ul repeats and use the average Ct value, and then analysis the statistical results.

The Standard Curve

Simulate standard 0.1 ug/ml, 0.1 ug/ml$\times10^{-1}$, $\times10^{-2}$, $\times10^{-3}$, $\times10^{-4}$, $\times10^{-3}$, $\times10^{-6}$ dilute point. Calculate them by pUC-HBcore (3.36 kb and MW=$2.1\times10^6$, 1 ug=$2.8\times10^{11}$ copy) we would get copies of the gradient standard molecule: $5.6\times10^9$/ml, $5.6\times10^8$/ml, $5.6\times10^7$/ml, $5.6\times10^6$/ml, $5.6\times10^5$/ml and $5.6\times10^4$/ml.

Put reactive tubes on a real-time fluorescent PCR instrument (adjust the length of the absorbing light FAM: 480 nm detecting light: 520 nm). Run the program according to the manual; go on a pre-reaction at first, 50 for 2 minutes-94 for 2 minutes. Then run the PCR for 40 cycles: 94 30 sec, 58 60 sec, read the fluorescence value at 58. If the residue reactive liquid on surface of the mineral oil evaporates to the tube cap, it would block the light path, as a result, we still need to set the hot-lid and run the PCR program before the temperature of the lid start increasing.

(2) Analyzing for the Experimental Results

HBV core antigen plasmid control pUC-HBcore 0.01 ug/ml for about $10^9$ copies/ml, compound a standard quantitative curve after 10 folds dilution, the first amplify curve on the left is 0.01 ug/ml template for about $10^9$ copies, followed by 10 folds dilution, the last amplify curve comes from a background contrast without template whose Ct value is a straight line during 40 cycles with no amplification (attached FIG. 12). All the results of the negative reference are baseline reactions. The repeatability is pretty well for many times.

The results of HBV DNA standard substance (batch 0711) positive reference samples and quantitative reference bought from National Test Institute of China for the Control of Pharmaceutical and Biological Products are consistent to each other, all negative reference show baseline reaction. 99% results of 500 positive clinical specimens are agree with the results from Shanghai clones high technology Co., Ltd, there was no false positive reaction among all kinds of negative serum. The repeatability is pretty well for many times.

The primer middle sequence interference PCR technology put forward by this invention has been described by implementation examples, and the related technical personnel can do some alteration or appropriate change and combination under the circumstances that don't break away from the details, spirit and scope of the primer middle sequence interference PCR technology described by this essay, in order to achieve the technical invention. Specifically, all similar substitutions and alterations are obvious to technologists of this realm, and all of them are regarded as spirits, scopes and details of this invention.

What is claimed is:

1. A method for inhibiting primer dimer formation and non-specific amplification of a target sequence therefrom in a polymerase chain reaction (PCR), the method comprising preparing a PCR reaction system for amplifying the target sequence, said PCR reaction system comprising: (a) a first primer and a second primer which, when aligned in the 5' to 3 direction, share an identical Intermediate Domain (ID) sequence of 5-9 consecutive bases, wherein both primers comprise a 3' region configured to specifically bind and amplify the target sequence; (b) a 5' antisense sequence of 5-7 consecutive bases, which antisense sequence is complementary to said Intermediate Domain (ID) sequence, wherein the antisense sequence is configured to competitively bind said intermediate Domain to disturb polymerization between the primers, is configured to bind to the ID sequence intra-molecularly such that the first and/or second primer is folded, and does not affect the primers specifically binding and amplifying the target sequence while inhibiting primer dimer formation and non-specific amplification therefrom.

2. The method of claim 1, wherein in the 3' to 5' direction, location of the ID sequence on the primer sequences starts from the fourth or fifth base from the 3' terminal OH end of the primer sequences.

3. The method of claim 1, wherein in (a), the 3' end regions of the primers do not contain two or more bases that are complementary between the primers.

4. The method of claim 3, wherein the first one or two bases at the 3' end regions of the primers do not contain any base that is complementary between the primers.

5. The method of claim 3, wherein the primers' last base is C or A at the 3' terminal OH ends.

6. The method of claim 1, wherein in (a), the method further comprises using a single-stranded DNA binding protein (SSB) in the amplification of the target sequence.

7. The method of claim 1, wherein in (a), said first primer and said second primer which, when aligned in the 5' to 3' direction, share an identical Intermediate Domain (ID) sequence of 6-8 consecutive bases.

8. The method of claim 7, wherein in (a), the identical ID sequence comprises a mutation compared to the target sequence or complementary sequence thereof.

9. The method of claim 7, wherein in (a), the identical ID sequence comprises a modified base.

10. The method of claim 9, wherein the modified base is an RNA base, a 2'-F RNA base, 5F-dU, 5Br-dU, 8-OH-dG, or 8-OH-dA.

11. The method of claim 1, wherein in (a), the second and third bases from the 3' terminal OH ends of the primers are not CG/GC.

12. The method of claim 1, wherein in (b), the antisense sequence comprises 2'-O-Methyl (OMe) RNA, 2'-O-methoxy-Ethyl (MOE) RNA, 2'-Amino-RNA, 2'-Fluoro-RNA, 2'-O, 4'-C-methylene bridge RNA, and PNA (peptide nucleic acid), Morpholino, or N3'→N5' Phosphoramidate.

13. The method of claim 1, wherein the PCR reaction system further comprises dUTP instead of dTTP, a mineral oil sealing condition, and an uracil-DNA glycosylase (UDG) to degrade leaked products that cause colloidal aerosol cross-contamination, wherein said preparing a PCR reaction system comprises:
dissolving the primer in 20% (w/v) Dextran pre-added to the bottom of a container for the PCR; adding other PCR reagents and the mineral oil sealing in order and allowing the PCR reaction to settle; and denaturing the PCR reaction system by heat to release the primer into the PCR reaction to initiate amplification, wherein the residual above the mineral oil sealing without the primer cannot be amplified and only contains leaked products that can be degraded by UDG.

14. The method of claim 13, wherein a primer of the PCR reaction is reversibly immobilized on a solid support and is released into the PCR reaction to initiate amplification.

15. The method of claim 1, wherein the first primer comprises the ID sequence and the anti-sense sequence complementary to the ID sequence while the second primer does not, or vice versa.

16. The method of claim 15, wherein the primer comprising the ID sequence and the anti-sense sequence is fluorescently labeled, and wherein a base from the third base from the 3' terminal OH end of the primer to a base in the ID sequence is labeled with a fluorescence reporter, while the 5' terminal COOH end of the primer is labeled with a fluorescence quencher, or vice versa.

17. The method of claim 16, wherein the fluorescence reporter comprises 6-FAM-dT or Cy3-dT, and the fluorescence quencher comprises dabcyl or 5' dG quenching base.

\* \* \* \* \*

SEQUENCE LISTING

<160> NUMBER OF SEQ ID NOS: 47

<210> SEQ ID NO 1
<211> LENGTH: 19
<212> TYPE: DNA
<213> ORGANISM: Artificial Sequence
<220> FEATURE:
<223> OTHER INFORMATION: Synthetic construct

<400> SEQUENCE: 1
caacctccaa tcactcacc                                              19

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
agattgacga tatgggtgag                                             20

<210> SEQ ID NO 3
<211> LENGTH: 19
<212> TYPE: DNA
<213> ORGANISM: Artificial Sequence
<220> FEATURE:
<223> OTHER INFORMATION: Synthetic construct

<400> SEQUENCE: 3
cctccaatcg aaggagaaa                                              19

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
tccaactgct cttttttctc                                             20

<210> SEQ ID NO 5
<211> LENGTH: 19
<212> TYPE: DNA
<213> ORGANISM: Artificial Sequence
<220> FEATURE:
<223> OTHER INFORMATION: Synthetic construct

<400> SEQUENCE: 5
gggggagcac ccacgtgtc                                                    19

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
gaagattgac gatatgggtg                                                   20

<210> SEQ ID NO 7
<211> LENGTH: 18
<212> TYPE: DNA
<213> ORGANISM: Artificial Sequence
<220> FEATURE:
<223> OTHER INFORMATION: Synthetic construct

<400> SEQUENCE: 7
ttctaggggg agcaccca                                                     18

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
tgacgatatg ggtgaggcag                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
ccctgtgagg aactactgtc                                                   20

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
ctgcagacag ttttcagtga g                                                 21

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
gagttgtcgg ttccgatgag                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
acgttcactc ctgacgacaa                                           20

<210> SEQ ID NO 13
<211> LENGTH: 19
<212> TYPE: DNA
<213> ORGANISM: Hepatitis B Virus

<400> SEQUENCE: 13
atgcccctat cttatcaac                                            19

<210> SEQ ID NO 14
<211> LENGTH: 19
<212> TYPE: DNA
<213> ORGANISM: Hepatitis B Virus

<400> SEQUENCE: 14
gattgagatc ttctgcgac                                            19

<210> SEQ ID NO 15
<211> LENGTH: 18
<212> TYPE: DNA
<213> ORGANISM: Artificial Sequence
<220> FEATURE:
<223> OTHER INFORMATION: Synthetic construct

<400> SEQUENCE: 15
catggtgctg gtgaacac                                             18

<210> SEQ ID NO 16
<211> LENGTH: 18
<212> TYPE: DNA
<213> ORGANISM: Artificial Sequence
<220> FEATURE:
<223> OTHER INFORMATION: Synthetic construct

<400> SEQUENCE: 16
ggacgtgctg gtgtctac                                             18

<210> SEQ ID NO 17
<211> LENGTH: 18
<212> TYPE: DNA
<213> ORGANISM: Artificial Sequence
<220> FEATURE:
<223> OTHER INFORMATION: Synthetic construct

<400> SEQUENCE: 17
catgtccgag ccaaacac                                             18

<210> SEQ ID NO 18
<211> LENGTH: 18
<212> TYPE: DNA
<213> ORGANISM: Artificial Sequence
<220> FEATURE:
<223> OTHER INFORMATION: Synthetic construct

<400> SEQUENCE: 18
cacaagtggt cgtggtac                                             18

<210> SEQ ID NO 19
<211> LENGTH: 19
<212> TYPE: DNA

```
<213> ORGANISM: Artificial Sequence
<220> FEATURE:
<223> OTHER INFORMATION: Synthetic construct

<400> SEQUENCE: 19
gtccccaacc tccaatcac                                                    19

<210> SEQ ID NO 20
<211> LENGTH: 20
<212> TYPE: DNA
<213> ORGANISM: Artificial Sequence
<220> FEATURE:
<223> OTHER INFORMATION: Synthetic construct

<400> SEQUENCE: 20
gaggacaaga ggttggtgag                                                   20

<210> SEQ ID NO 21
<211> LENGTH: 22
<212> TYPE: DNA
<213> ORGANISM: Artificial Sequence
<220> FEATURE:
<223> OTHER INFORMATION: Synthetic construct

<400> SEQUENCE: 21
gcacctgtat ttaaggccca tc                                                22

<210> SEQ ID NO 22
<211> LENGTH: 21
<212> TYPE: DNA
<213> ORGANISM: Artificial Sequence
<220> FEATURE:
<223> OTHER INFORMATION: Synthetic construct

<400> SEQUENCE: 22
ggcccccaac cggaattcat c                                                 21

<210> SEQ ID NO 23
<211> LENGTH: 19
<212> TYPE: DNA
<213> ORGANISM: Artificial Sequence
<220> FEATURE:
<223> OTHER INFORMATION: Synthetic construct

<400> SEQUENCE: 23
gattgagatc ttatgcgac                                                    19

<210> SEQ ID NO 24
<211> LENGTH: 19
<212> TYPE: DNA
<213> ORGANISM: Artificial Sequence
<220> FEATURE:
<223> OTHER INFORMATION: Synthetic construct

<400> SEQUENCE: 24
gagctagtta gtagtcctc                                                    19

<210> SEQ ID NO 25
<211> LENGTH: 18
<212> TYPE: DNA
<213> ORGANISM: Artificial Sequence
<220> FEATURE:
<223> OTHER INFORMATION: Synthetic construct

<400> SEQUENCE: 25
acccaaagta gtcggttc                                                     18
```

```
<210> SEQ ID NO 26
<211> LENGTH: 19
<212> TYPE: DNA
<213> ORGANISM: Artificial Sequence
<220> FEATURE:
<223> OTHER INFORMATION: Synthetic construct

<400> SEQUENCE: 26
agtagtcctc cggcccctg                                                  19

<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
agtagtcggt tccgctgcag                                                 20

<210> SEQ ID NO 28
<211> LENGTH: 19
<212> TYPE: DNA
<213> ORGANISM: Artificial Sequence
<220> FEATURE:
<223> OTHER INFORMATION: Synthetic construct

<400> SEQUENCE: 28
actgagctag ttagtagtc                                                  19

<210> SEQ ID NO 29
<211> LENGTH: 19
<212> TYPE: DNA
<213> ORGANISM: Artificial Sequence
<220> FEATURE:
<223> OTHER INFORMATION: Synthetic construct

<400> SEQUENCE: 29
acggacaccc aaagtagtc                                                  19

<210> SEQ ID NO 30
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 7, 12
<223> OTHER INFORMATION: n = any nucleotide

<400> SEQUENCE: 30
gggatanaat an                                                         12

<210> SEQ ID NO 31
<211> LENGTH: 22
<212> TYPE: DNA
<213> ORGANISM: Artificial Sequence
<220> FEATURE:
<223> OTHER INFORMATION: Synthetic construct

<400> SEQUENCE: 31
gcacctgtat tcccatccca tc                                              22

<210> SEQ ID NO 32
```

```
<211> LENGTH: 21
<212> TYPE: DNA
<213> ORGANISM: Artificial Sequence
<220> FEATURE:
<223> OTHER INFORMATION: Synthetic construct

<400> SEQUENCE: 32
ggcccccaat accacatcat c                                              21

<210> SEQ ID NO 33
<211> LENGTH: 183
<212> TYPE: DNA
<213> ORGANISM: Entero Virus
<220> FEATURE:
<223> OTHER INFORMATION: Synthetic construct

<400> SEQUENCE: 33
cgaaaaatct actgagctag ttagtagtcc tccggcccct gaatgcggct aatcccaact    60
gcggagcaca cgccctcaag ccagcgggta gtgtgtcgta acgggcaact ctgcagcgga   120
accgactact ttgggtgtcc gtgtttcctt ttatctttat attggctgct tatggtgaca   180
att                                                                 183

<210> SEQ ID NO 34
<211> LENGTH: 19
<212> TYPE: DNA
<213> ORGANISM: Entero Virus

<400> SEQUENCE: 34
gagctagtta gtagtcctc                                                 19

<210> SEQ ID NO 35
<211> LENGTH: 19
<212> TYPE: DNA
<213> ORGANISM: Entero Virus

<400> SEQUENCE: 35
cacccaaagt agtcggttc                                                 19

<210> SEQ ID NO 36
<211> LENGTH: 24
<212> TYPE: DNA
<213> ORGANISM: Entero Virus

<400> SEQUENCE: 36
cctgaatgcg gctaatccca actg                                           24

<210> SEQ ID NO 37
<211> LENGTH: 43
<212> TYPE: DNA
<213> ORGANISM: Hepatitis B Virus

<400> SEQUENCE: 37
caaatgcccc tatcttatca acgtcgcaga agatctcaat ctc                      43

<210> SEQ ID NO 38
<211> LENGTH: 22
<212> TYPE: DNA
<213> ORGANISM: Hepatitis B Virus

<400> SEQUENCE: 38
gcacctgtat tcccatccca tc                                             22
```

```
<210> SEQ ID NO 39
<211> LENGTH: 27
<212> TYPE: DNA
<213> ORGANISM: Hepatitis B Virus

<400> SEQUENCE: 39
tatatggatg atgtggtatt gggggcc                               27

<210> SEQ ID NO 40
<211> LENGTH: 27
<212> TYPE: DNA
<213> ORGANISM: Hepatitits B Virus

<400> SEQUENCE: 40
tatattgatg atgtggtatt gggggcc                               27

<210> SEQ ID NO 41
<211> LENGTH: 27
<212> TYPE: DNA
<213> ORGANISM: Hepatitis B Virus

<400> SEQUENCE: 41
tatgtggatg atgtggtatt gggggcc                               27

<210> SEQ ID NO 42
<211> LENGTH: 19
<212> TYPE: DNA
<213> ORGANISM: Artificial Sequence
<220> FEATURE:
<223> OTHER INFORMATION: Synthetic construct

<400> SEQUENCE: 42
cctgtattcc catcccatc                                        19

<210> SEQ ID NO 43
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 14
<223> OTHER INFORMATION: w = a or t
<220> FEATURE:
<221> NAME/KEY: variation
<222> LOCATION: 21
<223> OTHER INFORMATION: n = any nucleotide

<400> SEQUENCE: 43
tgtggtaccc caawaccaca ncatta                                26

<210> SEQ ID NO 44
<211> LENGTH: 26
<212> TYPE: DNA
<213> ORGANISM: Artificial Sequence
<220> FEATURE:
<221> NAME/KEY: variation
<222> LOCATION: 12
<223> OTHER INFORMATION: w = a or t
<220> FEATURE:
<221> NAME/KEY: variation
<222> LOCATION: 22
<223> OTHER INFORMATION: n = any nucleotide
<220> FEATURE:
<223> OTHER INFORMATION: Synthetic construct

<400> SEQUENCE: 44
```

```
tgatgtgcca awaccacatc anctac                                           26

<210> SEQ ID NO 45
<211> LENGTH: 22
<212> TYPE: DNA
<213> ORGANISM: Artificial Sequence
<220> FEATURE:
<223> OTHER INFORMATION: Synthetic construct

<400> SEQUENCE: 45
caaatgcccc tatcttatca ac                                               22

<210> SEQ ID NO 46
<211> LENGTH: 21
<212> TYPE: DNA
<213> ORGANISM: Artificial Sequence
<220> FEATURE:
<223> OTHER INFORMATION: Synthetic construct

<400> SEQUENCE: 46
gagattgaga tcttctgcga c                                                21

<210> SEQ ID NO 47
<211> LENGTH: 38
<212> TYPE: DNA
<213> ORGANISM: Artificial Sequence
<220> FEATURE:
<223> OTHER INFORMATION: Synthetic construct

<400> SEQUENCE: 47
cgtctgcgag gcgagggagt tcttcttcta ggcacacg                              38
```